United States Patent
Otsomaa et al.

(10) Patent No.: US 7,482,340 B2
(45) Date of Patent: *Jan. 27, 2009

(54) PYRIDINE DERIVATIVES USEFUL FOR INHIBITING SODIUM/CALCIUM EXCHANGE SYSTEM

(75) Inventors: Leena Otsomaa, Espoo (FI); Tuula Koskelainen, Lohja as (FI); Arto Karjalainen, Espoo (FI); Sirpa Rasku, Vantaa (FI); Piero Pollesello, Grankulla (FI); Jouko Levijoki, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 10/541,677

(22) PCT Filed: Jan. 9, 2004

(86) PCT No.: PCT/FI2004/000011

§ 371 (c)(1), (2), (4) Date: Oct. 28, 2005

(87) PCT Pub. No.: WO2004/063191

PCT Pub. Date: Jul. 29, 2004

(65) Prior Publication Data

US 2006/0241147 A1  Oct. 26, 2006

(30) Foreign Application Priority Data

Jan. 9, 2003 (FI) .................. 20030030

(51) Int. Cl.
 *A61K 31/54* (2006.01)
 *A61K 31/535* (2006.01)
 *A61K 31/44* (2006.01)

(52) U.S. Cl. .............. 514/227.5; 514/227.8; 514/235.5; 544/62; 544/60; 544/124

(58) Field of Classification Search .................. 514/302, 514/227.5, 227.8, 235.5; 546/281.7, 283.1, 546/283.7, 284.1; 544/62, 60, 124

See application file for complete search history.

(56) References Cited

U.S. PATENT DOCUMENTS 2,820,817 A    1/1958 Sam
(Continued)

FOREIGN PATENT DOCUMENTS

EP    0 978 506 A1    2/2000
(Continued)

OTHER PUBLICATIONS

Noble, D., "Simulation of Na/CA Exchange Activity during Ischemia," *Ann. N.Y. Acad. Sci.* (2002) 976:431-437.
(Continued)

*Primary Examiner*—Janet L Andres
*Assistant Examiner*—Binta M Robinson
(74) *Attorney, Agent, or Firm*—Finnegan, Henderson, Farabow, Garrett & Dunner, LLP

(57) ABSTRACT

Therapeutically active compounds of formula (I) or (II):

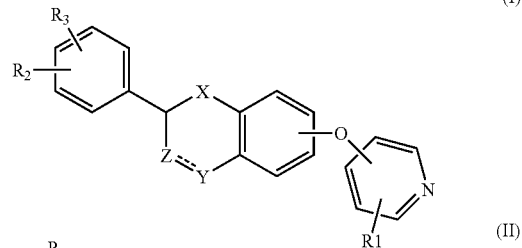

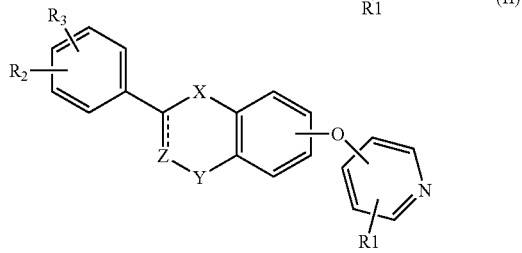

wherein the variables in formulas (I) and (II) are defined in the description, and pharmaceutically acceptable salts and esters thereof. The compounds are potent inhibitors of $Na^+/Ca^{2+}$ exchange mechanism.

7 Claims, 2 Drawing Sheets

U.S. PATENT DOCUMENTS

| | | | |
|---|---|---|---|
| 3,862,232 | A | 1/1975 | Lednicer |
| 5,703,118 | A | 12/1997 | Durand et al. |
| 6,177,449 | B1 | 1/2001 | Brendel et al. |
| 2004/0235905 | A1* | 11/2004 | Koskelainen et al. ........ 514/339 |

FOREIGN PATENT DOCUMENTS

| | | |
|---|---|---|
| EP | 1 031 556 A1 | 8/2000 |
| GB | 1 068 751 | 5/1967 |
| GB | 1 154 119 | 6/1969 |
| JP | 09067336 A2 | 3/1997 |
| JP | 11049752 A2 | 2/1999 |
| JP | 11302235 A2 | 11/1999 |
| WO | WO 00/64445 | 11/2000 |
| WO | WO 01/21610 A1 | 3/2001 |
| WO | WO 03/006452 A1 | 1/2003 |
| WO | WO03006452 * | 1/2003 |

OTHER PUBLICATIONS

Office Action from copending U.S. Appl. No. 10/482,396 dated Feb. 28, 2007.

Office Action from copending U.S. Appl. No. 10/482,396 dated Aug. 22, 2007.

Office Action from copending U.S. Appl. No. 10/482,396 dated Mar. 14, 2008.

Sipido, K. R. et al. "Altered Na/Ca exchange activity in cardiac hypertrophy and heart failure: a new target for therapy?" *Cardiovascular Research* (2002) 53:782-805.

Sipido, K. R. et al., "Sodium Calcium Exchange as a Target for Antiarrhythmic Therapy," *Handbook of Experimental Pharmacology*,NY: Springer-Verlag (2006) 171:159-199.

* cited by examiner

PYRIDINE DERIVATIVES USEFUL FOR INHIBITING SODIUM/CALCIUM EXCHANGE SYSTEM

This application is a U.S. national stage filing of POT international application No. PCT/FI2004/000011, filed on Jan. 9, 2004, which claims the benefit of priority to Finnish patent application No. 20030030, filed on Jan. 9, 2003.

TECHNICAL FIELD

The present invention relates to new therapeutically active compounds and pharmaceutically acceptable salts and esters thereof. The invention also relates to pharmaceutical compositions containing these compounds as active ingredients. The compounds of the invention are potent inhibitors of $Na^+/Ca^{2+}$ exchange mechanism.

BACKGROUND OF THE INVENTION $Na^+/Ca^{2+}$ exchange mechanism is one of the ion transport mechanisms that regulate the concentration of sodium and calcium ions in the cells. Compounds which selectively inhibit $Na^+/Ca^{2+}$ exchange mechanism and thereby prevent overload of $Ca^{2+}$ in cells are regarded useful in preventing the cell injury mechanism of cardiac muscle and the like after ischemia and reperfusion. Such compounds are useful e.g. in the treatment of ischemic diseases such as heart diseases, ischemic cerebral diseases, ischemic renal diseases and in the protection of cells during thrombolytic therapy, angioplasty, bypass operation of coronary artery or organ transplantation and arrhythmias.

Compounds capable of inhibiting $Na^+/Ca^{2+}$ exchange system have been described earlier e.g. in patent publications WO 97/09306, EP 0978506, EP 1031556, JP 11049752 and JP 11302235.

SUMMARY OF THE INVENTION

It has now been found that compounds of formula (I) or (II) are particularly potent inhibitors of $Na^+/Ca^{2+}$ exchange mechanism and are particularly useful in the treatment of arrhythmias.

The compounds of the present invention have a structure represented by formula (I) or (II):

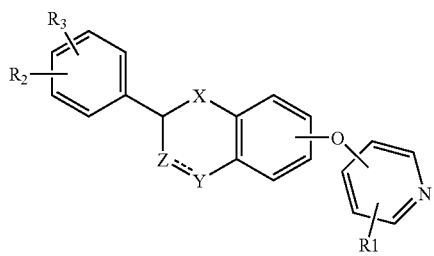

(I)

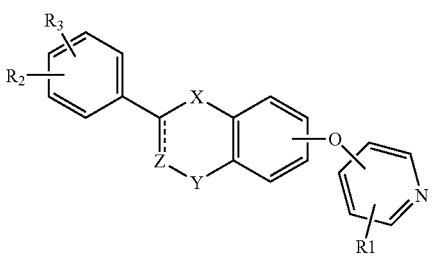

(II)

wherein
X is —O—, —CH$_2$— or —C(O)—;
Z is —CHR$_{12}$— or a valence bond;
Y is —CH$_2$—, —C(O)—, CH(OR$_{13}$)—, —O—, —S—;
provided that in case Z is a valence bond, Y is not C(O);
the dashed line represents an optional double bond in which case Z is —CR$_{12}$— and Y is —CH$_2$—, —C(O)— or CH(OR$_{10}$)— (in formula II) or —CH— (in formula I);

R$_2$ and R$_3$ are independently H, lower alkyl, lower alkoxy, —NO$_2$, halogen, —CF$_3$, —OH, benzyloxy or a group of formula (IIIa)

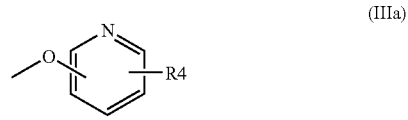

(IIIa)

R$_1$ is H, CN, halogen, —CONH$_2$, —COOR$_{15}$, —CH$_2$NR$_{15}$R$_{18}$, NHC(O)R$_5$, NHCH$_2$R$_5$, NHR$_{20}$, NR$_{21}$R$_{22}$, NHC(NH)NHCH$_3$ or, in case the compound is of formula (II) wherein the optional double bond exists or in case R$_2$ or R$_3$ is benzyloxy or a group of formula (IIIa) or in case the pyridine ring of formula (I) or (II) is attached to the oxygen atom in 3-, 4- or 5-position, R$_1$ can also be —NO$_2$ or NR$_{16}$R$_{17}$;

R$_4$ is H, —NO$_2$, CN, halogen, —CONH$_2$, —COOR$_{15}$, —CH$_2$NR$_{15}$R$_{18}$, —NR$_{16}$R$_{17}$; —NHC(O)R$_5$ or —NHC(NH)NHCH$_3$;

R$_5$ is alkyl substituted with 1-3 substituents selected from the group consisting of halogen, amino and hydroxy, or carboxyalkyl, in which the alkyl portion is optionally substituted with 1-3 substituents selected from the group consisting of halogen, amino and hydroxyl, —CHR$_6$NR$_7$R$_8$ or one of the following groups

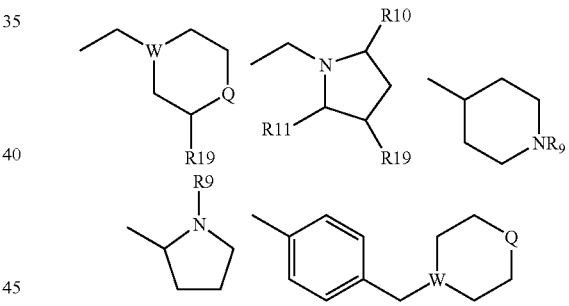

W is N or CH;
Q is CHR$_{14}$, NR$_9$, S or O;
R$_6$ is H or lower alkyl;
R$_7$ and R$_8$ are independently H, acyl, lower alkyl or lower hydroxyalkyl;
R$_9$ is H, lower alkyl or phenyl;
R$_{10}$ and R$_{11}$ are independently H or lower alkyl;
R$_{12}$ is H or lower alkyl;
R$_{13}$ is H, alkylsulfonyl or acyl;
R$_{14}$ is H, —OH, —COOR$_{15}$;
R$_{15}$ is H or lower alkyl;
R$_{16}$ and R$_{17}$ are independently H, acyl, alkylsulfonyl, —C(S)NHR$_{18}$ or —C(O)NHR$_{18}$;
R$_{18}$ is H or lower alkyl;
R$_{19}$ is H or —OH;
R$_{20}$ is a pyridinyl group optionally substituted with a —NO$_2$ group;
R$_{21}$ and R$_{22}$ are lower alkyl;
and pharmaceutically acceptable salts and esters thereof.

In one class of preferred compounds and pharmaceutically acceptable salts and esters thereof are compounds of formula (Ib) or (IIb), wherein $R_1$, $R_2$, $R_3$, X, Y and Z are as defined above.

(Ib)
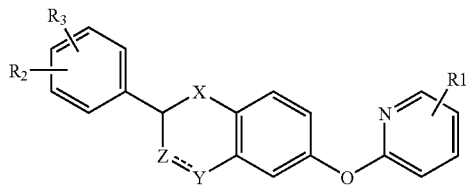

(IIb)
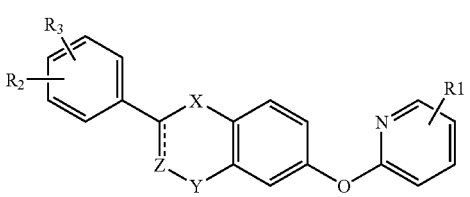

In a subclass of preferred compounds and pharmaceutically acceptable salts and esters thereof are compounds of formula (Ic) or (IIc), wherein $R_1$, $R_2$, $R_3$, X, Y and Z are as defined above.

(Ic)
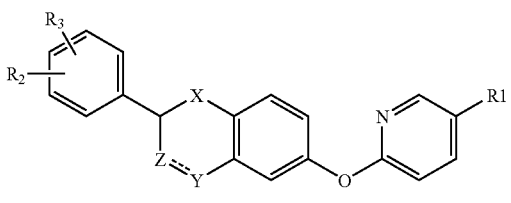

(IIc)
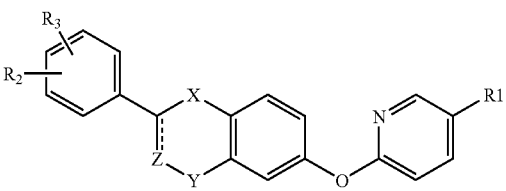

In another class of preferred compounds and pharmaceutically acceptable salts and esters thereof are compounds of formula (I) or (II) wherein $R_1$ is —NHC(O)$R_5$, X is O, Y is CH$_2$ and Z is CHR$_{12}$. In one subclass of preferred compounds and pharmaceutically acceptable salts and esters thereof are compounds of formula (I) or (II) wherein $R_1$ is —NHC(O)$R_5$, X is O, Y is CH$_2$, Z is CH$_2$ and $R_5$ is alkyl substituted with 1-3 substituents selected from the group consisting of halogen, amino and hydroxy, or carboxyalkyl, in which the alkyl portion is optionally substituted with 1-3 substituents selected from the group consisting of halogen, amino and hydroxyl, —CHR$_6$NR$_7$R$_8$ or one of the following groups:

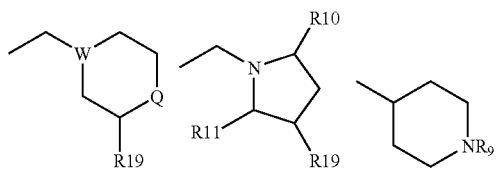

-continued

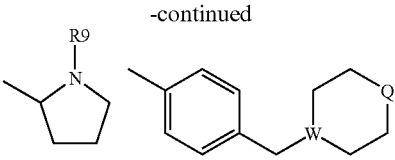

In other class of preferred compounds and pharmaceutically acceptable salts and esters thereof are compounds wherein $R_2$ or $R_3$ is a benzyloxy or a group of formula (IIIa)

(IIIa)
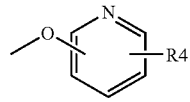

In one subclass of preferred compounds and pharmaceutically acceptable salts and esters thereof are compounds wherein $R_4$ and $R_1$ are NO$_2$.

The present invention also provides a pharmaceutical composition comprising a compound of formula (I) or (II) together with a pharmaceutically acceptable carrier.

The present invention further provides a method for inhibiting Na$^+$/Ca$^{2+}$ exchange mechanism in a cell, comprising administering to a subject in need thereof a therapeutically effective amount of a compound of formula (I) or (II).

The present invention further provides a method for preventing overload of Ca$^{2+}$ ions in cells, comprising administering to a subject in need thereof a therapeutically effective amount of a compound of formula (I) or (II).

The present invention further provides a method for treating arrhythmias, comprising administering to a subject in need thereof a therapeutically effective amount of a compound of formula (I) or (II).

DETAILED DESCRIPTION OF THE INVENTION

Figure 1:
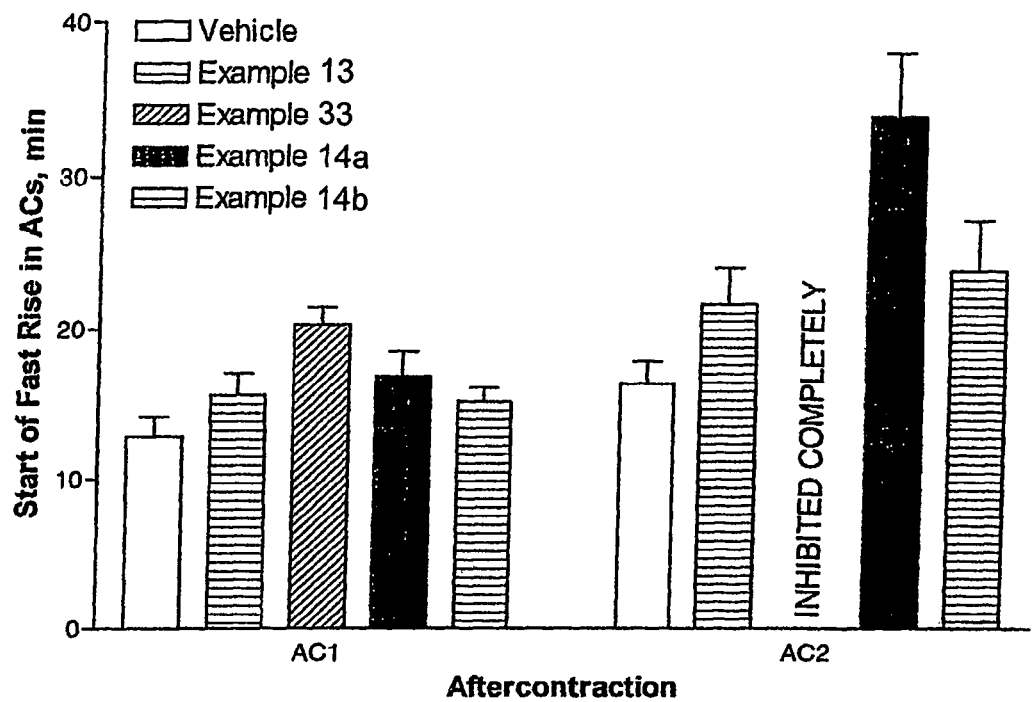
FIG. 1 shows the effects of the title compounds of Examples 13, 33, 14a and 14b on the start time of fast rise of ouabain-induced aftercontractions in guinea-pig papillary muscles.

The compounds of the invention can be prepared from corresponding phenol derivatives (IV), wherein $R_2$, $R_3$, X, Z and Y are the same as defined above.

(IV)
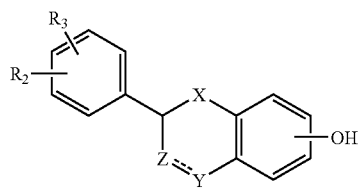

The syntheses are shown in Scheme 1, wherein formula (IV) is abbreviated as Ar—OH (IV). Pyridin-2-yloxy derivatives (1) are obtained by reactions with a suitable halopyridines (2) where $R_1$ can be hydrogen, nitro, cyano, halogen, or amide and $X_1$ chlorine or bromine. The nitropyridine and nicotinamide derivatives can be reduced to corresponding amines (3) and (4), respectively.

SCHEME 1

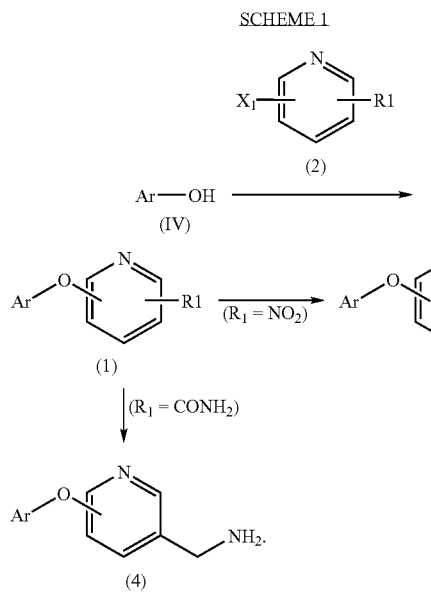

The reaction of 2-chloro-5-chloromethylpyridine (5) with diemethylamine results in (6-chloropyridin-3-ylmethyl)dimethylamine (6), which in turn can be reacted with phenol derivatives (IV), as shown in Scheme 2.

SCHEME 2

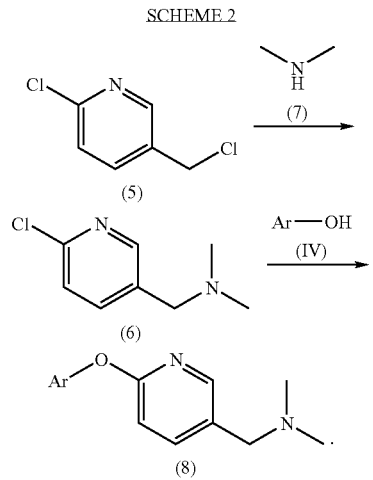

Nicotinic acid derivatives (12) and their esters (11) are obtained as shown in Scheme 3. The esterification of 6-chloronicotinic acid and its reaction with phenol derivatives (IV) gives nicotinic acid ester derivatives (11) (R can be lower alkyl). Nicotinic acid derivatives (12) are obtained upon hydrolysis.

SCHEME 3

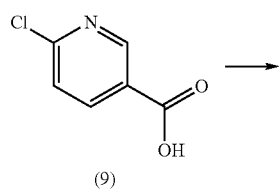

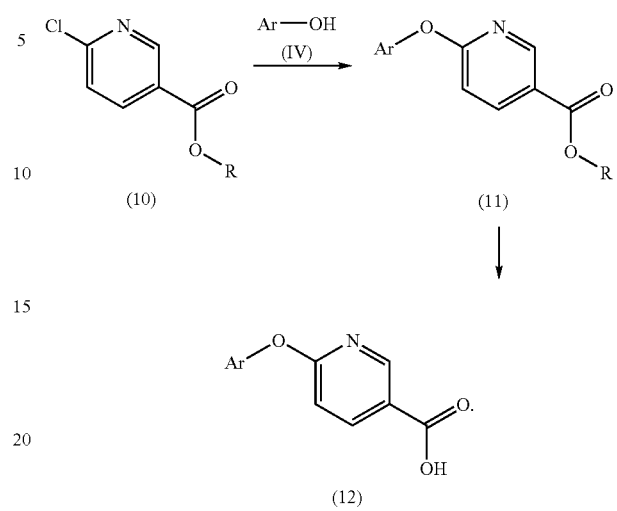

The aminopyridine derivatives (3) are reacted with suitable amino acids and other carboxylic acid derivatives using 1-(dimethylaminopropyl)-3-ethylacarbodiimide hydrochloride as an coupling agent to result in amide derivatives (13) as shown in the following Scheme 4 wherein $R_5$ is as defined above. Optionally the amide derivatives of (13) can be obtained by well-known acylation methods. Protecting groups are removed if needed.

SCHEME 4

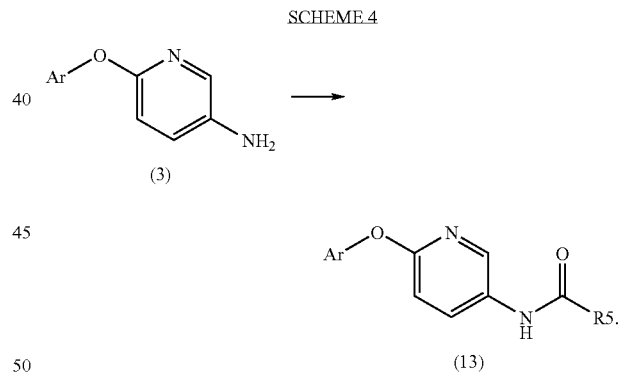

4-(4-methylpiperazin-1-ylmethyl)benzoic acid (17) is obtained as described in the following Scheme 5. 4-Chloromethylbenzoic acid (14) is first esterified to a methyl ester to protect an acid group in the following reaction. 4-Chloromethyl-benzoic acid methyl ester (15) is then allowed to react with 1-methylpiperazine to give 4-(4-methylpiperazin-1-ylmethyl)benzoic acid methyl ester (16). Methyl ester is cleaved by heating with potassium hydroxide in methanol. 4-(4-methylpiperazin-1-ylmethyl)benzoic acid is reacted as described above in Scheme 4 with aminopyridine derivatives (3) to result in N-4-(4-methylpiperazin-1-ylmethyl)benzamide derivatives of (13). By a similar manner other N-4-(piperazin-1-ylmethyl)benzamide derivatives of (13) can be prepared.

SCHEME 5

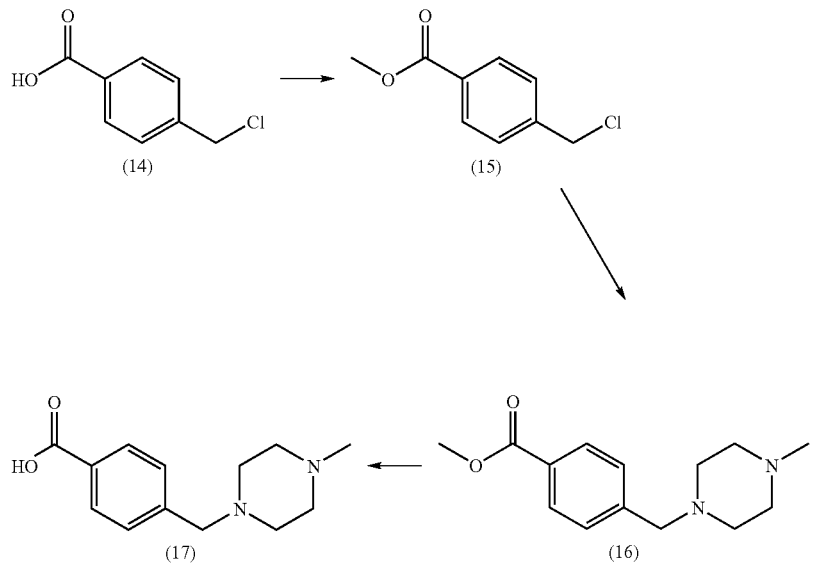

The 2-chloroacetamide derivatives (13') where $R_5$ is $CH_2Cl$ are reacted with sodium azide to result in azide derivatives (18) which in turn are reduced to corresponding 2-aminoacetamide derivatives (19) as shown in the following Scheme 6 wherein $R_7$ and $R_8$ are as defined above. The acetamide derivatives (20) are obtained from 2-chloroacetamide derivatives (13') by reaction with various amines. The amide moiety of acetamide derivatives (20) can be reduced in order to result in corresponding amines (21).

As shown in the following Scheme 7, wherein $R_2$ and $R_3$ are the same as defined above, 6- and 7-hydroxyflavane derivatives (23) are obtained from corresponding flavanones (22) by Clemmensen reduction. 6- and 7-hydroxyflavanones (22) are commercially available or can be synthesised by methods described in the literature, e.g. *J. Org Chem.*, 1960, 25, 1247-9 and *J. Org. Chem.*, 1958, 23, 1159-61 or as described later in Scheme 9.

SCHEME 6

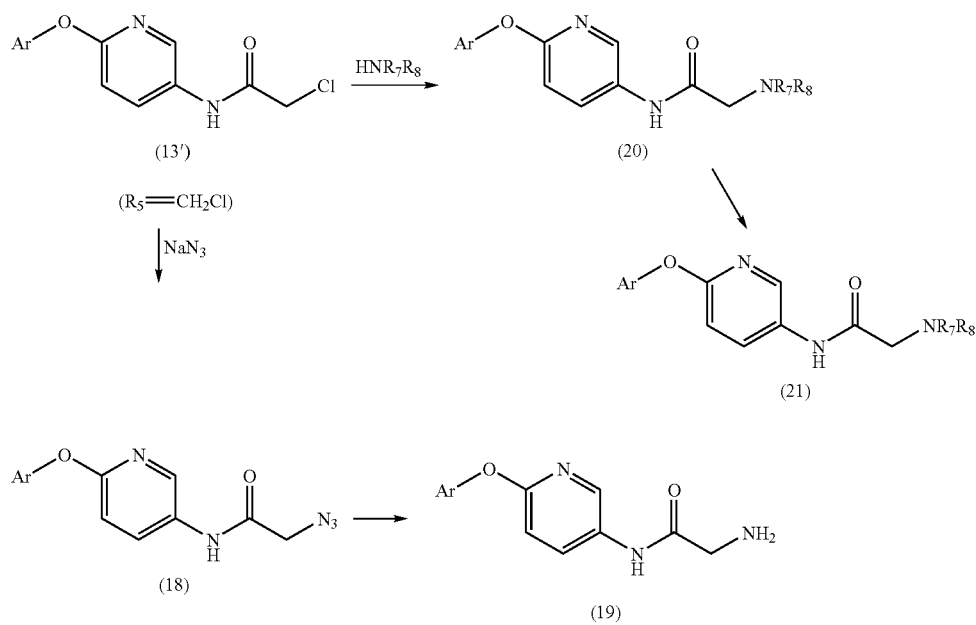

SCHEME 7

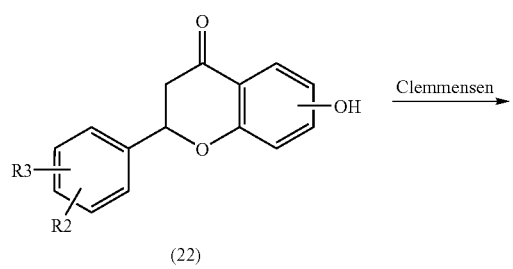

The following Scheme 8, wherein $R_2$ and $R_3$ are the same as defined above, describes the synthesis of 2-phenyl indan-5-ols (30). Condensation of p-anisaldehyde (24) with substituted phenyl acetic acid (25) gives mixture of cis-and trans-isomers of the corresponding acrylic acid (26). After hydrogenation and intramolecular Friedel-Crafts reaction carbonyl functionality of 1-indanones (28) can be reduced by Clemmensen reduction. Finally methoxy indane (29) is refluxed in concentrated hydrobromic acid to obtain 2-phenyl indan-5-ols (30).

6-Hydroxyflavanone derivatives can be synthesised as shown in Scheme 9 wherein $R_2$, $R_3$ and $R_{12}$ are as defined above. 2',5'-Dihydroxyacetophenone or corresponding propiophenone (32) is condensed with appropriate benzaldehyde (31) resulting in a mixture of desired 6-hydroxyflavanone (34) and the corresponding chalcone (35). The chalcone can be cyclised to flavanone.

SCHEME 9

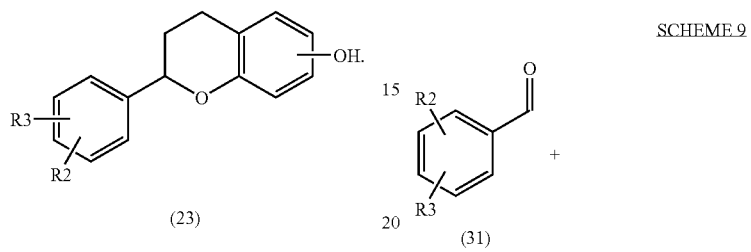

SCHEME 8

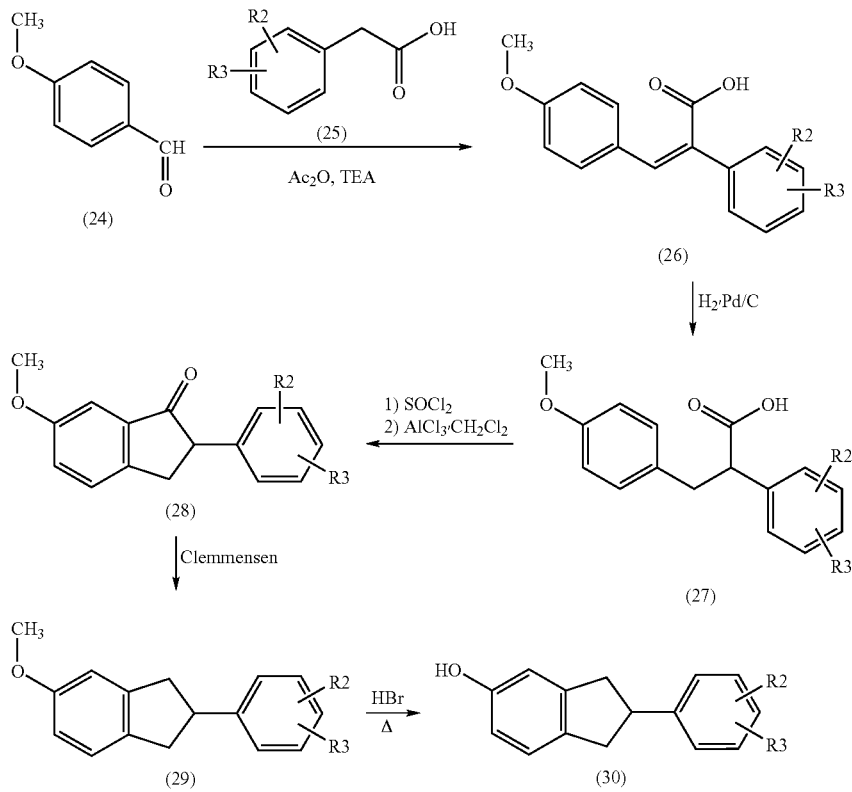

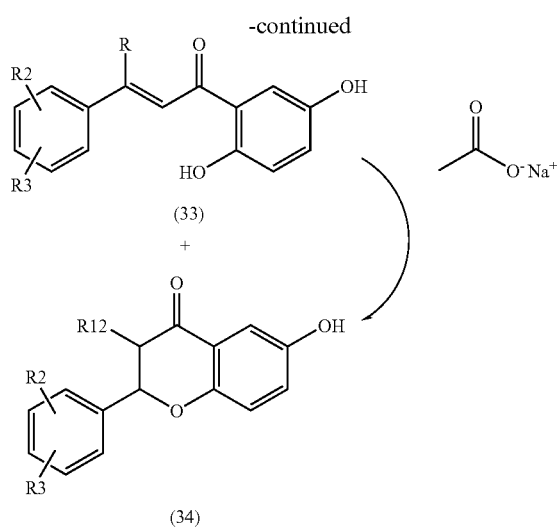

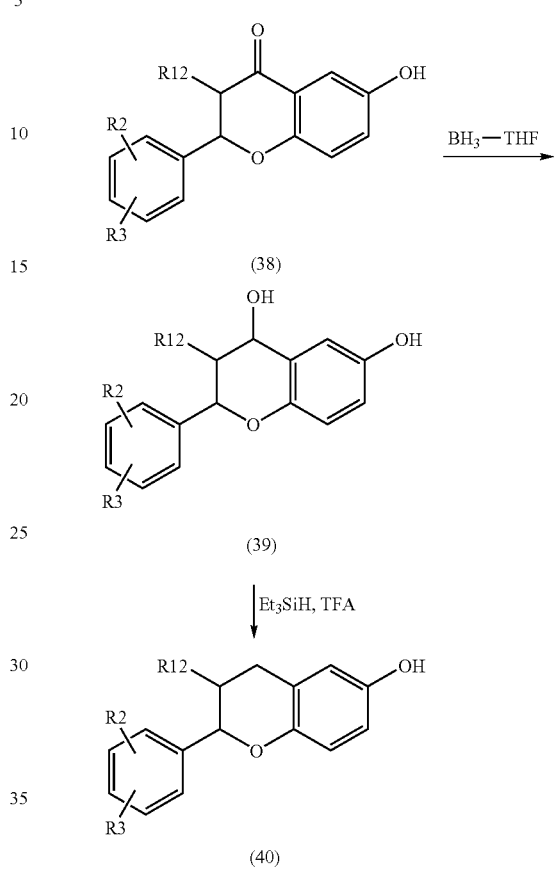

The benzaldehyde derivatives of (31) wherein $R_2$ and $R_3$ can contain pyridine moiety are obtained by the reaction of hydroxybenzaldehydes (35) with pyridine derivatives (36) (where $X_1$ can be chlorine or bromine and R' hydrogen, nitro or halogen) as shown in Scheme 10.

SCHEME 10

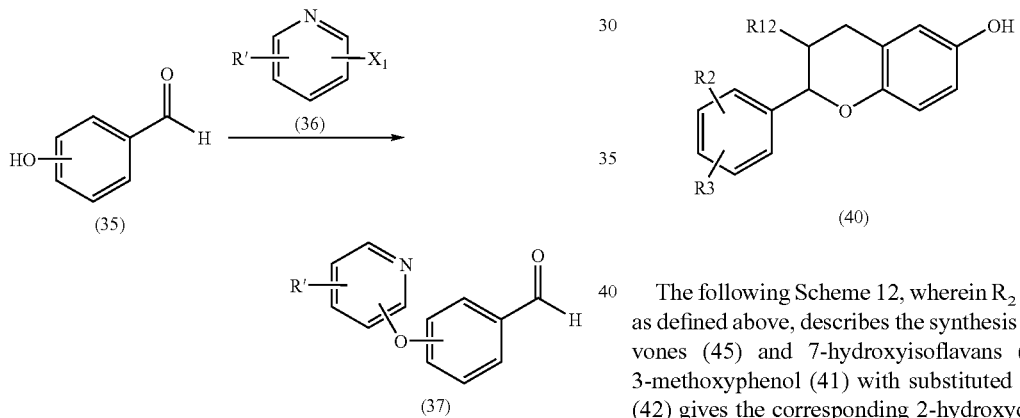

2-Phenylchroman-4,6-diol derivatives (39) are obtained from corresponding 6-hydroxyflavanones (38) by reduction as shown in Scheme 11 wherein $R_2$, $R_3$ and $R_{12}$ are as defined above. These diol derivatives can be reduced further into 6-hydroxyflavanes (40).

SCHEME 11

The following Scheme 12, wherein $R_2$ and $R_3$ are the same as defined above, describes the synthesis of 7-hydroxyisoflavones (45) and 7-hydroxyisoflavans (46). Acylation of 3-methoxyphenol (41) with substituted phenyl acetic acids (42) gives the corresponding 2-hydroxydeoxybenzoins (43) which can be cyclised with triethylorthoformate to yield isoflavones (44). Deprotection with hydrobromic acid and catalytic hydrogenation gives 7-hydroxyisoflavans (46).

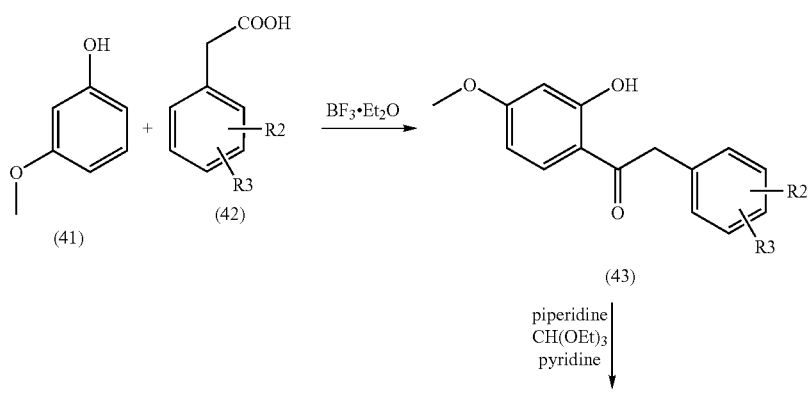

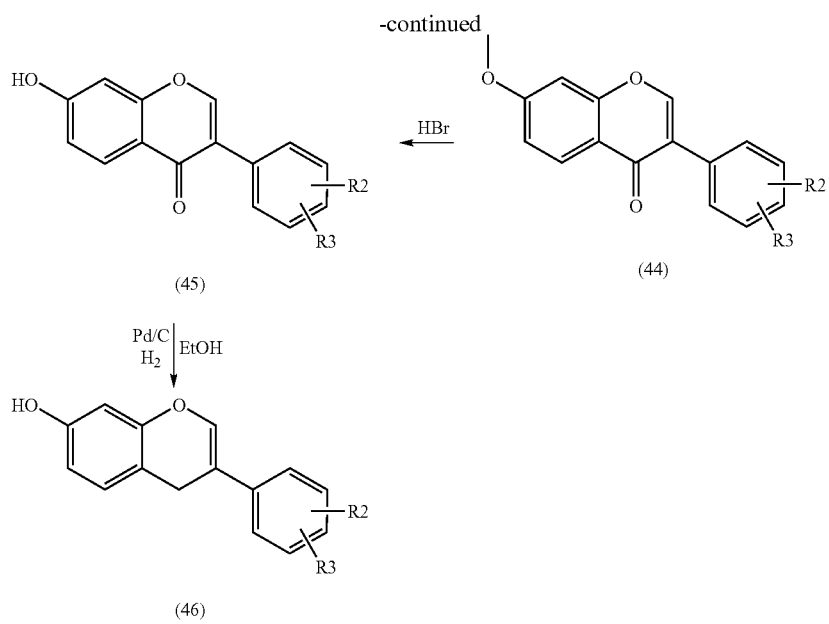

(45)  (44)  (46)

The following Scheme 13 describes the synthesis of 2-phenyl-2,3-dihydrobenzo[1,4]oxathiin-6-ol (50). The reaction of 2-mercaptobenzene-1,4-diol (47) with styrene epoxide (48) in the presence of base gives sulphide (49). The ring closure with an acid ion exchanger affords 2-phenyl-2,3-dihydrobenzo[1,4]oxathiin-6-ol (50).

SCHEME 14

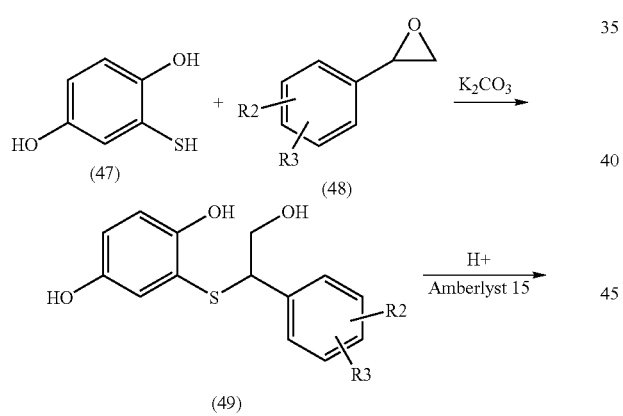

-continued

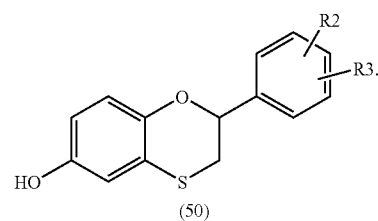

(50)

The following Scheme 14 describes the synthesis of 6-phenyl-5,6,7,8-tetrahydro-naphthalen-2-ol (55) and 6-hydroxy-2-phenyl-3,4-dihydro-2H-naphthalen-1-one (54). Palladium catalyzed α-arylation of 6-methoxy-1-tetralone (51) gives 6-methoxy-2-phenyl-3,4-dihydro-2H-naphthalen-1-one (53) which after demethylation leads to the phenolic compound (54). Reduction with triethylsilane gives 6-phenyl-5,6,7,8-tetrahydronaphthalen-2-ol (55).

SCHEME 14

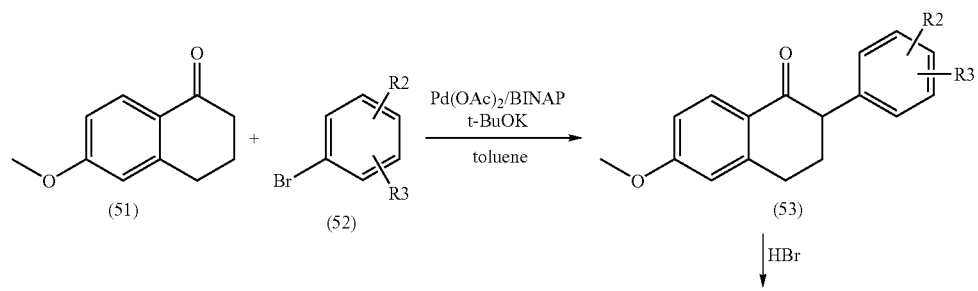

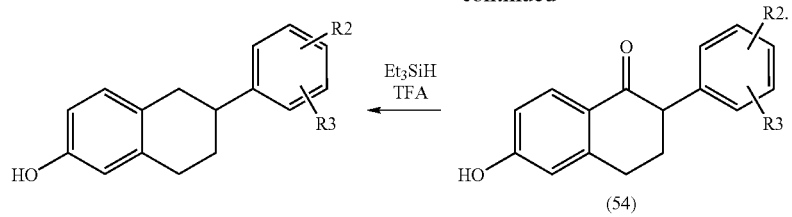

The following Scheme 15, wherein $R_2$ and $R_3$ are as defined above and R" is an appropriate protecting group, describes the synthesis of 2,3-dihydro-2-phenyl-benzo[1,4]dioxin-6-ols (60). After the protecting hydroxyl groups of 2,5-dihydroxyacetophenone are removed, this ketone rearranges with peracids and gives a phenol (56) after hydrolysis. The phenol (56) is condensed with a haloketone and after reduction and removal of protection groups the hydroxyphenol (59) is cyclised to a 2,3-dihydro-2-phenyl-benzo[1,4]-dioxin-6-ol (60).

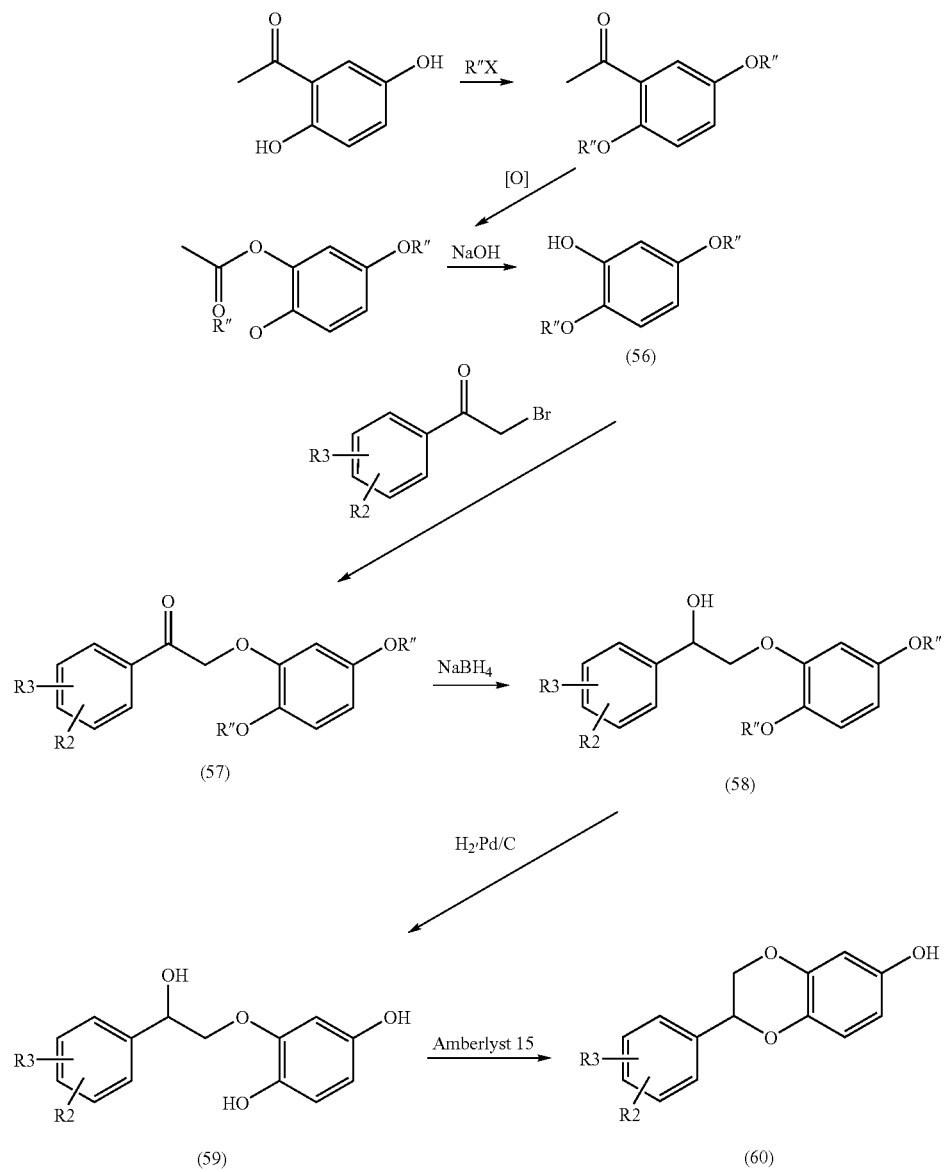

Dihydroxyflavane derivatives (61) can be reacted with pyridine derivatives in a similar manner as described for compound (1) in Scheme 1. 4-Chromanol derivative of (62), where R* is OH, can be reduced to corresponding flavane with triethylsilane in acidic media. 5-nitropyridine derivatives (62) are reduced to corresponding 2-aminoderivatives (63), which in turn can be acylated or mesylated or reacted with various aminoacid- or carboxylic acid derivatives as described in Scheme 4 for compound (13).

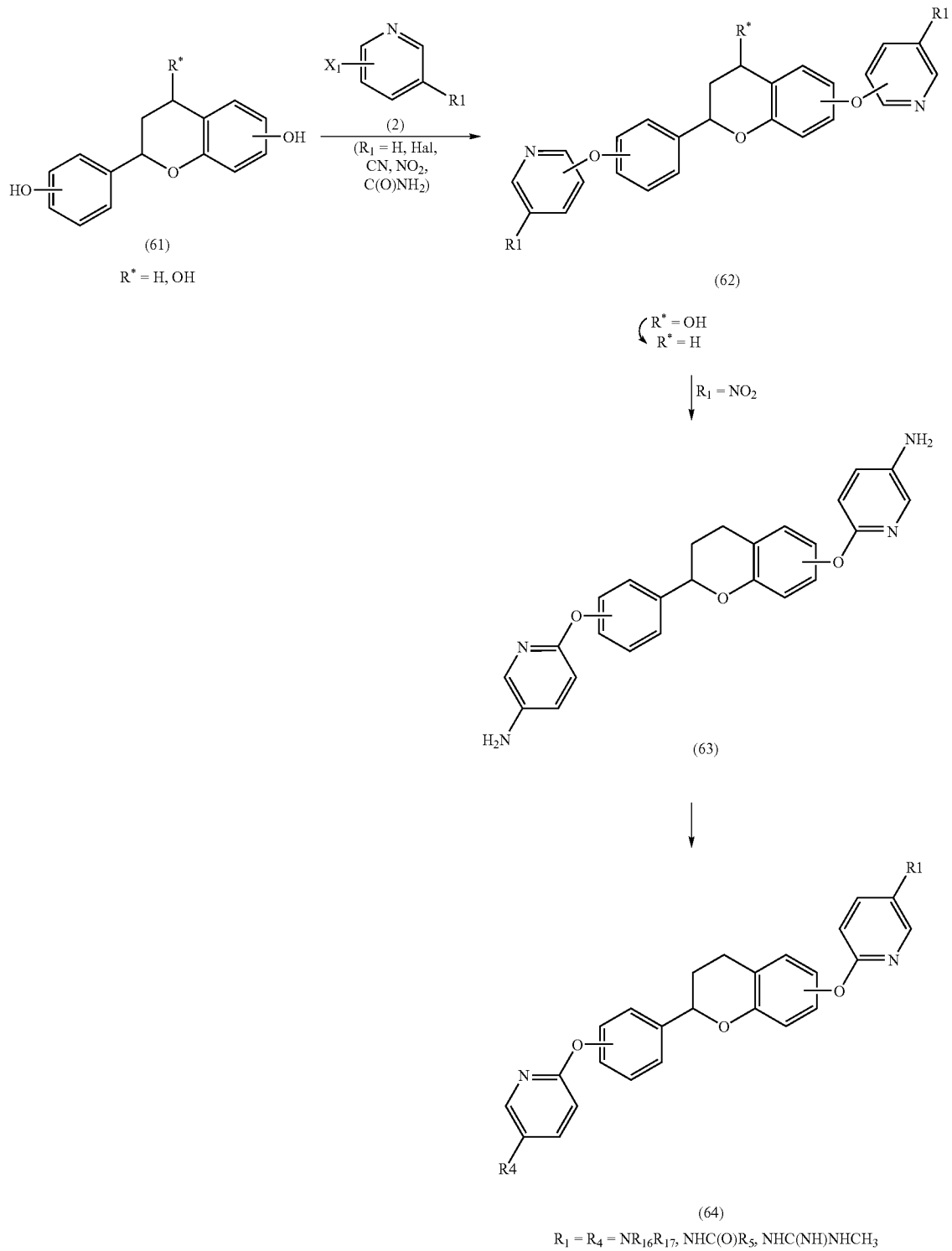

SCHEME 16

When the nitro group in the benzyloxy derivatives (65) is reduced by hydrogenation using palladium as catalyst there are obtained [6-(5-aminopyridin-2-yloxy)chroman-2-yl]phenol derivatives (68) which in turn can be acylated or mesylated. These phenol derivatives (69) can then be reacted with pyridine derivatives (2) to result in derivatives like (70) as shown in the following Scheme 17. The reduction with zinc leads to amines like (66) which in turn can be acylated, mesylated or reacted with various amino acid- or carboxylic acid derivatives as described in Scheme 4 for compound (13).

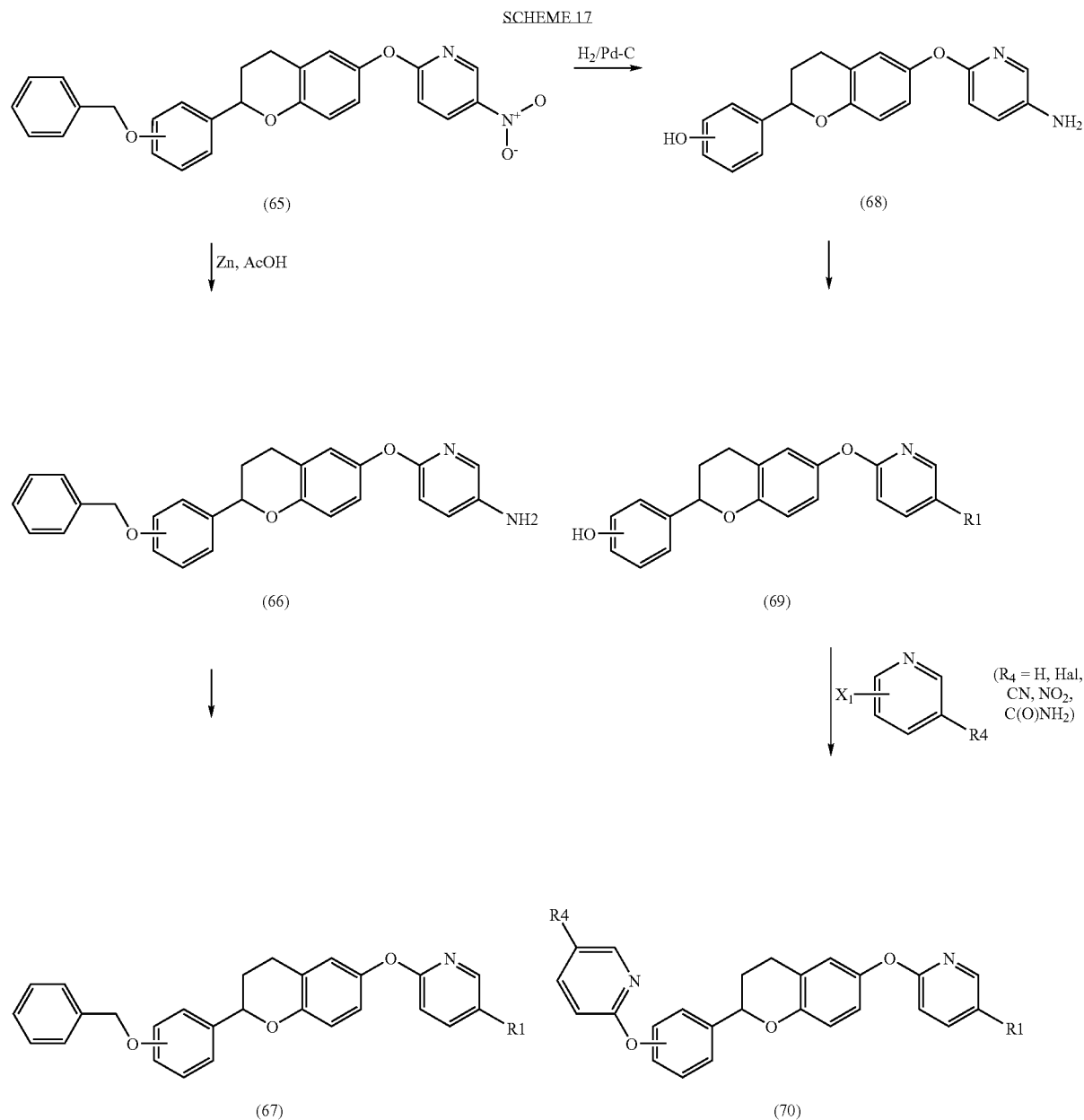

Alkyl derivatives of aminopyridines (3) can be obtained by reductive amination as shown in Scheme 18 for dimethylamine derivatives (71). In the course of the reaction the amine moiety is partially rearranged from 5 to 4 position.

SCHEME 18

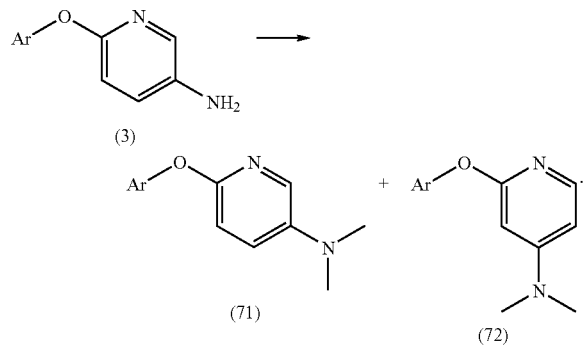

The following Scheme 19, describes the synthesis of 1-methyl-3-(pyridinyl)thiourea (73) and N-methyl-N'-(pyridynyl) guanidine (74) derivatives. Aminopyridine derivatives (3) were reacted with methyl isothiocyanate to result in tioura derivatives (73), which in turn were treated first with methyl iodide and then with methanolic solution of ammonia in order to obtain guanidine derivatives (74).

SCHEME 19

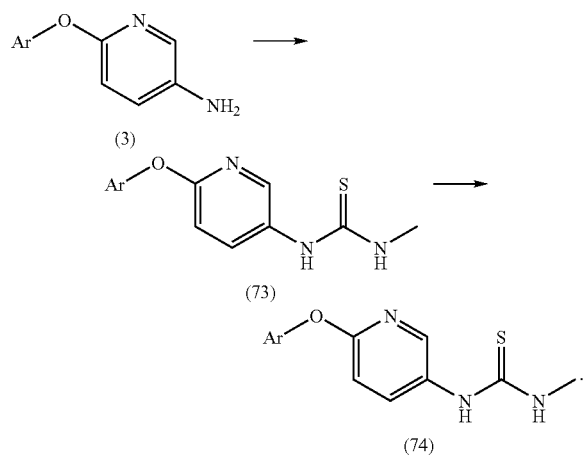

Salts and esters of the compounds, when applicable, may be prepared by known methods. Physiologically acceptable salts are useful as active medicaments. Examples are the salts with inorganic acids such as hydrochloric acid, hydrobromic acid or nitric acid, and salts with organic acids such as methanesulfonic acid, citric acid or tartaric acid. Physiologically acceptable esters are also useful as active medicaments. Examples are the esters with aliphatic or aromatic acids such as acetic acid or with aliphatic or aromatic alcohols such as ethanol.

The term "alkyl" as employed herein by itself or as part of another group includes both straight, branched and cyclised chain radicals of up to 18 carbon atoms, preferably 1 to 7 carbon atoms. The term "lower alkyl" as employed herein by itself or as part of another group includes straight, branched and cyclized chain radicals of 1 to 7 carbon atoms. Specific examples for the alkyl and lower alkyl residues, respectively, are methyl, ethyl, propyl, isopropyl, butyl, tert. butyl, pentyl, cyclopentyl, hexyl, cyclohexyl, octyl, decyl and dodecyl including the various branched chain isomers thereof.

The term "alkoxy" as employed herein by itself or as part of another group includes an alkyl group as defined above linked to an oxygen atom.

The term "acyl" as employed herein by itself or as part of another group refers to an alkylcarbonyl or alkenylcarbonyl group, the alkyl and alkenyl groups being defined above.

Compounds of the invention may be administered to a patient in therapeutically effective amounts which range usually from about 0.05 to 200 mg, preferably 0.1 to 100 mg, more preferably 0.5 to 50, mg per day depending on the age, weight, condition of the patient, administration route and the $Na^+/Ca^{2+}$ exchange inhibitor used. The compounds of the invention can be formulated into dosage forms using the principles known in the art. It can be given to a patient as such or in combination with suitable pharmaceutical excipients in the form of tablets, granules, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100%, preferably from about 0.5 to about 20%, per weight of the total composition.

Experiments

The effects of the compounds of the invention were tested on ouabain-induced arrhythmias in guinea-pig papillary muscles.

Methods

Guinea-pig papillary muscles were mounted into horizontal muscle cuvette. A hook connected to force transducer was attached to another end of the muscle. Muscle preparations were electrically paced at 1 Hz with field stimulation via platinum electrodes. Modified Tyrode solution was used for superfusion of muscle preparations. The composition of the Tyrode solution was the following (mM): NaCl 135, $MgCl_2 \times 6H_2O$ 1, KCl 5, $CaCl_2 \times 2H_2O$ 2, $NaHCO_3$ 15, $Na_2HPO_4 \times 2H_2O$ 1, and glucose 10. The Tyrode solution was gassed with carbogen (95% $O_2$, 5% $CO_2$) to set pH at 7.4. Experiments were carried out at 37° C. Acquisition and analysis of twitch tensions with Action Potential and Force Measurement System (ACFO v1.0, Fision Ltd, Finland).

Inhibition of Ouabain-Induced Arrhythmias

Ouabain by blocking of sodium-potassium ATPase increases intracellular sodium which is changed for calcium via NCX. Increased intracellular calcium is leading to overload of sarcoplasmic reticulum (SR) and spontaneous calcium release from SR inducing delayed afterpolarizations (DADs). Equivalence for DADs in force signal is aftercontractions (ACs) which are seen as spontaneous twitches after the pacing controlled twitch.

Figure 2:
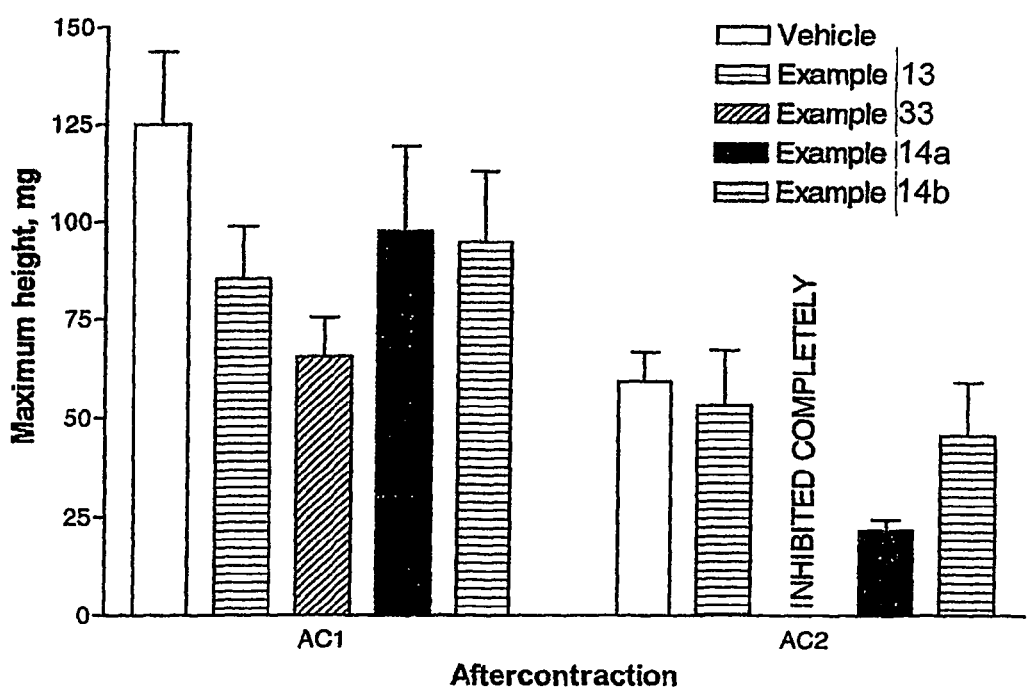
FIG. 2 shows the effects of the compounds of Examples 13, 33, 14a and 14b on the maximum heights of ouabain-induced aftercontractions in guinea-pig papillary muscles.
Figure 3:
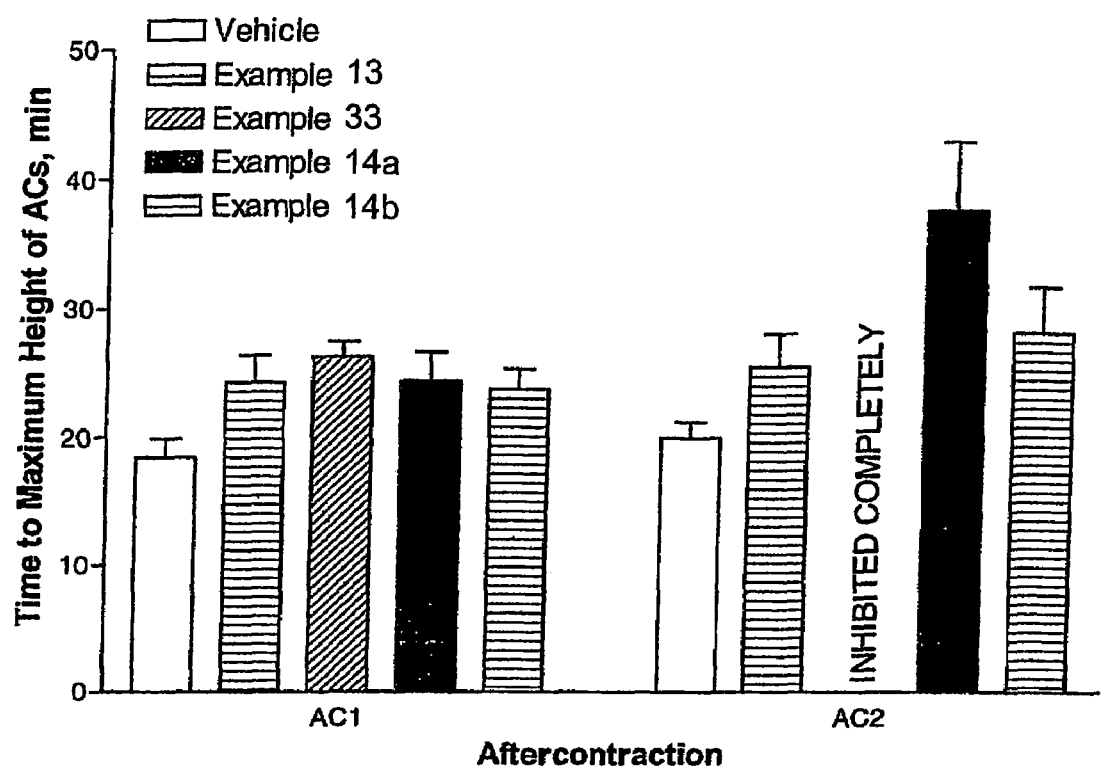
FIG. 3 shows the effects of the compounds of Examples 13, 33, 14a and 14b on the time to maximum heights of ouabain-induced aftercontractions in guinea-pig papillary muscles.

The antiarrhythmic effects of the title compounds of Examples 13, 33, 14a and 14b were examined. The results are shown in FIGS. 1 to 3. FIG. 1 shows the effects of the compounds on the start time of fast rise of ouabain-induced aftercontractions. FIG. 2 shows the effects of the compounds on the maximum heights of ouabain-induced aftercontractions in guinea-pig papillary muscles. FIG. 3 shows the effects of the compounds on the time to maximum heights of ouabain-induced aftercontractions in guinea-pig papillary muscles.

In general, the compounds of the invention delayed appearance and decreased the amplitude of aftercontractions. The title compound of Example 33, at 10 μM concentration, was able to inhibit completely the emergency of ouabain-induced second aftercontraction.

EXAMPLES

Examples 1 to 11 generally describe the preparation of intermediates of the compounds of the invention. The preparation of the compounds of the invention is generally described from Example 12 onwards.

Example 1

Intermediates a) 2-phenylchromanol Intermediates 2-phenylchroman-6-ol

Zinc (5.4 g, 83.2 mmol), mercury (II) chloride (340 mg), concentrated hydrogen chloride (0.2 ml) and water were mixed at room temperature for 15 minutes and the mixture was decanted. 6-Hydroxyflavanone (1,0 g) was added as a suspension in a mixture of acetic acid (25 ml), concentrated hydrogen chloride (5.2 ml) and water (2 ml). The reaction mixture was refluxed for 1½ hours. After cooling into room temperature, the reaction mixture was filtered and the filtrate was extracted with ethyl acetate. The combined organic layers were washed with saturated $NaHCO_3$-solution, then with water and dried with $Na_2SO_4$. The 2-phenylchroman-6-ol was purified by column chromatography using heptane-ethyl acetate (2:1) as an eluant. $^1$H NMR (400 MHz, $d_6$-DMSO) δ: 8.78 (s, 1H), 7.43-7.31 (m, 5H), 6.63 (d, 1H, J 8.6 Hz) 6.51 (dd, 1H, J 8.6, 2.9 Hz), 6.48 (d, 1H, J 2.9 Hz), 4.98 (dd, 1H, J, 9.9, 2.2 Hz), 2.89 (ddd, 1H, J −16.7, 11.3, 6.1 Hz), 2.63 (ddd, 1H, J −16.7, 5.5, 3.3 Hz) 2.10 (m, 1H), 1.94 (m, 1H).

Using the same procedure as described above for 2-phenylchroman-6-ol, but replacing 6-hydroxyflavanone by 7-hydroxyflavanone, there was obtained:

2-Phenylchroman-7-ol $^1$H NMR (400 MHz, $CD_3OD$) δ: 7.41-7.28 (m, 5H), 6.86 (d, 1H, J 8.2 Hz) 6.32 (dd, 1H, J 8.2, 2.4 Hz), 6.29 (d, 1H, J 2.4 Hz), 5.00 (dd, 1H, J 9.9, 2.4 Hz), 2.84 (m, 1H), 2.64 (m, 1H) 2.15 (m, 1H), 1.99 (m, 1H).

b) 5-Nitro-2-(2-(nonsubstituted)phenylchromanyloxy)pyridine intermediates

5-Nitro-2-(2-phenylchroman-6-yloxy)pyridine

Potassium fluoride (225 mg) was added into a solution of 2-phenylchroman-6-ol (300 mg) in dry DMF (3 ml). After stirring the resulting mixture at 120° C. for 30 minutes 2-chloro-5-nitropyridine (195 mg) was added. The reaction mixture was stirred for a further 6½ hours at 120° C. After cooling into room temperature 1 M HCl-solution was added and the mixture was extracted with ethyl acetate. The combined organic layers were washed with water then with saturated NaCl-solution and dried with $Na_2SO_4$. 5-Nitro-2-(2-phenylchroman-6-yloxy)-pyridine was recrystallised from acetone-2-propanol (1:5). $^1$H NMR (400 MHz, $d_6$-DMSO) δ: 9.00 (d, 1H, J 2.9 Hz), 8.60 (dd, 1H, J 9.2, 2.9 Hz), 7.47-7.32 (m, 5H), 7.20 (d, 1H, J 9.2 Hz), 7.00-6.89 (m, 3H), 5.15 (dd, 1H, J 10.1, 2.2 Hz), 2.99 (ddd, 1H, J −16.8, 11.3, 6.2 Hz), 2.75 (ddd, 1H, J −16.8, 5.4, 3.3 Hz) 2.18 (m, 1H), 2.02 (m, 1H).

Using the same procedure as described above for 5-nitro-2-(2-phenylchroman-6-yloxy)pyridine, but replacing 2-phenylchroman-6-ol by 2-phenylchroman-7-ol, there was obtained:

5-Nitro-2-(2-phenylchroman-7-yloxy)pyridine $^1$H NMR (400 MHz, $d_6$-DMSO) δ: 9.04 (d, 1H, J 2.8 Hz), 8.60 (dd, 1H, J 9.1, 2.8 Hz), 7.46-7.32 (m, 5H), 7.22 (d, 1H, J 9.1 Hz), 7.20 (d, 1H, J 8.9 Hz) 6.72 (dd, 1H, J 8.9, 2.3 Hz), 6.72 (d, 1H, J 2.3 Hz), 5.16 (dd, 1H, J 10.1, 2.1 Hz), 2.97 (ddd, 1H, J −16.7, 11.3, 5.9 Hz), 2.77 (ddd, 1H, J −16.7, 8.1, 4.5 Hz) 2.20 (m, 1H), 2.02 (m, 1H).

Example 2

Intermediates a) Chroman-4-none Intermediates

6-Hydroxy-2-(4-fluorophenyl)chroman-4-one

2',5'-Dihydroxyacetophenone (3.0 g) was dissolved in warm glacial acetic acid (40 ml). 4-Fluorobenzaldehyde (2.4 ml) and ammonium acetate (1.97 g) were added. The reaction mixture was refluxed for 8 hours. It was allowed to cool to room temperature and poured in ice. The precipitate formed was filtered resulting in 4.23 g of a mixture of 2-(4-fluorophenyl)-6-hydroxychroman-4-one and 1-(2,5-dihydroxy-phenyl)-3-(4-fluorophenyl)propenone. The obtained mixture was dissolved in ethanol (75 ml) and sodium acetate (3.4 g) was added. The reaction mixture was refluxed for 5 hours. It was then allowed to cool to room temperature and diluted with water and filtered. The 2-(4-fluorophenyl)-6-hydroxychroman-4-one was recrystallised from acetic acid. $^1$H NMR (400 MHz, $d_6$-DMSO) δ: 7.59 (m, 2H), 7.27 (m, 2H), 7.14 (d, 1H, J 3.1 Hz), 7.05 (dd, 1H, J 8.9, 3.1 Hz), 6.96 (d, 1H, J 8.9 Hz), 5.56 (dd, 1H, J 13.2, 2.8 Hz), 3.18 (dd, 1H, J −16.9, 13.2 Hz), 2.77 (dd, 1H, J −16.9, 2.8 Hz).

Using the same procedure as described above for 6-hydroxy-2-(4-fluorophenyl)chroman-4-one, but replacing 4-fluorobenzaldehyde by an appropriate benzaldehyde, there was obtained:

2-(3-Fluorophenyl)-6-hydroxychroman-4-one $^1$H NMR (400 MHz, $d_6$-DMSO) δ: 9.45 (s, 1H), 7.47 (m, 1H), 7.40-7.37 (m, 2H), 7.22 (m, 1H), 7.12 (d, 1H, J 3.0 Hz), 7.05 (dd, 1H, J 8.8, 3.0 Hz), 6.98 (d, 1H, J 8.8 Hz), 5.59 (dd, 1H, J 13.0, 2.9 Hz), 3.21 (dd, 1H, J −16.9, 13.0 Hz), 2.82 (dd, 1H, J −16.9, 2.9 Hz).

2-(2-Fluorophenyl)-6-hydroxychroman-4-one $^1$H NMR (400 MHz, $d_6$-DMSO) δ: 9.45 (s, 1H), 7.67 (m, 1H), 7.47 (m, 1H), 7.32-7.25 (m, 2H), 7.14 (d, 1H, J 3.0 Hz), 7.04 (dd, 1H, J 8.9, 3.0 Hz), 6.95 (d, 1H, J 8.9 Hz), 5.77 (dd, 1H, J 13.5, 2.8 Hz), 3.26 (dd, 1H, J −16.9, 13.5 Hz), 2.76 (dd, 1H, J −16.9, 2.8 Hz).

2-(2,3-Difluorophenyl)-6-hydroxychroman-4-one $^1$H NMR (400 MHz, $d_6$-DMSO) δ: 9.51 (s, 1H), 7.53-7.46 (m, 2H), 7.31 (m, 1H), 7.14 (d, 1H, J 3.0 Hz), 7.05 (dd, 1H, J 8.8, 3.0 Hz), 6.96 (d, 1H, J 8.8 Hz), 5.82 (dd, 1H, J 13.4, 2.8 Hz), 3.26 (dd, 1H, J −16.9, 13.4 Hz), 2.79 (dd, 1H, J −16.9, 2.8 Hz).

2-(2,4-Difluorophenyl)-6-hydroxychroman-4-one $^1$H NMR (400 MHz, d$_6$-DMSO) δ: 9.46 (s, 1H), 7.73 (m, 1H), 7.34 (m, 1H), 7.19 (m, 1H), 7.13 (d, 1H, J 2.9 Hz), 7.04 (dd, 1H, J 8.8, 2.9 Hz), 6.95 (d, 1H, J 8.8 Hz), 5.74 (dd, 1H, J 13.5, 2.8 Hz), 3.28 (dd, 1H, J −16.9, 13.5 Hz), 2.74 (dd, 1H, J −16.9, 2.8 Hz).

2-(2,5-Difluorophenyl)-6-hydroxychroman-4-one $^1$H NMR (300 MHz, d$_6$-DMSO) δ: 9.46 (s, 1H), 7.53 (m, 1H), 7.36-7.30 (m, 2H), 7.14 (d, 1H, J 3.0 Hz), 7.05 (dd, 1H, J 8.8, 3.0 Hz), 6.97 (d, 1H, J 8.8 Hz), 5.76 (dd, 1H, J 13.6, 2.7 Hz), 3.26 (dd, 1H, J −16.8, 13.6 Hz), 2.76 (dd, 1H, J −16.8, 2.7 Hz).

2-(2,6-Difluorophenyl)-6-hydroxychroman-4-one $^1$H NMR (400 MHz, d$_6$-DMSO) δ: 7.55 (m, 1H) 7.22-7.18 (m, 2H), 7.14 (d, 1H, J 3.0 Hz), 7.03 (dd, 1H, J 8.9, 3.0 Hz), 6.93 (d, 1H, J 8.9 Hz), 5.84 (dd, 1H, J 14.0, 3.0 Hz), 3.38 (dd, 1H, J −17.0, 14.0 Hz), 2.80 (dd, 1H, J −17.0, 3.0 Hz).

2-(3,5-Difluorophenyl)-6-hydroxychroman-4-one $^1$H NMR (400 MHz, d$_6$-DMSO) δ: 9.47 (s, 1H), 7.30-7.23 (m, 3H), 7.12 (d, 1H, J 2.9 Hz), 7.06 (dd, 1H, J 8.8, 2.9 Hz), 7.00 (d, 1H, J 8.8 Hz), 5.60 (dd, 1H, J 13.1, 2.8 Hz), 3.15 (dd, 1H, J −16.8, 13.1 Hz), 2.85 (dd, 1H, J −16.8, 2.8 Hz).

6-Hydroxy-2-(2-trifluoromethylphenyl)chroman-4-one $^1$H NMR (300 MHz, d$_6$-DMSO) δ: 9.48 (s, 1H), 8.07 (m, 1H,) 7.86-7.79 (m, 2H), 7.66 (m, 1H), 7.15 (d, 1H, J 3.0 Hz), 7.06 (dd, 1H, J 8.8, 3.0 Hz), 6.95 (d, 1H, J 8.8 Hz), 5.70 (dd, 1H, J 13.8, 2.4 Hz), 3.38 (dd, 1H, J −16.9, 13.8 Hz), 2.66 (dd, 1H, J −16.9, 3.0 Hz).

6-Hydroxy-2-(4-trifluoromethylphenyl)chroman-4-one $^1$H NMR (400 MHz, d$_6$-DMSO) δ: 9.47 (s, 1H), 7.82-7.76 (m, 4H), 7.13 (d, 1H, J 3.0 Hz), 7.06 (dd, 1H, J 8.8, 3.0 Hz), 6.99 (d, 1H, J 8.8 Hz), 5.70 (dd, 1H, J 12.9, 2.9 Hz), 3.16 (dd, 1H, J −16.9, 12.9 Hz), 2.86 (dd, 1H, J −16.9, 2.9 Hz).

2-(3-Chloro-4-fluorophenyl)-6-hydroxychroman-4-one $^1$H NMR (400 MHz, d$_6$-DMSO) δ: 9.45 (s, 1H), 7.53 (m, 1H), 7.36-7.31 (m, 2H), 7.13 (d, 1H, J 3.0 Hz), 7.05 (dd, 1H, J 8.9, 3.0 Hz), 6.96 (d, 1H, J 8.9 Hz), 5.76 (dd, 1H, J 13.5, 2.7 Hz), 3.26 (dd, 1H, J −16.9, 13.5 Hz), 2.75 (dd, 1H, J −16.9, 2.7 Hz).

2-(2-Chlorophenyl)-6-hydroxychroman-4-one $^1$H NMR (400 MHz, d$_6$-DMSO) δ: 9.49 (s, 1H), 7.77 (dd, 1H, J 7.7, 2.0 Hz), 7.53 (dd, 1H, J 7.6, 1.8 Hz), 7.49-7.41 (m, 2H), 7.14 (d, 1H, J 2.9 Hz), 7.06 (dd, 1H, J 8.8, 2.9 Hz), 6.93 (d, 1H, J 8.8 Hz), 5.78 (dd, 1H, J 13.6, 2.6 Hz), 3.19 (dd, 1H, J −16.9, 13.6 Hz), 2.78 (dd, 1H, J −16.9, 2.6 Hz).

2-(3-Chlorophenyl)-6-hydroxychroman-4-one $^1$H NMR (400 MHz, d$_6$-DMSO) δ: 9.47 (s, 1H), 7.62 (s, 1H), 7.51-7.45 (m, 3H), 7.12 (d, 1H, J 3.0 Hz), 7.05 (dd, 1H, J 8.8, 3.0 Hz), 6.98 (d, 1H, J 8.8 Hz), 5.58 (dd, 1H, J 13.1, 2.9 Hz), 3.18 (dd, 1H, J −16.9, 13.1 Hz), 2.81 (dd, 1H, J −16.9, 2.9 Hz).

2-(2,4-Dichlorophenyl)-6-hydroxychroman-4-one $^1$H NMR (400 MHz, d$_6$-DMSO) δ: 9.49 (s, 1H), 7.78 (d, 1H, J 8.5 Hz), 7.71(d, 1H, J 2.0 Hz)), 7.57 (dd, 1H, J 8.5, 2.0 Hz), 7.14 (d, 1H, J 3.0 Hz), 7.06 (dd, 1H, J 8.8, 3.0 Hz), 6.97 (d, 1H, J 8.8 Hz), 5.77 (dd, 1H, J 13.5, 2.7 Hz), 3.18 (dd, 1H, J −16.9, 13.5 Hz), 2.78 (dd, 1H, J −16.9, 2.7 Hz).

2-(3-Bromophenyl)-6-hydroxychroman-4-one $^1$H NMR (300 MHz, d$_6$-DMSO) δ: 9.41 (s, 1H), 7.50 (m, 1H), 7.59-7.53 (m, 2H), 7.39 (m, 1H) 7.12 (d, 1H, J 2.9 Hz), 7.05 (dd, 1H, J 8.8, 2.9 Hz), 6.98 (d, 1H, J 8.8 Hz), 5.57 (dd, 1H, J 13.0, 2.9 Hz), 3.12 (dd, 1H, J −16.9, 13.0 Hz), 2.81 (dd, 1H, J −16.9, 2.9 Hz).

2-(4-Ethylphenyl)-6-hydroxychroman-4-one $^1$H NMR (400 MHz, d$_6$-DMSO) δ: 7.43 (d, 2H, J 8.1 Hz), 7.25 (d, 2H, J 8.1 Hz), 7.11 (d, 1H, J 3.1 Hz), 7.03 (dd, 1H, J 8.9, 3.1 Hz), 6.93 (d, 1H, J 8.9 Hz), 5.51 (dd, 1H, J 13.0, 2.9 Hz), 3.15 (dd, 1H, J −16.9, 13.0 Hz), 2.75 (dd, 1H, J −16.9, 2.9 Hz), 2.62 (q, 2H, J 7.5 Hz), 1.18 (t, 3H, J 7.5 Hz).

6-Hydroxy-2-(2-nitrophenyl)chroman-4-one $^1$H NMR (400 MHz, d$_6$-DMSO) δ: 9.49 (s, 1H), 8.05-8.06 (m, 1H), 7.96-7.98 (m, 1H), 7.83-7.87 (m, 1H), 7.65-7.69 (m, 1H), 7.14 (d, 1H, J 3.1 Hz), 7.05 (dd, 1H, J 8.8, 3.1 Hz), 6.91 (d, 1H, J 8.8 Hz), 5.69 (dd, 1H, J 13.0, 2.6 Hz), 3.22 (dd, 1H, J 16.8, 13.0 Hz), 2.98 (dd, 1H, J 16.8, 2.6 Hz).

6-Hydroxy-2-(3-nitrophenyl)chroman-4-one $^1$H NMR (300 MHz, d$_6$-DMSO) δ: 8.40 (s, 1H), 8.24 (dd, 1H, J 8.2, 2.3 Hz), 8.01 (d, 1H, J 7.9 Hz), 7.74 (t, 1H, J 15.9, 7.9 Hz), 7.13 (d, 1H, J 2.9 Hz), 7.07 (dd, 1H, J 8.8, 2.9 Hz), 7.00 (d, 1H, 8.8 Hz), 5.75 (dd, 1H, J 13.1, 2.9 Hz), 3.21 (dd, 1H, J 16.8, 13.1 Hz), 2.88 (dd, 1H, J 16.8, 2.9 Hz).

6-Hydroxy-2-(4-nitrophenyl)chroman-4-one $^1$H NMR (400 MHz, d$_6$-DMSO) δ: 9.48 (s, 1H), 8.29 (d, 2H, J 6.9 Hz), 7.83 (d, 2H, J 6.9 Hz), 7.13 (d, 1H J 2.9 Hz), 7.06 (dd, 1H, J 8.8, 2.9 Hz), 7.01 (d, 1H, J 8.8 Hz), 5.77 (dd, 1H, J 13.0, 3.0 Hz), 3.15 (dd, 1H, J 16.8, 13.0 Hz), 2.89 (dd, 1H, J 16.8, 3.0 Hz).

6-Hydroxy-2-(3-methoxyphenyl)chroman-4-one $^1$H NMR (400 MHz, d$_6$-DMSO) δ: 9.42 (s, 1H), 7.33 (t, 1H, J 15.8, 8.3 Hz), 7.12 (d, 1H, J 3.0 Hz), 7.10 (s, 1H), 7.09 (d, 1H, J 8.3 Hz), 7.04 (dd, 1H, J 8.8, 3.0 Hz), 6.96 (d, 1H, 8.8 Hz), 6.93 (dd, 1H, J 8.0, 2.5 Hz), 5.52 (dd, 1H, J 12.9, 2.9 Hz), 3.77 (s, 3H), 3.17 (dd, 1H, J 16.9, 12.9 Hz), 2.77 (dd, 1H, J 16.9, 2.9 Hz).

6-Hydroxy-3-methyl-2-phenylchroman-4-one $^1$H NMR (300 MHz, d$_6$-DMSO) δ: 9.37 (s, 1H), 7.53 (m, 2H), 7.47-7.39 (m, 3H), 7.13 (d, 1H, J 3.1 Hz), 7.02 (dd, 1H, J 8.9, 3.1 Hz), 6.89(d, 1H, J 8.9 Hz), 5.17 (d, 1H, J 12.3), 3.18 (dq, 1H, J 12.3, 6.9 Hz), 0.84 (d, 3H, J 6.9 Hz).

b) Chroman-4,6-diol Intermediates 2-(4-Fluorophenyl)chroman-4,6-diol

Into a suspension of 2-(4-fluorophenyl)-6-hydroxychroman-4-one (3.4 g) in dry THF (34 ml) was added dropwise a solution of borane-THF complex (20 ml, 1.0 M in THF) under nitrogen. The reaction mixture was refluxed for 1 hour. After cooling to the room temperature it was poured into an ice-2 M HCl-solution. 2-(4-Fluorophenyl)chroman-4,6-diol was filtered. $^1$H NMR (400 MHz, $d_6$-DMSO) δ: 8.84 (s, 1H), 7.48 (m, 2H), 7.21 (m, 2H), 6.89 (d, 1H, J 2.7 Hz), 6.59 (d, 1H, J 8.7 Hz), 6.54 (dd, 1H, J 8.7, 2.7 Hz), 5.42 (bs, 1H), 5.12 (d, 1H, J 10.7 Hz), 4.87 (m, 1H), 2.25 (m, 1H), 1.89 (m, 1H).

Using the same procedure as described above for 2-(4-fluorophenyl)chroman-4,6-diol, but replacing 2-(4-fluorophenyl)-6-hydroxychroman-4-one by an appropriate 2-phenyl-6-hydroxychroman-4-one, there was obtained:

2-(3-Fluorophenyl)chroman-4,6-diol $^1$H NMR (400 MHz, $d_6$-DMSO) δ: 8.85 (s, 1H), 7.45 (m, 1H), 7.30-7.25 (m, 2H), 7.15 (m, 1H), 6.88 (d, 1H, J 2.8 Hz), 6.62 (d, 1H, J 8.7 Hz), 6.55 (dd, 1H, J 8.7, 2.8 Hz), 5.44 (d, 1H, J 7.0 Hz), 5.15 (d, 1H, J 10.7 Hz), 4.86 (m, 1H), 2.29 (m, 1H), 1.86 (m, 1H).

2-(2-Fluorophenyl)chroman-4,6-diol $^1$H NMR (400 MHz, $d_6$-DMSO) δ: 8.85 (s, 1H), 7.56 (m, 1H), 7.40 (m, 1H), 7.28-7.21 (m, 2H), 6.89 (d, 1H, J 2.9 Hz), 6.60 (d, 1H, J 8.7 Hz), 6.54 (dd, 1H, J 8.7, 2.8 Hz), 5.46 (d, 1H, J 6.9 Hz), 5.35 (d, 1H, J 10.6 Hz), 4.89 (m, 1H), 2.26 (m, 1H), 1.98 (m, 1H).

2-(2,3-Difluorophenyl)chroman-4,6-diol $^1$H NMR (400 MHz, $d_6$-DMSO) δ: 8.88 (s, 1H), 7.45-7.36 (m, 2H), 7.28 (m, 1H), 6.89 (d, 1H, J 2.8 Hz), 6.61 (d, 1H, J 8.7 Hz), 6.55 (dd, 1H, J 8.7, 2.8 Hz), 5.49 (bs, 1H), 5.40 (dd, 1H, J 11.8, 1.4 Hz), 4.90 (m, 1H), 2.28 (m, 1H), 1.99 (m, 1H).

2-(2,4-Difluorophenyl)chroman-4,6-diol $^1$H NMR (400 MHz, $d_6$-DMSO) δ: 8.86 (s, 1H), 7.61 (m, 1H), 7.28 (m, 1H), 7.14 (m, 1H), 6.88 (d, 1H, J 2.7 Hz), 6.59 (d, 1H, J 8.9 Hz), 6.54 (dd, 1H, J 8.9, 2.7 Hz), 5.46 (s, 1H), 5.32 (dd, 1H, J 11.9, 1.4 Hz), 4.88 (m, 1H), 2.24 (m, 1H), 1.99 (m, 1H).

2-(2,5-Difluorophenyl)chroman-4,6-diol $^1$H NMR (400 MHz, $d_6$-DMSO) δ: 8.87 (s, 1H), 7.39-7.22 (m, 3H), 6.89 (d, 1H, J 2.8 Hz), 6.63 (d, 1H, J 8.7 Hz), 6.56 (dd, 1H, J 8.7, 2.8 Hz), 5.50 (d, 1H, J 6.8 Hz), 5.35 (d, 1H, J 11.2 Hz), 4.89 (m, 1H), 2.28 (m, 1H), 1.95 (m, 1H).

2-(2,6-Difluorophenyl)chroman-4,6-diol $^1$H NMR (400 MHz, $d_6$-DMSO) δ: 8.87 (s, 1H), 7.48 (m, 1H), 7.17-7.13 (m, 2H), 6.90 (d, 1H, J 2.9 Hz), 6.55-6.54 (m, 2H), 5.46 (dd, 1H, J 12.2, 1.8 Hz), 4.87 (m, 1H), 2.37 (m, 1H), 2.23 (m, 1H).

2-(3,5-Difluorophenyl)chroman-4,6-diol $^1$H NMR (400 MHz, $d_6$-DMSO) δ: 8.87 (s, 1H), 7.21-7.17 (m, 3H), 6.88 (d, 1H, J 2.4 Hz), 6.64 (d, 1H, J 8.7 Hz), 6.55 (dd, 1H, J 2.4, 8.7 Hz), 5.47 (d, 1H, J 7.0 Hz), 5.17 (d, 1H, J 10.5 Hz), 4.86 (m, 1H), 2.32 (m, 1H), 1.85 (m, 1H).

2-(2-Trifluoromethylphenyl)chroman-4,6-diol $^1$H NMR (300 MHz, $d_6$-DMSO) δ: 8.89 (s, 1H), 7.83 (m, 1H), 7.79-7.74 (m, 2H), 7.58 (m, 1H), 6.90 (d, 1H, J 2.7 Hz), 6.61 (d, 1H, J 8.9 Hz), 6.56 (dd, 1H, J 8.7, 2.7 Hz), 5.51 (d, 1H, J 6.5 Hz), 5.34 (d, 1H, J 11.6 Hz), 4.88 (m, 1H), 2.21 (m, 1H), 1.95 (m, 1H).

2-(4-Trifluoromethylphenyl)chroman-4,6-diol $^1$H NMR (400 MHz, $d_6$-DMSO) δ: 8.86 (s, 1H), 7.77 (d, 2H, J 8.3 Hz), 7.68 (d, 2H, J 8.3 Hz), 6.89 (d, 1H, J 2.9 Hz), 6.63 (d, 1H, J 8.7 Hz), 6.56 (dd, 1H, J 8.7, 2.9 Hz), 5.45 (d, 1H, J 7.0 Hz), 5.26 (d, 1H, J 11.2 Hz), 4.90 (m, 1H), 2.32 (m, 1H), 1.85 (m, 1H).

2-(3-Chloro-4-fluorophenyl)chroman-4,6-diol $^1$H NMR (400 MHz, $d_6$-DMSO) δ: 8.88 (s, 1H), 7.39-7.24 (m, 3H), 6.88 (d, 1H, J 2.8 Hz), 6.63 (d, 1H, J 8.7 Hz), 6.55 (dd, 1H, J 8.7, 2.8 Hz), 5.49 (d, 1H, J 6.8 Hz), 5.35 (d, 1H, J 11.3 Hz), 4.89 (m, 1H), 2.39 (m, 1H), 1.97 (m, 1H).

2-(2-Chlorophenyl)chroman-4,6-diol $^1$H NMR (400 MHz, $d_6$-DMSO) δ: 7.63 (dd, 1H, J 7.7, 1.8 Hz), 7.49 (dd, 1H, J 7.8, 1.4 Hz), 7.45-7.36 (m, 2H), 6.89 (d, 1H, J 2.9 Hz), 6.63 (d, 1H, J 8.8 Hz), 6.56 (dd, 1H, J 8.9, 2.9 Hz), 5.39 (dd, 1H, J 11.7, 1.5 Hz), 4.90 (m, 1H), 2.33 (m, 1H), 1.82 (m, 1H).

2-(3-Chlorophenyl)chroman-4,6-diol $^1$H NMR (400 MHz, $d_6$-DMSO) δ: 8.85 (s, 1H), 7.50 (d, 1H, J 1.7 Hz), 7.46-7.38 (m, 3H), 6.88 (d, 1H, J 2.5 Hz), 6.62 (d, 1H, J 8.6 Hz), 6.55 (dd, 1H, J 8.6, 2.5 Hz), 5.44 (d, 1H, J 6.6 Hz), 5.15 (dd, 1H, J 11.8, 1.4 Hz), 4.87 (m, 1H), 2.29 (m, 1H), 1.85 (m, 1H).

2-(2,4-Dichlorophenyl)chroman-4,6-diol $^1$H NMR (400 MHz, $d_6$-DMSO) δ: 8.89 (s, 1H), 7.66 (d, 1H, J 2.1 Hz), 7.64 (d, 1H, J 8.5 Hz), 7.51 (dd, 1H, J 2.1, 8.5 Hz), 6.89 (d, 1H, J 2.7 Hz), 6.63 (d, 1H, J 8.7 Hz), 6.56 (dd, 1H, J 2.7, 8.7 Hz), 5.50 (d, 1H, J 6.8 Hz), 5.37 (d, 1H, J 10.4 Hz), 4.90 (m, 1H), 2.32 (m, 1H), 1.80 (m, 1H).

2-(3-Bromophenyl)-chroman-4,6-diol $^1$H NMR (300 MHz, $d_6$-DMSO) δ: 8.83 (s, 1H), 7.63 (m, 1H) 7.53 (m, 1H) 7.46 (m, 1H) 7.37 (m, 1H), 6.88 (d, 1H, J 2.9 Hz), 6.62 (d, 1H, J 8.7 Hz), 6.55 (dd, 1H, J 8.7, 2.9 Hz), 5.42 (d, 1H, J 7.0 Hz), 5.14 (d, 1H, J 10.5 Hz), 4.86 (m, 1H), 2.29 (m, 1H), 1.84 (m, 1H).

2-(4-Ethylphenyl)chroman-4,6-diol $^1$H NMR (400 MHz, $d_6$-DMSO) δ: 8.81 (s, 1H), 7.34 (d, 2H, J 8.0 Hz) 7.22 (d, 2H, J 8.0 Hz), 6.88 (d, 1H, J 2.8 Hz), 6.57 (d, 1H, J 8.6 Hz), 6.53 (dd, 1H, J 8.6, 2.8 Hz), 5.39 (d, 1H, J 7.1 Hz), 5.06 (d, 1H, J 10.7 Hz), 4.86 (m, 1H), 2.61 (q, 2H, J 7.6 Hz), 2.29 (m, 1H), 1.84 (m, 1H), 1.19 (t, 3H, J 7.6 Hz).

2-(2-Nitrophenyl)chroman-4,6-diol $^1$H NMR (300 MHz, $d_6$-DMSO) δ: 8.87 (s, 1H), 7.99-8.02 (m, 1H), 7.77-7.86 (m, 2H), 7.59-7.64 (m, 1H), 6.89 (d, 1H, J 2.4 Hz), 6.56-6.57 (m, 2H), 5.51-5.55 (m, 2H), 4.85-4.92 (m, 1H), 2.42-2.47 (m, 1H), 1.85-1.96 (m, 1H).

2-(3-Nitrophenyl)chroman-4,6-diol $^1$H NMR (400 MHz, d$_6$-DMSO) δ: 8.89 (br s, 1H), 8.29 (s, 1H), 8.20 (dd, 1H, J 8.2, 2.3 Hz), 7.93 (d, 1H, J 7.9 Hz), 7.71 (t, 1H, J 15.9, 7.9 Hz), 6.89 (d, 1H, J 2.8 Hz), 6.66 (d, 1H, J 8.7 Hz), 6.57 (dd, 1H, J 8.7, 2.9 Hz), 5.47 (br s, 1H), 5.33 (d, 1H, J 10.7 Hz), 4.88-4.92 (m, 1H), 2.33-2.39 (m, 1H), 1.83-1.92 (m, 1H).

2-(4-Nitrophenyl)chroman-4,6-diol $^1$H NMR (300 MHz, d$_6$-DMSO) δ: 8.86 (s, 1H), 8.26 (d, 2H, J 6.9 Hz), 7.74 (d, 2H, J 6.9 Hz), 6.89 (d, 1H J 2.8 Hz), 6.65 (d, 1H, J 8.6 Hz), 6.56 (dd, 1H, J 8.6, 2.8 Hz), 5.46 (d, 1H, J 6.9 Hz), 5.32 (d, 1H, J 10.5 Hz), 4.86-4.94 (m, 1H), 2.31-2.38 (m, 1H), 1.78-1.89 (m, 1H).

2-(3-methoxyphenyl)chroman-4,6-diol $^1$H NMR (400 MHz, d$_6$-DMSO) δ: 8.82 (s, 1H), 7.31 (t, 1H, J 15.7, 7.9 Hz), 6.99-7.02 (m, 2H), 6.88-6.90 (m, 2H), 6.59 (d, 1H, J 8.7 Hz), 6.54 (dd, 1H, J 8.7, 2.8 Hz), 5.40 (d, 1H, J 7.0 Hz), 5.08 (d, 1H, J 11.5 Hz), 4.83-4.89 (m, 1H), 3.77 (s, 3H), 2.23-2.28 (m, 1H), 1.83-1.92 (m, 1H).

3-Methyl-2-phenylchroman-4,6-diol $^1$H NMR (300 MHz, d$_6$-DMSO) δ: 8.79 (s, 1H), 7.42-7.33 (m, 5H), 6.88 (bs, 1H,), 6.53 (m, 2H), 5.37 (d, 1H, J 8.0 Hz), 4.70 (d, 1H, J 10.6 Hz), 1.94 (m, 1H), 0.73 (d, 3H, J 6.7 Hz).

c) Chroman-6-ol Intermediates 2-(4-Fluorophenyl)chroman-6-ol

Triethylsilane (14 ml) was added slowly into a solution of 2-(4-fluorophenyl)chroman-4,6-diol (2.9 g) in dichloromethane (58 ml). Trifluoroacetic acid (27 ml) was then added dropwise into a reaction mixture and it was stirred at room temperature for 1 hour. The reaction mixture was poured on ice-water and extracted with dichloromethane. The residue was evaporated under reduced pressure with toluene to obtain 2-(4-fluorophenyl)chroman-6-ol. $^1$H NMR (400 MHz, CDCl$_3$) δ: 7.38 (m, 2H), 7.06 (m, 2H), 6.77 (d, 1H, J 8.6 Hz), 6.61 (dd, 1H, J 8.6, 2.9 Hz) 6.57 (d, 1H, 8.6 Hz), 4.97 (dd, 1H, J 10.2, 2.4 Hz), 2.95 (ddd, 1H, J −16.8, 11.4, 6.2 Hz), 2.74 (ddd, 1H, J −16.8, 5.3, 3.1 Hz), 2.15 (m, 1H), 2.05 (m, 1H).

Using the same procedure as described above for 2-(4-fluorophenyl)chroman-6-ol, but replacing 2-(4-fluorophenyl)chroman-4,6-diol by an appropriate 2-phenylchroman-4,6-diol, there was obtained:

2-(3-Fluorophenyl)chroman-6-ol $^1$H NMR (400 MHz, d$_6$-DMSO) δ: 8.78 (s, 1H), 7.43 (m, 1H), 7.28-7.25 (m, 2H), 7.14 (m, 1H), 6.66 (d, 1H, J 8.5 Hz) 6.52 (dd, 1H, J 8.5, 2.7 Hz), 6.49 (d, 1H, J 2.7 Hz), 5.03 (dd, 1H, J 9.9, 2.1 Hz), 2.86 (m, 1H), 2.63 (m, 1H) 2.13 (m, 1H), 1.93 (m, 1H).

2-(2-Fluorophenyl)chroman-6-ol $^1$H NMR (300 MHz, d$_6$-DMSO) δ: 7.50 (m, 1H), 7.39 (m, 1H), 7.26-7.19 (m, 2H), 6.63 (m, 1H) 6.53-6.50 (m, 2H), 5.21 (dd, 1H, J, 10.2, 2.3 Hz), 2.98 (ddd, 1H, J −16.9, 11.2, 6.0 Hz), 2.66 (ddd, 1H, J −16.9, 5.0, 2.9 Hz) 2.11 (m, 1H), 1.99 (m, 1H).

2-(2,3-Difluorophenyl)chroman-6-ol $^1$H NMR (400 MHz, d$_6$-DMSO) δ: 8.85 (s, 1H), 7.41 (m, 1H), 7.33 (m, 1H), 7.26 (m, 1H), 6.64 (dd, 1H, 9.0, 2.8 Hz), 6.54-6.51 (m, 2H), 5.25 (dd, 1H, J 10.2, 2.2 Hz), 2.93 (m, 1H), 2.66 (m, 1H), 2.14 (m, 1H), 2.01 (m, 1H).

2-(2,4-Difluorophenyl)chroman-6-ol $^1$H NMR (400 MHz, d$_6$-DMSO) δ: 8.83 (s, 1H), 7.56 (m, 1H), 7.28 (m, 1H), 7.13 (m, 1H), 6.63 (m, 1H), 6.53-6.50 (m, 2H), 5.17 (dd, 1H, J 10.3, 2.3 Hz), 2.92 (ddd, 1H, J −17.0, 11.5, 5.8 Hz), 2.66 (ddd, 1H, J −17.0, 5.0, 2.7 Hz), 2.09 (m, 1H), 1.98 (m, 1H).

2-(2,5-Difluorophenyl)chroman-6-ol $^1$H NMR (300 MHz, d$_6$-DMSO) δ: 8.82 (s, 1H), 7.34-7.22 (m, 3H), 6.71-6.51 (m, 3H), 5.20 (m, 1H), 2.93 (m, 1H,), 2.68 (m, 1H), 2.11 (m, 1H), 1.98 (m, 1H).

2-(2,6-Difluorophenyl)chroman-6-ol $^1$H NMR (300 MHz, d$_6$-DMSO) δ: 8.85 (s, 1H), 7.41 (m, 1H), 7.33 (m, 1 h), 7.26 (m, 1H), 6.64 (dd, 1H, J 9.0, 2.8 Hz), 6.54-6.51 (m, 2H), 5.25 (dd, 1H, J 10.2, 2.2 Hz), 2.93 (m, 1H,), 2.66 (m, 1H), 2.14 (m, 1H), 2.01 (m, 1H).

2-(3,5-Difluorophenyl)chroman-6-ol $^1$H NMR (300 MHz, d$_6$-DMSO) δ: 8.82 (s, 1H), 7.20-7.14 (m, 3H), 6.68 (d, 1H, J 8.6 Hz), 6.53 (d, 1H, J 2.9 Hz), 6.50 (dd, 1H, J 8.6, 2.9 Hz), 5.05 (dd, 1H, J 9.8, 2.2 Hz), 2.88 (ddd, 1H, J −16.7, 10.8, 5.9 Hz), 2.62 (ddd, 1H, J −16.7, 8.9, 5.0 Hz), 2.15 (m, 1H), 1.93 (m, 1H).

2-(2-Trifluoromethylphenyl)chroman-6-ol $^1$H NMR (400 MHz, d$_6$-DMSO) δ: 8.86 (s, 1H), 7.81-7.75 (m, 3H), 7.57 (m, 1H), 6.674 (dd, 1H, J 7.1, 2.1 Hz), 6.54-6.51 (m, 2H), 5.14 (d, 1H, J 10.5 Hz), 2.95 (m, 1H), 2.72 (m, 1H), 2.05 (m, 1H), 1.96 (m, 1H).

2-(4-Trifluoromethylphenyl)chroman-6-ol $^1$H NMR (400 MHz, d$_6$-DMSO) δ: 8.82 (s, 1H), 7.75 (d, 2H, J 8.3 Hz), 7.65 (d, 2H, J 8.3 Hz), 6.67 (d, 1H, J 8.6 Hz), 6.53 (d, 1H, J 2.9 Hz) 6.51 (dd, 1H, 8.6, 2.9 Hz), 5.12 (d, 1H, J 8.3 Hz), 2.90 (m, 1H), 2.63 (m, 1H), 2.16 (m, 1H), 1.92 (m, 1H).

2-(3-Chloro-4-fluorophenyl)chroman-6-ol $^1$H NMR (400 MHz, d$_6$-DMSO) δ: 8.84 (s, 1H), 7.33-7.21 (m, 3H), 6.66 (d, 1H, J 8.3 Hz) 6.54-6.51 (m, 2H), 5.19 (d, 1H, J, 8.8 Hz), 2.92 (m, 1H), 2.66 (m, 1H) 2.12 (m, 1H), 1.96 (m, 1H).

2-(2-Chlorophenyl)chroman-6-ol $^1$H NMR (300 MHz, d$_6$-DMSO) δ: 7.58-7.36 (m, 4H), 6.66 (m, 1H), 6.55-6.51 (m, 2H), 5.23 (dd, 1H, J 10.1, 2.1 Hz), 2.92 (m, 1H), 2.68 (m, 1H), 2.17 (m, 1H), 1.87 (m, 1H).

2-(3-Chlorophenyl)chroman-6-ol $^1$H NMR (300 MHz, d$_6$-DMSO) δ: 8.79 (s, 1H), 7.48 (d, 1H, J 0.7 Hz), 7.42-7.37 (m, 3H), 6.71-6.49 (m, 3H), 5.04 (m, 1H), 2.91 (m, 1H), 2.65 (m, 1H), 2.12 (m, 1H), 1.93 (m, 1H).

2-(2,4-Dichlorophenyl)chroman-6-ol $^1$H NMR (400 MHz, d$_6$-DMSO) δ: 8.85 (s, 1H), 7.65 (d, 1H, J 2.2 Hz), 7.57 (d, 1H, J 8.4 Hz), 7.49 (dd, 1H, J 8.4, 2.2 Hz), 6.67-6.51 (m, 3H), 5.21 (dd, 1H, J 10.3, 2.1 Hz), 2.91 (m, 1H), 2.69 (m, 1H), 2.16 (m, 1H), 1.85 (m, 1H).

2-(3-Bromophenyl)chroman-6-ol $^1$H NMR (400 MHz, d$_6$-DMSO) δ: 8.81 (s, 1H), 7.61 (m, 1H), 7.51 (m, 1H), 7.43 (m, 1H), 7.35 (m, 1H) 6.67-6.48 (m, 3H), 5.01 (m, 1H), 2.87 (m, 1H,), 2.63 (m, 1H), 2.12 (m, 1H), 1.92 (m, 1H).

2-(4-Ethylphenyl)chroman-6-ol $^1$H NMR (400 MHz, CD$_3$OD) δ: 7.26 (d, 2H, J 8.2 Hz) 7.13 (d, 2H, J 8.2 Hz), 6.65 (d, 1H, J 8.6 Hz), 6.55 (dd, 1H, J 8.6, 2.8 Hz), 6.51 (d, 1H, J 2.8 Hz), 4.83 (dd, 1H, J 10.1, 2.3 Hz), 2.84 (m, 1H,), 2.62 (m, 1H), 2.59 (q, 2H, J 7.6 Hz) 2.03 (m, 1H), 1.93 (m, 1H), 1.19 (t, 3H, J 7.6 Hz).

2-(2-Nitrophenyl)chroman-6-ol $^1$H NMR (400 MHz, d$_6$-DMSO) δ: 8.85 (s, 1H), 8.00 (d, 1H, J 8.0 Hz), 7.79-7.80 (m, 2H), 7.59-7.63 (m, 1H), 6.59-6.62 (m, 1H), 6.50-6.53 (m, 2H), 5.36 (dd, 1H, J 10.2, 2.0 Hz), 2.89-2.93 (m, 1H), 2.67-2.73 (m, 1H), 2.26-2.31 (m, 1H), 1.90-1.95 (m, 1H).

2-(3-Nitrophenyl)chroman-6-ol $^1$H NMR (300 MHz, d$_6$-DMSO) δ: 8.80 (s, 1H), 8.26 (s, 1H), 8.19 (dd, 1H, J 8.1, 2.3 Hz), 7.90 (d, 1H, J 7.9 Hz), 7.70 (t, 1H, J 15.9, 7.9 Hz), 6.70 (d, 1H, J 8.4 Hz), 6.51-6.55 (m, 2H), 5.19 (dd, 1H, J 10.0, 2.0), 2.86-2.91 (m, 1H), 2.61-2.68 (m, 1H), 2.17-2.23 (m, 1H), 1.91-1.97 (m, 1H).

2-(4-Nitrophenyl)chroman-6-ol $^1$H NMR (400 MHz, d$_6$-DMSO) δ: 8.84 (s, 1H), 8.26 (d, 2H, J 6.9 Hz), 7.71 (d, 2H, J 6.9 Hz), 6.69 (d, 1H, J 8.6 Hz), 6.53 (dd, 1H, J 8.6, 2.8 Hz), 6.50 (d, 1H, J 2.8 Hz), 5.19 (dd, 1H, J 9.9, 2.2 Hz), 2.87-2.91 (m, 1H), 2.61-2.66 (m, 1H), 2.16-2.21 (m, 1H), 1.89-1.93 (m, 1H).

2-(3-Methoxyphenyl)chroman-6-ol $^1$H NMR (300 MHz, d$_6$-DMSO) δ: 8.75 (s, 1H), 7.28 (t, 1H, J 15.7, 7.9 Hz), 6.96-6.99 (m, 2H), 6.87 (dd, 1H, J 7.9, 2.5 Hz), 6.63 (d, 1H, J 8.3 Hz), 6.52 (d, 1H, J 2.9 Hz), 6.48 (s, 1H), 4.95 (dd, 1H, J 9.8, 2.2 Hz), 3.75 (s, 3H), 2.82-2.89 (m, 1H), 2.57-2.66 (m, 1H), 2.06-2.13 (m, 1H), 1.89-1.97 (m, 1H).

3-Methyl-2-phenylchroman-6-ol $^1$H NMR (400 MHz, CD$_3$OD) δ: 8.77 (s, 1H), 7.41-7.33 (m, 5H), 6.59-6.48 (m, 3H), 4.56 (d, 1H, J 9.2 Hz), 2.73 (dd, 1H, J −16.5, 5.0 Hz), 2.54 (dd, 1H, J −16.5, 5.8 Hz), 2.11 (m, 1H), 0.72 (d, 3H, J 6.6 Hz).

d) 2-[2-Phenylchroman-6-yloxy]-5-nitropyridine Intermediates

2-[2-(4-Fluorophenyl)chroman-6-yloxy]-5-nitropyridine

2-[2-(4-Fluorophenyl)chroman-6-yloxy]-5-nitropyridine was prepared as described for 5-nitro-2-(2-phenylchroman-6-yloxy)pyridine in Example 1(b) starting from 160 mg of 2-(4-fluorophenyl)chroman-6-ol. $^1$H NMR (400 MHz, d$_6$-DMSO) δ: 9.04 (dd, 1H, J 2.9, 0.4 Hz), 8.60 (dd, 1H, J 9.1, 2.9 Hz), 7.51 (m, 2H), 7.24 (m, 1H), 7.20 (dd, 1H, J 9.1, 0.4 Hz), 7.01 (d, 1H, J 2.8 Hz), 6.96 (dd, 1H, J 8.7, 2.8 Hz) 6.91 (d, 1H, 8.7 Hz), 5.15 (dd, 1H, J 10.3, 2.2 Hz), 2.94 (m, 1H), 2.76 (m, 1H) 2.17 (m, 1H), 2.01 (m, 1H).

Using the same procedure as described above for 2-[2-(4-fluorophenyl)chroman-6-yloxy]-5-nitropyridine, but replacing 2-(4-fluorophenyl)chroman-6-ol by an appropriate 2-phenylchroman-6-ol, there was obtained:

2-[2-(3-Fluorophenyl)chroman-6-yloxy]-5-nitropyridine $^1$H NMR (400 MHz, CDCl$_3$) δ: 9.07 (d, 1H, J 2.8 Hz), 8.46 (dd, 1H, J 9.0, 2.8 Hz), 7.36 (m, 1H), 7.21-7.15 (m, 2H), 7.03 (m, 1H), 7.01 (d, 1H, J 9.0 Hz), 6.98 (d, 1H, J 8.6 Hz) 6.92 (dd, 1H, J 8.6, 2.7 Hz), 6.90 (d, 1H, J 2.7 Hz), 5.09 (dd, 1H, J 10.3, 2.4 Hz), 3.01 (ddd, 1H, J −16.9, 11.4, 6.0 Hz), 2.82 (ddd, 1H, J −16.9, 5.1, 3.2 Hz) 2.24 (m, 1H), 2.09 (m, 1H).

2-[2-(2-Fluorophenyl)chroman-6-yloxy]-5-nitropyridine $^1$H NMR (400 MHz, CDCl$_3$) δ: 9.04 (d, 1H, J 2.8 Hz), 8.60 (dd, 1H, J 9.1, 2.8 Hz), 7.56 (m, 1H), 7.43 (m, 1H), 7.30-7.22 (m, 2H), 7.20 (d, 1H, J 9.1 Hz), 7.02 (d, 1H, J 2.8 Hz) 6.98 (dd, 1H, J 8.7, 2.8 Hz), 6.91 (d, 1H, J 8.7 Hz), 5.37 (dd, 1H, J 10.4, 2.3 Hz), 3.04 (ddd, 1H, J −17.0, 11.5, 6.0 Hz), 2.82 (ddd, 1H, J −17.0, 5.1, 2.8 Hz) 2.18 (m, 1H), 2.08 (m, 1H).

2-[2-(2,3-Difluorophenyl)chroman-6-yloxy]-5-nitropyridine $^1$H NMR (400 MHz, d$_6$-DMSO) δ: 9.04 (d, 1H, J 3.0 Hz), 8.60 (dd, 1H, J 9.1, 3.0 Hz), 7.45 (m, 1H), 7.38 (m, 1H), 7.30 (m, 1H), 7.21 (d, 1H, J 9.1 Hz), 7.03 (d, 1H, J 2.7 Hz), 6.98 (dd, 1H, J 8.8, 2.7 Hz), 6.92 (d, 1H, 8.8 Hz), 5.42 (dd, 1H, J 10.4, 2.3 Hz), 3.04 (m, 1H), 2.79 (m, 1H) 2.21 (m, 1H), 2.08 (m, 1H).

2-[2-(2,4-Difluorophenyl)chroman-6-yloxy]-5-nitropyridine $^1$H NMR (400 MHz, d$_6$-DMSO) δ: 9.04 (d, 1H, J 3.0 Hz), 8.60 (dd, 1H, J 9.0, 3.0 Hz), 7.61 (m, 1H), 7.31 (m, 1H), 7.21 (d, 1H, 9.0 Hz), 7.17 (m, 1H) 7.02 (d, 1H, J 2.9 Hz), 6.97 (dd, 1H, J 8.9, 2.9 Hz), 6.91 (d, 1H, 8.9 Hz), 5.34 (dd, 1H, J 9.9, 2.0 Hz), 3.03 (m, 1H), 2.78 (m, 1H) 2.17 (m, 1H), 2.07 (m, 1H).

2-[2-(2,5-Difluorophenyl)chroman-6-yloxy]-5-nitropyridine $^1$H NMR (400 MHz, CDCl$_3$) δ: 9.07 (dd, 1H, J 2.8, 0.4 Hz), 8.47 (dd, 1H, J 9.1, 2.8 Hz), 7.26 (m, 1H), 7.05-6.91 (m, 6H), 5.35 (dd, 1H, J 10.3, 1.5 Hz), 3.04 (ddd, 1H, J −16.9, 11.7, 6.0 Hz), 2.82 (ddd, 1H, J −16.9, 5.2, 3.0 Hz) 2.29 (m, 1H), 2.01 (m, 1H).

2-[2-(2,6-Difluorophenyl)chroman-6-yloxy]-5-nitropyridine

¹H NMR (400 MHz, CDCl₃) δ: 9.04 (d, 1H, J 3.0 Hz), 8.60 (dd, 1H, J 9.1, 3.0 Hz), 7.45 (m, 1H), 7.38 (m, 1H), 7.30 (m, 1H), 7.21 (d, 1H, J 9.1 Hz), 7.03 (d, 1H, J 2.7 Hz), 6.98 (dd, 1H, J 8.8, 2.7 Hz) 6.92 (d, 1H, J 8.8 Hz), 5.42 (dd, 1H, J 10.4, 2.3 Hz), 3.04 (m, 1H), 2.79 (m, 1H) 2.21 (m, 1H), 2.08 (m, 1H).

2-[2-(3,5-Difluorophenyl)chroman-6-yloxy]-5-nitropyridine

¹H NMR (400 MHz, d₆-DMSO) δ: 9.04 (d, 1H, J 2.9 Hz), 8.60 (dd, 1H, J 9.1, 2.9 Hz), 7.23-7.19 (m, 4H), 7.01-6.95 (m, 3H), 5.18 (dd, 1H, J 10.0, 2.1 Hz), 2.97 (ddd, 1H, J −16.9, 10.9, 5.7 Hz), 2.76 (ddd, 1H, J −16.9, 8.4, 4.7 Hz) 2.22 (m, 1H), 1.99 (m, 1H).

2-[2-(2-Trifluoromethylphenyl)chroman-6-yloxy]-5-nitropyridine

¹H NMR (300 MHz, d₆-DMSO) δ: 9.04 (d, 1H, J 2.9 Hz), 8.60 (dd, 1H, J 9.2, 2.9 Hz), 7.86-7.76 (m, 3H), 7.60 (m, 1H), 7.22 (d, 1H, J 9.2 Hz) 7.05 (d, 1H, J 2.7 Hz), 6.99 (dd, 1H, J 8.7, 2.7 Hz), 6.91 (d, 1H, 8.7 Hz), 5.30 (d, 1H, J 10.0, Hz), 3.05 (m, 1H), 2.84 (m, 1H) 2.16-2.00 (m, 2H).

2-[2-(4-Trifluoromethylphenyl)chroman-6-yloxy]-5-nitropyridine

¹H NMR (400 MHz, d₆-DMSO) δ: 9.04 (d, 1H, J 2.9 Hz), 8.60 (dd, 1H, J 9.1, 2.9 Hz), 7.79 (d, 2H, J 8.2 Hz), 7.70 (d, 1H, J 8.2 Hz), 7.21 (d, 1H, J 9.1 Hz) 7.01 (dd, 1H, J 8.7, 2.7 Hz) 6.98 (d, 1H, J 2.7 Hz), 6.95 (d, 1H, J 8.7 Hz), 5.29 (dd, 1H, J 10.1, 2.0 Hz), 3.00 (ddd, 1H, J −16.9, 10.1, 5.8 Hz), 2.4 (ddd, 1H, J −16.9, 8.4, 4.5 Hz) 2.24 (m, 1H), 1.99 (m, 1H).

2-[2-(3-Chloro-4-fluorophenyl)chroman-6-yloxy]-5-nitropyridine

¹H NMR (400 MHz, d₆-DMSO) δ: 9.04 (d, 1H, J 2.9 Hz), 8.60 (dd, 1H, J 9.1, 2.9 Hz), 7.40-7.27 (m, 3H), 7.21 (d, 1H, J 9.1 Hz), 7.03 (d, 1H, J 2.7 Hz) 6.98 (dd, 1H, J 8.8, 2.7 Hz), 6.94 (d, 1H, J 8.8 Hz), 5.36 (dd, 1H, J 10.7, 2.1 Hz), 3.04 (m, 1H), 2.80 (m, 1H) 2.18 (m, 1H), 1.99 (m, 1H).

2-[2-(2-Chlorophenyl)chroman-6-yloxy]-5-nitropyridine

¹H NMR (400 MHz, d₆-DMSO) δ: 9.04 (d, 1H, J 2.9, 0.5 Hz), 8.60 (dd, 1H, J 9.1, 2.9 Hz), 7.62 (dd, 1H, J 7.5, 1.8 Hz), 7.51 (dd, 1H, J 7.6, 1.7 Hz), 7.45-7.40 (m, 2H), 7.21 (dd, 1H, J 9.1, 0.5 Hz), 7.04 (d, 1H, J 2.7 Hz), 6.99 (dd, 1H, J 8.8, 2.7 Hz), 6.94 (d, 1H, 8.8 Hz), 5.40 (dd, 1H, J 10.4, 2.1 Hz), 3.04 (m, 1H), 2.80 (m, 1H) 2.24 (m, 1H), 1.95 (m, 1H).

2-[2-(3-Chlorophenyl)chroman-6-yloxy]-5-nitropyridine

¹H NMR (400 MHz, CDCl₃) δ: 9.04 (d, 1H, J 2.9 Hz), 8.60 (dd, 1H, J 9.0, 2.9 Hz), 7.53 (s, 1H), 7.46-7.42 (m, 3H), 7.20 (d, 1H, J 9.0 Hz) 7.00 (dd, 1H, J 8.7, 2.7 Hz), 6.97 (d, 1H, J 2.7 Hz), 6.94 (d, 1H, J 8.7 Hz), 5.18 (dd, 1H, J 10.2, 2.2 Hz), 2.97 (ddd, 1H, J −17.0, 11.5, 5.9 Hz), 2.83 (ddd, 1H, J −17.0, 8.1, 4.5 Hz) 2.21 (m, 1H), 2.00 (m, 1H).

2-[2-(2,4-Dichlorophenyl)chroman-6-yloxy]-5-nitropyridine

¹H NMR (400 MHz, CDCl₃) δ: 9.06 (d, 1H, J 2.7 Hz), 8.47 (dd, 1H, J 9.0, 2.7 Hz), 7.56 (d, 1H, J 8.4 Hz), 7.41 (d, 1H, J 2.0 Hz), 7.33 (dd, 1H, J 8.4, 2.0 Hz) 7.02 (d, 1H, J 9.0 Hz) 6.99-6.92 (m, 3H), 5.39 (dd, 1H, J 10.4, 2.2 Hz), 3.06 (ddd, 1H, J −16.9, 11.9, 6.0 Hz), 2.83 (ddd, 1H, J −16.9, 5.3, 2.7 Hz) 2.34(m, 1H), 1.89 (m, 1H).

2-[2-(3-Bromophenyl)chroman-6-yloxy]-5-nitropyridine

¹H NMR (400 MHz, CDCl₃) δ: 9.04 (d, 1H, J 2.9 Hz), 8.60 (dd, 1H, J 9.2, 2.9 Hz), 7.66 (bs, 1H), 7.55 (m, 1H), 7.48 (m, 1H), 7.39 (m, 1H) 7.20 (d, 1H, J 9.2 Hz) 7.01-6.93 (m, 3H), 5.17 (dd, 1H, J 10.1, 2.2 Hz), 2.97 (m, 1H), 2.72 (m, 1H) 2.20 (m, 1H), 2.00 (m, 1H).

2-[2-(4-Ethylphenyl)chroman-6-yloxy]-5-nitropyridine

¹H NMR (400 MHz, CDCl₃) δ: 9.04 (d, 1H, J 2.8 Hz), 8.60 (dd, 1H, J 9.1, 2.8 Hz), 7.36 (d, 2H, J 8.1 Hz) 7.24 (d, 2H, J 8.1 Hz), 7.20 (d, 1H, J 9.1 Hz), 7.00 (d, 1H, J 2.7 Hz) 6.96 (dd, 1H, J 8.8, 2.7 Hz), 6.89 (d, 1H, J 2.7 Hz), 5.11 (dd, 1H, J 10.1, 2.2 Hz), 2.98 (m, 1H), 2.75 (m, 1H), 2.62 (q, 2H, J 7.5 Hz) 2.16 (m, 1H), 2.01 (m, 1H), 1.19 (t, 3H, J 7.5 Hz).

5-Nitro-2-[2-(2-nitrophenyl)chroman-6-yloxy]pyridine

¹H NMR (400 MHz, d₆-DMSO) δ: 9.04 (d, 1H, J 2.9 Hz), 8.60 (dd, 1H, J 9.1, 2.9 Hz), 8.03 (d, 1H, J 7.9 Hz), 7.80-7.85 (m, 2H), 7.62-7.66 (m, 1H), 7.22 (d, 1H, J 9.1 Hz), 7.04 (d, 1H, J 2.8 Hz), 6.98 (dd, 1H, J 8.8, 2.8 Hz), 6.88 (d, 1H, J 8.8 Hz), 5.52 (dd, 1H, J 10.3, 2.0 Hz), 2.99-3.31 (m, 1H), 2.80-2.85 (m, 1H), 2.35-2.40 (m, 1H), 1.99-2.04 (m, 1H).

5-Nitro-2-[2-(3-nitrophenyl)chroman-6-yloxy]pyridine

¹H NMR (400 MHz, d₆-DMSO) δ: 9.04 (d, 1H, J 2.9 Hz), 8.60 (dd, 1H, J 9.0, 2.9 Hz), 8.32 (s, 1H), 8.23 (d, 1H, J 8.3 Hz), 7.95 (d, 1H, J 7.9 Hz), 7.74 (t, 1H, J 15.8, 7.9 Hz), 7.21 (d, 1H, J 9.0 Hz), 6.96-7.03 (m, 3H), 5.35 (d, 1H, J 8.7 Hz), 2.98-3.06 (m, 1H), 2.72-2.79 (m, 1H), 2.26-2.33 (m, 1H), 1.99-2.06 (m, 1H).

5-Nitro-2-[2-(4-nitrophenyl)chroman-6-yloxy]pyridine

¹H NMR (300 MHz, d₆-DMSO) δ: 9.04 (d, 1H, J 2.9 Hz), 8.60 (dd, 1H, J 9.1, 2.9 Hz), 8.29 (d, 2H, J 6.9 Hz), 7.76 (d, 2H, J 6.9 Hz), 7.21 (d, 1H, J 9.1 Hz), 6.98-7.02 (m, 3H), 5.35 (dd, 1H, J 9.9, 2.2 Hz), 2.96-3.05 (m, 1H), 2.73-2.78 (m, 1H), 2.24-2.29 (m, 1H), 1.96-2.04 (m, 1H).

2-[2-(3-Methoxyphenyl)chroman-6-yloxy]-5-nitropyridine

¹H NMR (400 MHz, d₆-DMSO) δ: 9.04 (d, 1H, J 2.9 Hz), 8.60 (dd, 1H, J 9.1, 2.9 Hz), 7.32 (t, 1H, J 15.7, 7.9 Hz), 7.20 (d, 1H, J 9.1 Hz), 7.03 (d, 1H, J 8.4 Hz), 7.01 (s, 1H), 7.00 (d, 1H, J 2.8 Hz), 6.96 (dd, 1H, J 8.7, 2.8 Hz), 6.92 (d, 1H, J 8.7

Hz), 6.90 (dd, 1H, J 8.4, 2.6 Hz), 5.12 (dd, 1H, J 10.0, 2.3 Hz), 3.77 (s, 3H), 2.93-2.97 (m, 1H), 2.71-2.77 (m, 1H), 2.15-2.20 (m, 1H), 1.99-2.05 (m, 1H).

2-(3-Methyl-2-phenylchroman-6-yloxy)-5-nitropyridine $^1$H NMR (400 MHz, $d_6$-DMSO) δ: 9.04 (d, 1H, J 2.8 Hz), 8.59 (dd, 1H, J 9.1, 2.8 Hz), 7.43-7.36 (m, 5H), 7.19 (d, 1H, J 9.1 Hz), 7.00 (d, 1H, J 2.6 Hz) 6.95 (dd, 1H, J 8.7, 2.6 Hz), 6.86 (d, 1H, J 8.7 Hz), 4.73 (d, 1H, J 9.3 Hz), 2.85 (dd, 1H, J −16.7, 5.0 Hz), 2.64 (dd, 1H, J −16.5, 10.9 Hz), 2.18 (m, 1H), 0.77 (d, 3H, J 6.7 Hz).

Example 3

Intermediates (5-Nitropyridin-2-yloxy)-2-phenylchroman-4-one Intermediates 6-(5-Nitropyridin-2-yloxy)-2-phenylchroman-4-one 6-(5-Nitropyridin-2-yloxy)-2-phenylchroman-4-one was prepared as described for 5-Nitro-2-(2-phenylchroman-6-yloxy)pyridine in Example 1(b) using 200 mg of 6-hydroxyflavanone. $^1$H NMR (400 MHz, $d_6$-DMSO) δ: 9.03 (bs, 1H), 8.64 (d, 1H, J 9.0 Hz), 7.59-7.41 (m, 7H), 7.31 (d, 1H, J 9.0 Hz), 7.23 (d, 1H, 8.8 Hz), 5.75 (dd, 1H, J 12.3, 2.9 Hz), 3.30 (dd, 1H, −16.3, 12.3 Hz), 2.87 (dd, 1H, −16.3, 2.9 Hz).

Using the same procedure as described above for 6-(5-nitropyridin-2-yloxy)-2-phenylchroman-4-one, but replacing 6-hydroxyflavanone by an appropriate 2-phenylchromanone derivative, there was obtained:

7-(5-Nitropyridin-2-yloxy)-2-phenylchroman-4-one $^1$H NMR (400 MHz, $d_6$-DMSO) δ: 9.07 (d, 1H, J 2.8 Hz), 8.67 (dd, 1H, J 9.0, 2.8 Hz), 7.89 (d, 1H, 8.6 Hz), 7.60-7.35 (m, 6H), 7.04 (d, 1H, 2.1 Hz), 6.97 (dd, 1H, 8.6, 2.1 Hz), 5.75 (dd, 1H, J 13.0, 2.7 Hz), 3.32 (dd, 1H, 16.9, 13.0 Hz), 2.85 (d, −16.9, 2.7 Hz).

3-Methyl-6-(5-nitropyridin-2-yloxy)-2-phenylchroman-4-one $^1$H NMR (400 MHz, $d_6$-DMSO) δ: 9.03 (d, 1H, J 2.9 Hz), 8.64 (dd, 1H, J 9.1, 2.9 Hz), 7.59-7.56 (m, 3H), 7.50-7.32 (m, 4H) 7.30 (d, 1H, J 9.1 Hz), 7.18 (d, 1H, J 8.9 Hz), 5.38 (d, 1H, J 12.5 Hz), 3.36 (dd, 1H, J 12.5, 6.9 Hz), 0.86 (d, 3H, J 6.9 Hz).

Example 4

Intermediate 2-(2,3-Dihydro-2-phenyl-benzo[1,4]dioxin-6-yloxy)-5-nitropyridine a) 1-[2,5-Bis(benzyloxy)phenyl]ethanone A mixture of 1-(2,5-dihydroxyphenyl)ethanone (3.16 g), benzyl chloride (7.04 g), potassium carbonate (12.4 g) and 18-Crown-6 (30 mg) in 2-butanone (50 ml) was heated under reflux for 5 hrs. After cooling the precipitate was filtered off. The filtrate was evaporated to dryness under reduced pressure and ether (50 ml) was added to it. The solution was washed twice with dilute sodium hydroxide solution, twice with dilute hydrochloric acid, dried over sodium sulphate and substantially evaporated to dryness under reduced pressure. The residue was triturated with cold n-heptane (30 ml), and the precipitate was filtered off with suction filtration giving after drying 2.85 g of 1-[2,5-bis(benzyloxy)phenyl]ethanone. $^1$H NMR (400 MHz, DMSO-$d_6$) δ: 2.50 (s, 3H), 5.08 (s, 2H), 5.18 (s, 2H), 7.20-7.50 (m, 13H).

b) Acetic acid 2,5-bis(benzyloxy)phenyl ester

A solution of 1-[2,5-bis(benzyloxy)phenyl]ethanone (2.25 g) and peracetic acid 40% (1.63 ml) in acetic acid (5.4 ml) was stirred at 60° C. for 1 h. After cooling to room temperature the precipitated product was collected by filtration, washed with cold ether and dried under reduced pressure. Acetic acid 2,5-bis(benzyloxy)phenyl ester was recrystallized from 2-propanol. Yield is 1.87 g. $^1$H NMR (DMSO-$d_6$) δ: 2.23 (s, 1H), 5.03 (s, 2H), 5.05 (s, 2H), 6.84-7.44 (m, 13H).

c) 2,5-Bis(benzyloxy)phenol

A solution of acetic acid 2,5-bis(benzyloxy)phenyl ester (1.85 g) and 5M sodium hydroxide solution (10.6 ml) in ethanol (11 ml) was heated under reflux for 6.5 hrs. After ethanol was evaporated under reduced pressure the clear solution was made acidic with diluted hydrochloric acid. The precipitated product was collected by filtration, washed with cold water and dried under reduced pressure. Yield is 0.56 g. $^1$H NMR (DMSO-$d_6$) δ: 4.97 (s, 2H), 5.01 (s, 2H), 6.34 (dd, J 3.1, 8.8 Hz, 1H), 6.49 (d, J 3.1 Hz, 1H), 6.85 (d, J 8.8 Hz, 1H), 7.28-7.46 (m, 10H), 9.1 (br s, 1H).

d) 2-[2,5-Bis(benzyloxy)phenoxy]-1-phenylethanone

A mixture of 2,5-bis(benzyloxy)phenol (0.28 g), 2-bromoacetophenone (0.22 g), potassium hydrogen-carbonate (0.25 g) and 18-Crown-6 (3 mg) in acetonitrile (4.2 ml) was stirred at 22° C. for one week. The mixture was filtered and evaporated to dryness under reduced pressure. The residue was triturated with the mixture of ether (8.2 ml) and water (1.4 ml) at the ice bath temperature. The product was collected by filtration, washed with cold ether and dried under reduced pressure. Yield is 0.14 g. $^1$H NMR (DMSO-$d_6$) δ: 4.98 (s, 2H), 5.06 (s, 2H), 5.58 (s, 2H), 6.51 (dd, J 8.9, 2.3 Hz, 1H), 6.68 (d, J 2.3 Hz, 1H), 6.94 (d, J 8.9 Hz, 1H), 7.28-8.03 (m, 15H).

e) 2-[2,5-Bis(benzyloxy)phenoxy]-1-phenylethanol

To the solution of 2-[2,5-bis(benzyloxy)phenoxy]-1-phenylethanone (0.14 g) in methanol (0.5 ml) and tetrahydrofuran (1.9 ml) was added at the 0° C. temperature sodium borohydride (6.5 mg). The reaction was stirred 15 minutes at 0° C. and 2 hrs at 22° C. temperature. After adding water (5 ml) methanol and tetrahydrofuran were evaporated off. After the residue was stirred at 22° C. 0.5 hr the product was filtered, washed with cold water and dried under reduced pressure. Yield is 0.09 g. $^1$H NMR (DMSO-$d_6$) δ: 4.05 (m, 2H), 4.91 (m, 1H), 4.95 (s, 2H), 5.01 (s, 2H), 5.59 (d, J 4.7 Hz, 1H), 6.47 (dd, J 2.8, 8.8 Hz, 1H), 6.68 (d, J 2.8 Hz, 1H), 6.89 (d, J 8.8 Hz, 1H), 7.24-7.45 (m, 15H).

f) 2-(2-Hydroxy-2-phenylethoxy)benzene-1,4-diol

A solution of 2-[2,5-bis(benzyloxy)phenoxy]-1-phenylethanol (3.9 g) in ethanol (175 ml) was hydrogenated in the presence of 10% palladium on charcoal (100 mg) at 30 psi. The catalyst was removed by filtration and the solvent was evaporated under reduced pressure. The residue was recrystallized from the mixture of toluene-ethyl acetate 8:1 (15 ml). The yield of 2-(2-Hydroxy-2-phenylethoxy)benzene-1,4-diol is 1.2 g. $^1$H NMR (DMSO-$d_6$) δ: 3.79 (dd, J 9.6, 8.3 Hz, 1H), 4.00 (dd, J 9.6, 3.6 Hz, 1H), 4.94 (ddd, J 3.6, 8.3, 3.9 Hz, 1H), 5.66 (d, J 3.9 Hz, 1H), 6.18 (dd, J 8.5, 2.3 Hz, 1H), 6.34 (d, J 2.3, 1H), 6.57 (d, J 8.5, 1H), 7.26-7.47 (m, 5H), 7.97 (s, 1H), 8.66 (s, 1H).

g) 2,3-Dihydro-2-phenyl-benzo[1,4]dioxin-6-ol

A solution of 2-(2-hydroxy-2-phenylethoxy)benzene-1,4-diol (1.2 g) in toluene (75 ml) was heated with Amberlyst 15 catalyst (0.5 g) under reflux for 7 hrs. After filtering the solvent was evaporated under reduced pressure. The residue was purified by column chromatography on silica gel (toluene/ethyl acetate/acetic acid, 8:1:1). The yield of 2,3-dihydro-2-phenyl-benzo[1,4]dioxin-6-ol is 0.5 g. $^1$H NMR (DMSO-$d_6$) δ: 4.02 (dd, J 8.5, 11.4 Hz, 1H), 4.35 (dd, J 2.3, 11.4 Hz, 1H), 5.11 (dd, J 8.5, 2.3 Hz, 1H), 6.29 (dd, J 2.8, 8.5 Hz, 1H), 6.32 (d, J 2.8 Hz, 1H), 6.75 (d, J 8.5 Hz, 1H), 7.36-7.47 (m, 5H), 8.99 (s, 1H).

h) 2-(2,3-Dihydro-2-phenyl-benzo[1,4]dioxin-6-yloxy)-5-nitropyridine

A solution of 2,3-dihydro-2-phenyl-benzo[1,4]dioxin-6-ol (80 mg), 2-chloro-5-nitropyridine (56 mg) and potassium carbonate (52 mg) in dimethylformamide (1.0 ml) was stirred at 120° C. for 2 hrs. After cooling the mixture water (10 ml) was added and the precipitated product was filtered, washed with water and 2-propanol and dried under reduced pressure. Yield is 60 mg and mp 163-170° C. $^1$H NMR (DMSO-$d_6$) δ 4.16 (dd, J 8.5, 11.6 Hz, 1H), 4.47 (dd, J 11.6, 2.6 Hz, 1H), 5.28 (dd, J 2.6, 8.5 Hz, 1H), 6.75 (dd, J 2.6, 8.8 Hz, 1H), 6.88 (d, J 2.6 Hz, 1H), 7.05 (d, J 8.8 Hz, 1H), 7.21 (d, J 9.1 Hz, 1H), 7.39-7.52 (m, 5H), 8.60 (dd, J 2.8, 9.1 Hz, 1H), 9.05 (d, J 2.8 Hz, 1H).

Example 5

Intermediate

5-Nitro-2-(6-phenyl-5,6,7,8-tetrahydro-naphthalen-2-yloxy)-pyridine a)
6-Methoxy-2-phenyl-3,4-dihydro-2H-naphthalen-1-one A mixture of palladium(II) acetate (0.57 g), rac-2,2'-bis(diphenylphosphino)-1,1'-binaphtyl (1.91 g) and potassium tert-butoxide (4.15 g) in dry toluene was stirred under argon for 10 minutes. Bromobenzene (5.34 g) and 6-methoxy-1-tetralone (3.0 g) solvated in dry toluene were added and the mixture was stirred at 100° C. for 2 h. The reaction mixture was cooled to room temperature and poured into saturated aqueous ammonium chloride and extracted with ethyl ether. Organic extract was washed with brine, dried and evaporated. The crude product was purified by flash chromatography on silica gel using toluene and toluene-ethyl acetate (9:1) as an eluant. $^1$H NMR (400 MHz, $d_6$-DMSO) δ: 7.87 (d, 1H, J 7.8 Hz), 7.16-7.33 (m, 5H), 6.91-6.94 (m, 2H), 3.85 (s, 3H), 3.82-3.88 (m, 1H), 3.06-3.14 (m, 1H), 2.92-2.98 (m, 1H), 2.23-2.38 (m, 2H).

b)
6-Hydroxy-2-phenyl-3,4-dihydro-2H-naphthalen-1-one

6-Methoxy-2-phenyl-3,4-dihydro-2H-naphthalen-1-one (1.0 g) was refluxed with 47% HBr (20 ml) until disappearance of the starting material. The mixture was poured into water and extracted with ethyl acetate. Ethyl acetate was dried and evaporated. The product was recrystallised from toluene. $^1$H NMR (400 MHz, $d_6$-DMSO) δ: 10.35 (s, 1H), 7.79 (d, 1H, J 8.6 Hz), 7.15-7.33 (m, 5H), 6.75 (dd, 1H, J 8.6, 2.4 Hz), 6.68 (d, 1H, J 2.3 Hz), 3.79-3.85 (m, 1H), 2.99-3.06 (m, 1H), 2.83-2.90 (m, 1H), 2.19-2.33 (m, 2H).

c) 6-Phenyl-5,6,7,8-tetrahydro-naphthalen-2-ol

To a solution of 6-hydroxy-2-phenyl-3,4-dihydro-2H-naphthalen-1-one (50 mg) in trifluoroacetic acid was added triethylsilane (98 mg). The mixture was heated at 60° C. for 3 h. Solvent was evaporated, water added to the residue and the mixture extracted with ethyl acetate. Organic extract was dried and evaporated. $^1$H NMR (400 MHz, $d_6$-DMSO) δ: 9.02 (s, 1H), 7.18-7.32 (m, 5H), 6.87 (d, 1H, J 7.9), 6.50-6.53 (m, 2H), 2.68-2.92 (m, 5H), 1.94-1.99 (m, 1H), 1.81-1.89 (m, 1H).

d) 5-Nitro-2-(6-phenyl-5,6,7,8-tetrahydro-naphthalen-2-yloxy)-pyridine

6-Phenyl-5,6,7,8-tetrahydro-naphthalen-2-ol (30 mg), 2-chloro-5-nitropyridine (21 mg) and potassium fluoride (23 mg) in dry dimethylformamide were heated at 120° C. until disappearance of the starting material. Water and 1 N HCl were added and the mixture extracted with ethyl acetate. Ethyl acetate was washed with brine and water, dried and evaporated. The product was recrystallised from toluene. $^1$H NMR (400 MHz, $d_6$-DMSO) δ: 9.04 (d, 1H, J 2.4 Hz), 8.61 (dd, 1H, J 9.0, 2.5), 7.18-7.35 (m, 7H), 6.95-6.99 (m, 2H), 2.83-3.01 (m, 5H), 1.87-2.04 (m, 2H).

Example 6

Intermediate 6-(5-Nitro-pyridin-2-yloxy)-2-phenyl-3,4-dihydro-2H-naphthalen-1one 6-(5-Nitro-pyridin-2-yloxy)-2-phenyl-3,4-dihydro-2H-naphthalen-1-one was prepared as described for 5-nitro-2-(6-phenyl-5,6,7,8-tetrahydro-naphthalen-2-yloxy)-pyridine in Example 5(d) using 50 mg 6-hydroxy-2-phenyl-3,4-dihydro-2H-naphthalen-1-one, 33 mg 2-chloro-5-nitropyridine and 37 mg potassium fluoride. $^1$H NMR (400 MHz, $d_6$-DMSO) δ: 9.07 (d, 1H, J 2.8 Hz), 8.68 (dd, 1H, J 9.0, 2.9), 8.01 (d, 1H, J 8.5), 7.37 (d, 1H, J 9.1 Hz), 7.21-7.38 (m, 7H), 3.96-4.04 (m, 1H), 3.15-3.23 (m, 1H), 2.98-3.04 (m, 1H), 2.39-2.48 (m, 1H), 2.25-2.31 (m, 1H).

Example 7

Intermediates

2-[3-(phenyl)chroman-7-yloxy]-5-nitropyridine Intermediates a) 2-(3-Fluorophenyl)-1-(2-hydroxy-4-methoxyphenyl)ethanone (3-Fluorophenyl)acetic acid (3.7 g) and 3-methoxyphenol (3.0 g) were dissolved into $BF_3.Et_2O$ (60 ml, 20 eq) under argon. The mixture was stirred at 60-70° C. until disappearance of the starting materials (9 h) and poured into large volume of ice water. After extraction with ethyl acetate the combined organic layers were washed with water, dried and evaporated. The crude product was purified by column chromatography using $CH_2Cl_2$ as an eluant. $^1$H NMR (400 MHz, $d_6$-DMSO) δ: 12.41 (br s, 1H), 8.02 (d, 1H, J 9.0 Hz), 7.34-7.38 (m, 1H), 7.09-7.13 (m, 3H), 6.56 (dd, 1H, J 9.0, 2.5 Hz), 6.49 (d, 1H, J 2.5 Hz), 4.41 (s, 2H), 3.83 (s, 3H).

b) 3-(3-Fluorophenyl)-7-methoxychromen-4-one 2-(3-Fluorophenyl)-1-(2-hydroxy-4-methoxyphenyl)ethanone (1.76 g) was dissolved in pyridine (88 ml). Piperidine (8.8 ml) and triethylorthoformate (88 ml) were added and the mixture was stirred at 120° C. for 3.5 hours. After pouring the mixture into water and acidification with conc. HCl the crude product was filtered. Purification by column chromatography using heptane-ethyl acetate (7:3) as an eluant afforded 3-(3-fluorophenyl)-7-methoxychromen-4-one. $^1$H NMR (400 MHz, $d_6$-DMSO) δ: 8.57 (s, 1H), 8.06 (d, 1H, J 8.9 Hz), 7.45-7.50 (m, 3H), 7.21-7.25 (m, 1H), 7.20 (d, 1H, J 2.4 Hz), 7.12 (dd, 1H, J 8.9, 2.4 Hz), 3.92 (s, 3H).

c) 3-(3-Fluorophenyl)-7-hydroxychromen-4-one 3-(3-Fluorophenyl)-7-methoxychromen-4-one (320 mg) was refluxed with 47% HBr (18 ml) until disappearance of the starting material. The mixture was poured into water and the precipitate was filtrated and dried yielding 3-(3-fluorophenyl)-7-hydroxychromen-4-one. $^1$H NMR (400 MHz, $d_6$-DMSO) δ: 10.87 (s, 1H), 8.49 (s, 1H), 7.99 (d, 1H, J 8.7 Hz), 7.43-7.49 (m, 3H), 7.20-7.24 (m, 1H), 6.97 (dd, 1H, J 8.7, 2.2 Hz), 6.90 (d, 1H, J 2.2 Hz).

d) 3-(3-Fluorophenyl)chroman-7-ol 3-(3-Fluorophenyl)-7-hydroxychromen-4-one (160 mg) was dissolved in ethanol (40 ml) and 10% palladium on carbon (400 mg) was added. The reaction mixture was hydrogenated for 6 hours at normal pressure and room temperature. It was then filtered through Celite and washed with ethanol. The solvent was evaporated under reduced pressure to give 3-(3-fluorophenyl)chroman-7-ol. $^1$H NMR (400 MHz, $d_6$-DMSO) δ: 9.19 (br s, 1H), 7.38 (m, 1H), 7.17-7.21 (m, 2H), 7.08 (m, 1H), 6.88 (d, 1H, J 8.2 Hz), 6.30 (dd, 1H, J 8.2, 2.4 Hz), 6.20 (d, 1H, J 2.4 Hz), 4.22 (dd, 1H, J 10.3, 3.6 Hz), 4.02 (t, 1H, 10.3 Hz), 3.20 (m, 1H), 2.90 (m, 2H).' e) 2-[3-(3-Fluorophenyl)chroman-7-yloxy]-5-nitropyridine

2-[3-(3-Fluorophenyl)chroman-7-yloxy]-5-nitropyridine was prepared as described for 5-nitro-2-(2-phenylchroman-6-yloxy)pyridine in Example 1(b) using 125 mg of 3-(3-fluorophenyl)-chroman-7-ol. The product was recrystallised from ethanol. $^1$H NMR (400 MHz, $CDCl_3$) δ: 9.07 (d, 1H, J 2.8 Hz), 8.47 (dd, 1H, J 9.0, 2.8 Hz), 7.33 (m, 1H), 7.16 (d, 1H J 8.9 Hz), 6.95-7.06 (m, 4H), 6.69-6.71 (m, 2H), 4.38 (dd, 1H, J 10.6, 4.3 Hz), 4.06 (t, 1H, 10.6 Hz), 3.30 (m, 1H), 3.06 (m, 2H).

Using the same procedure as described above for 3-(3-fluorophenyl)chroman-7-ol, but replacing 3-(3-fluorophenyl)-7-hydroxychromen-4-one by 7-hydroxy-3-phenylchromen-4-one, there was obtained:

3-Phenylchroman-7-ol $^1$H NMR (400 MHz, $d_6$-DMSO) δ: 8.18 (br s, 1H), 7.31-7.34 (m, 4H), 7.25-7.27 (m, 1H), 6.88 (d, 1H, J 8.2 Hz), 6.30 (dd, 1H, J 8.2, 2.4 Hz), 6.20 (d, 1H, J 2.4 Hz), 4.21 (dd, 1H, J 10.3, 3.6 Hz), 4.00 (t, 1H, J 10.3 Hz), 3.13 (m, 1H), 2.84-2.87 (m, 2H).

Using the same procedure as described above for 2-[3-(3-fluorophenyl)chroman-7-yloxy]-5-nitropyridine, but replacing 3-(3-fluorophenyl)chroman-7-ol by 3-phenylchroman-7-ol, there was obtained:

5-Nitro-2-(3-phenylchroman-7-yloxy)pyridine $^1$H NMR (400 MHz, $d_6$-DMSO) δ: 9.05 (d, 1H, J 2.9 Hz), 8.61 (dd, 1H, J 9.1, 2.9 Hz), 7.34-7.38 (m, 4H), 7.27-7.30 (m, 1H), 7.22 (m, 2H), 6.70-6.74 (m, 2H), 4.31 (dd, 1H, J 10.4, 3.5 Hz), 4.12 (t, 1H, 10.4 Hz), 3.24 (m, 1H), 3.01-3.11 (m, 2H).

7-Hydroxy-3-phenylchromen-4-one is commercially available or can be synthesised by methods described for 3-(3-fluorophenyl)-7-hydroxychromen-4-one.

Example 8

Intermediate

5-Nitro-2-(2-phenyl-2,3-dihydrobenzo[1,4]oxathiin-6-yloxy)pyridine a) 2-(2-Hydroxy-1-phenylethylsulfanyl)benzene-1,4-diol

To a stirred solution of 2-mercaptobenzene-1,4-diol (0.5 g) and potassium carbonate (0.49 g) in water (5 ml) was added 2-phenyloxirane (0.40 ml) under argon. The mixture was stirred at room temperature for 2.5 hours and then treated with 2 M HCl and extracted with ethyl acetate. The combined organic layers were washed with water and brine, dried and evaporated. The crude product was purified by column chromatography using heptane-ethyl acetate (1:1) as an eluant. $^1$H NMR (400 MHz, $d_6$-DMSO) δ: 8.94 (br s, 1H), 8.72 (br s, 1H), 7.24-7.37 (m, 5H), 6.62-6.65 (m, 2H), 6.47 (dd, 1H, J 8.6, 2.8 Hz), 4.97 (br s, 1H), 4.34 (m, 1H), 3.72 (m, 2H).

b) 2-Phenyl-2,3-dihydrobenzo[1,4]oxathiin-6-ol

A solution of 2-(2-hydroxy-1-phenylethylsulfanyl)benzene-1,4-diol (0.83 g) in dry toluene (60 ml) was stirred with Amberlyst 15 (0.5 g) at 60° C. until disappearance of the starting material. After the mixture was filtered and solvent evaporated the crude product was purified by column chromatography using heptane-ethyl acetate (1:1) as an eluant. $^1$H NMR (400 MHz, $CDCl_3$) δ: 7.41 (m, 4H), 7.33-7.40 (m, 1H), 6.81 (d, 1H, J 8.7 Hz), 6.61 (d, 1H, J 3.0 Hz), 6.51 (dd, 1H, J 8.7, 3.0 Hz), 5.10 (dd, 1H, J 9.6, 1.9 Hz), 3.28 (dd, 1H, J 13.0, 9.6 Hz), 3.06 (dd, 1H, J 13.0, 1.9 Hz).

c) 5-Nitro-2-(2-phenyl-2,3-dihydrobenzo[1,4]ox-athiin-6-yloxy)pyridine

5-Nitro-2-(2-phenyl-2,3-dihydrobenzo[1,4]oxathiin-6-yloxy)pyridine was prepared as described for 5-nitro-2-(2-phenylchroman-6-yloxy)pyridine in Example 1(b) using 269 mg 2-phenyl-2,3-dihydrobenzo[1,4]oxathiin-6-ol. The product was recrystallised from ethanol. $^1$H NMR (400 MHz, CDCl$_3$) δ: 9.07 (d, 1H, J 2.8 Hz), 8.47 (dd, 1H, J 9.1, 2.8 Hz), 7.43 (m, 4H), 7.37-7.41 (m, 1H), 7.02 (d, 1H, J 9.1 Hz), 6.99 (d, 1H, J 8.9 Hz), 6.95 (d, 1H, J 2.8 Hz), 6.82 (dd, 1H, J 8.9, 2.8 Hz), 5.21 (dd, 1H, J 9.7, 1.9 Hz), 3.31 (dd, 1H, 13.2, 9.7 Hz), 3.11 (dd, 1H, 13.2, 1.9 Hz).

Example 9

Intermediate

5-Nitro-2-(2-phenylindan-5-yloxy) pyridine a) 3-(4-Methoxyphenyl)-2-phenylacrylic acid

Triethylamine was added to solution of p-anisaldehyde (10 g) and phenylacetic acid (10 g) in acetic anhydride (25 ml). Reaction mixture was stirred at 90° C. for 8 h. Reaction mixture was cooled and water (600 ml) solution of potassium carbonate (81 g) was added. After addition reaction mixture was heated at 60° C. for an hour. Before neutralising with concentrated hydrochloric acid the reaction mixture was cooled below 10° C. Precipitate was filtered and washed with water. $^1$H-NMR (400 MHz, d$_6$-DMSO): 12.6 (bs, 1H), 7.67 (s, 1H), 7.4-7.3 (m, 3H), 7.2-7.1 (m, 2H), 7.0-6.9 (m, 2H), 6.8-6.7 (m, 2H), 3.70 (s, 3H). (M)$^+$=254 (100%).

b) 3-(4-Methoxyphenyl)-2-phenylpropionic acid 13 g of 3-(4-methoxyphenyl)-2-phenylacrylic acid was dissolved to 600 ml of ethyl acetate and 2.6 g of 10% palladium on charcoal was added under inert atmosphere. Starting material was hydrogenated at room temperature to give quantitative yield of 3-(4-methoxyphenyl)-2-phenylpropionic acid. $^1$H-NMR (400 MHz, d$_6$-DMSO): 12.3 (bs, 1H), 7.32-7.20 (m, 5H), 7.1-7.0 (m, 2H), 6.8-6.7 (m, 2H), 3.79 (dd, 1H, J 6.9, 8.7 Hz), 3.70 (s, 3H), 3.22 (dd, 1H, J 8.7, 13.7 Hz), 2.87 (dd, 1H, J 6.9, 13.7 Hz).

c) 6-Methoxy-2-phenylindan-1-one

To solution of 3-(4-methoxyphenyl)-2-phenylpropionic acid (4.6 g) in dry methylene chloride (26 ml) was added two drops of dry DMF. Thionylchloride (3 ml) was added and reaction mixture was stirred at 40° C. for 4 h. Solvent was evaporated under vacuum. Precipitate was dissolved to methylene chloride. Solution was cooled to 0-3° C. This solution and aluminium chloride (2.5 g) were mixed slowly over 4 hours keeping temperature under 4° C. After mixing reaction mixture was stirred at room temperature for 2 h. Reaction was quenched by pouring to dilute ice cold hydrochloric acid. Layers were separated and water solution was extracted with methylene chloride. Combined organic layers were washed with water, dried and evaporated. Crude product was triturated to give 2.9 g of 6-Methoxy-2-phenylindan-1-one. $^1$H-NMR (400 MHz, d$_6$-DMSO): 7.56 (d, 1H), 7.35-7.23 (m, 4H), 7.18-7.13 (m, 3H), 4.02 (dd, 1H, J 3.9, 8.0 Hz), 3.82 (s, 3H), 3.61 (dd, 1H, J 8.0, 17.2 Hz), 3.11 (dd, 1H, J 3.9, 17.2 Hz).

d) 5-Methoxy-2-phenylindane

5-Methoxy-2-phenylindane was prepared as described for 2-phenylchroman-6-ol in Example 1(a) using 600 mg of 6-methoxy-2-phenylindan-1-one. $^1$H-NMR (400 MHz, d$_6$-DMSO): 7.32-7.27 (m, 4H), 7.21-7.18 (m, 1H), 7.13 (d, 1H, J 8.2 Hz), 6.83 (d, 1H, J 2.4 Hz), 6.72 (dd, 1H, J 2.4, 8.2 Hz), 3.72 (s, 3H), 3.64 (k, 1H, J 8.5 Hz), 3.23 (dt, 2H, J 8.5, 15.9 Hz), 2.92 (m, 2H).

e) 2-Phenylindan-5-ol

Mixture of 5-methoxy-2-phenylindane (200 mg) and concentrated HBr (4 ml) was refluxed for 5.5 h. Reaction mixture was allowed to cool to room temperature and 20 ml of ice water and it was extracted with methylene chloride. The combined organic layers were washed with brine and dried with Na$_2$SO$_4$. The solvents were evaporated to give 2-phenylindan-5-ol. $^1$H-NMR (400 MHz, d$_6$-DMSO): 9.05 (bs, 1H), 7.3-7.28 (m, 4H), 7.26-7.15 (m, 1H), 7.0 (d, 1H, J 8.1 Hz), 6.64 (d, 1H, J 1.9 Hz), 6.55 (dd, 1H, J 1.9, 8.1 Hz), 3.60 (k, 1H, J 8.6 Hz), 3.18 (m, 2H), 2.86 (dt, 2H, J 8.6, 16 Hz).

f) 5-Nitro-2-(2-phenylindan-5-yloxy) pyridine

5-Nitro-2-(2-phenylindan-5-yloxy) pyridine was prepared as described for 2-phenylchroman-6-yloxy)pyridine in Example 1(b) using 107 mg of 2-phenylindan-5-ol. $^1$H-NMR (400 MHz, d$_6$-DMSO): 9.04 (d, 1H, J 2.9 Hz), 8.61 (dd, 1H, J 2.9, 9.1 Hz), 7.38-7.28 (m, 5H), 7.24-7.20 (m, 2H), 7.11 (d, 1H, J 2.2 Hz), 7.00 (dd, 1H, J 2.2, 8.0 Hz), 3.72 (k, 1H, J 8.9 Hz), 3.36-3.28 (m, 2H), 3.01 (dd, 2H, J 8.9, 15.3 Hz).

Example 10

Intermediates

5-Aminopyridine Intermediates

5-Amino-2-(2-phenylchroman-6-yloxy)pyridine

5-Nitro-2-(2-phenylchroman-6-yloxy)pyridine (2.26 g) was dissolved in 350 ml of glacial acetic acid. Zinc powder (8.48 g) was added in few portions due to exothermic reaction. The mixture was stirred at room temperature for 2 hours and filtered. The zinc was washed with glacial acetic acid. The acid was evaporated and toluene was added and evaporated again. A product mixture was dissolved in CH$_2$Cl$_2$ and washed with 1M NaOH. Water phase was further washed with CH$_2$Cl$_2$. Both organic fractions were combined and dried over Na$_2$SO$_4$. Product was purified by column chromatography. $^1$H-NMR (400 MHz; d$_6$-DMSO) δ: 7.52 (d, 1H, J 2.8 Hz), 7.46-7.30 (m, 5H), 7.05 (dd, 1H, J 8.6, 3.0 Hz), 6.82-6.72 (m, 3H), 6.69 (d, 1H, J 8.6 Hz), 5.08 (dd, 1H, J 10.0, 2.1 Hz), 5.00 (s, 2H), 3.00-2.87 (m, 1H), 2.74-2.64 (m, 1H), 2.19-2.10 (m, 1H), 2.05-1.91 (m, 1H).

Using the same procedure as described above for 5-amino-2-(2-phenylchroman-6-yloxy)pyridine, but replacing 5-nitro-2-(2-phenylchroman-6-yloxy)pyridine by an appropriate nitropyridine intermediate, there was obtained:

6-[2-(4-Fluorophenyl)chroman-6-yloxy]pyridin-3-ylamine $^1$H NMR (400 MHz, d$_6$-DMSO) δ: 7.52-7.47 (m, 3H), 7.24 (m, 2H), 7.05 (dd, 1H, J 8.6, 3.0 Hz), 6.84-6.68 (m, 4H), 5.09

(dd, 1H, J 10.2, 2.1 Hz), 5.00 (bs, 2H), 2.93 (m, 1H), 2.69 (m, 1H), 2.13 (m, 1H), 1.98 (m, 1H).

6-[2-(3-fluorophenyl)chroman-6-yloxy]-pyridin-3-ylamine $^1$H NMR (400 MHz, d$_6$-DMSO) δ: 7.51 (d, 1H, J 3.0 Hz), 7.44 (m, 1H), 7.30-7.25 (m, 2H), 7.16 (m, 1H), 7.05 (dd, 1H, J 8.6, 3.0 Hz), 6.83-6.73 (m, 3H), 6.69 (d, 1H, J 8.6 Hz), 5.13 (dd, 1H, J 10.0, 3.0 Hz), 5.00 (s, 2H), 2.93 (ddd, 1H, −16.8, 10.5, 5.3 Hz), 2.68 (ddd, 1H, J −16.8, 8.0, 4.4 Hz), 2.18 (m, 1H), 1.96 (m, 1H).

6-[2-(2-Fluorophenyl)chroman-6-yloxy]-pyridin-3-ylamine $^1$H NMR (400 MHz, d$_6$-DMSO) δ: 7.52 (m, 1H), 7.51 (d, 1H, J 3.0 Hz), 7.41 (m, 1H), 7.28-7.24 (m, 2H), 7.05 (dd, 1H, J 8.6, 3.0 Hz), 6.81-6.73 (m, 3H), 6.70 (d, 1H, J 8.6 Hz), 5.31 (dd, 1H, J 10.3, 2.2 Hz), 5.00 (s, 2H), 2.98 (m, 1H), 2.72 (m, 1H), 2.15 (m, 1H), 2.06 (m, 1H).

6-[2-(2,3-Difluorophenyl)chroman-6-yloxy]-pyridin-3-ylamine $^1$H NMR (400 MHz, d$_6$-DMSO) δ: 7.52 (d, 1H, J 3.0 Hz), 7.45-7.27 (m, 3H), 7.06 (dd, 1H, J 8.6, 3.0 Hz), 6.76-6.69 (m, 4H), 5.36 (dd, 1H, J 10.3, 2.2 Hz), 5.01 (bs, 21), 2.97 (m, 1H), 2.73 (m, 1H), 2.18 (m, 1H), 2.03 (m, 1H).

6-[2-(2,4-Difluorophenyl)chroman-6-yloxy]-pyridin-3-ylamine $^1$H NMR (400 MHz, d$_6$-DMSO) δ: 7.58 (m, 1H), 7.51 (d, 1H, J 3.3 Hz), 7.30 (m, 1H), 7.15 (m, 1H), 7.05 (dd, 1H, J 8.3, 3.3 Hz), 6.84-6.73 (m, 3H), 6.70 (d, 1H, J 8.3 Hz), 5.27 (dd, 1H, J 10.3, 2.3 Hz), 5.01 (bs, 2H), 2.97 (m, 1H), 2.73 (m, 1H), 2.13 (m, 1H), 2.03 (m, 1H).

6-[2-(2,5-Difluorophenyl)chroman-6-yloxy]-pyridin-3-ylamine $^1$H NMR (300 MHz, d$_6$-DMSO) δ: 7.51 (d, 1H, J 2.9 Hz), 7.36-7.25 (m, 3H), 7.05 (dd, 1H, J 8.6, 2.9 Hz), 6.84-6.68 (m, 4H), 5.29 (d, 1H, J 8.6), 4.99 (bs, 2H), 2.96 (m, 1H), 2.72 (m, 1H), 2.14 (m, 1H), 2.01 (m, 1H).

6-[2-(2,6-Difluorophenyl)chroman-6-yloxy]-pyridin-3-ylamine $^1$H NMR (400 MHz, d$_6$-DMSO) δ: 7.52-7.47 (m, 2H), 7.24 (m, 1H), 7.19-7.14 (m, 3H), 7.07 (dd, 1H, J 8.6, 2.9 Hz), 6.76-6.51 (m, 3H), 5.37 (dd, 1H, J 11.6, 2.0 Hz), 5.00 (bs, 2H), 3.00 (m, 1H), 2.78 (m, 1H), 2.32 (m, 1H), 2.11 (m, 1H).

6-[2-(3,5-Difluorophenyl)chroman-6-yloxy]-pyridin-3-ylamine $^1$H NMR (400 MHz, d$_6$-DMSO) δ: 7.51 (d, 1H, J 2.9 Hz), 7.22-7.17 (m, 3H), 7.05 (dd, 1H, J 8.6, 2.9 Hz), 6.84 (dd, 1H, J 7.9, 2.0 Hz), 6.76-6.74 (m, 2H), 6.69 (d, 1H, J 8.6 Hz), 5.14 (dd, 1H, J 10.0, 2.2 Hz), 5.01 (bs, 2H), 2.91 (m, 1H), 2.69 (m, 1H), 2.20 (m, 1H), 1.97 (m, 1H).

6-[2-(4-Trifluoromethylphenyl)chroman-6-yloxy]pyridin-3-ylamine $^1$H NMR (400 MHz, d$_6$-DMSO) δ: 7.78 (d, 2H, J 8.4 Hz), 7.68 (d, 2H, J 8.4 Hz), 7.52 (dd, 1H, J 2.9, 0.5 Hz), 7.06 (dd, 1H, 8.6, 2.9 Hz) 6.84 (m, 1H), 6.77-6.75 (m, 2H), 6.70 (dd, 1H, J 8.6, 0.5 Hz), 5.23 (dd, 1H, J 10.0, 2.0 Hz), 5.01 (bs, 2H), 2.95 (ddd, 1H, −16.8, 11.1, 5.9 Hz), 2.69 (ddd, 1H, J −16.8, 8.5, 4.8 Hz), 2.21 (m, 1H), 1.97 (m, 1H).

6-[2-(2-Chlorophenyl)chroman-6-yloxy]pyridin-3-ylamine $^1$H NMR (400 MHz, d$_6$-DMSO) δ: 7.59 (m, 1H), 7.52-7.38 (m, 4H), 7.06 (dd, 1H, J 8.6, 3.0 Hz), 6.87-6.70 (m, 4H), 5.33 (dd, 1H, J 10.3, 2.1 Hz), 5.01 (bs, 2H), 2.97 (m, 1H), 2.74 (m, 1H), 2.20 (m, 1H), 1.93 (m, 1H).

6-[2-(2-Aminophenyl)chroman-6-yloxy]-pyridin-3-ylamine $^1$H NMR (300 MHz, d$_6$-DMSO) δ: 7.51 (d, 1H, J 2.9 Hz), 7.15-7.18 (m, 1H), 7.05 (dd, 1H, J 8.6, 2.9 Hz), 6.98-7.00 (m, 1H), 6.77 (d, 1H, J 8.6 Hz), 6.73-6.75 (m, 2H), 6.66-6.71 (m, 2H), 6.56-6.61 (m, 1H), 5.11 (dd, 1H, J 10.4, 2.0 Hz), 5.01 (s, 2H), 4.99 (s, 2H), 2.94-2.99 (m, 1H), 2.66-2.74 (m, 1H), 2.06-2.13 (m, 1H), 1.88-1.95 (m, 1H).

6-[2-(3-Aminophenyl)chroman-6-yloxy]-pyridin-3-ylamine $^1$H NMR (300 MHz, d$_6$-DMSO) δ: 7.51 (d, 1H, J 2.8 Hz), 7.05 (dd, 1H, J 8.6, 2.8 Hz), 7.01 (t, 1H, J 15.4, 7.7 Hz), 6.70-6.78 (m, 3H), 6.68 (d, 1H, J 8.6 Hz), 6.63 (s, 1H), 6.54 (d, 1H, J 7.7 Hz), 6.50 (d, 1H, J 8.6 Hz), 5.06 (s, 2H), 4.98 (s, 2H), 4.90 (dd, 1H, J 10.0, 2.2 Hz), 2.85-2.96 (m, 1H), 2.62-2.74 (m, 1H), 2.05-2.11 (m, 1H), 1.89-1.95 (m, 1H).

6-[2-(4-Aminophenyl)chroman-6-yloxy]-pyridin-3-ylamine $^1$H NMR (400 MHz, d$_6$-DMSO) δ: 7.50 (d, 1H, J 2.9 Hz), 7.07 (d, 2H, 8.4 Hz), 7.04 (dd, 1H, J 8.6, 2.9 Hz), 6.71 (s, 3H), 6.68 (d, 1H, J 8.6 Hz), 6.56 (d, 2H, J 8.4 Hz), 5.07 (s, 2H), 4.99 (s, 2H), 4.84 (dd, 1H, J 9.7, 2.3 Hz), 2.86-2.95 (m, 1H), 2.66-2.71 (m, 1H), 1.95-2.05 (m, 2H).

6-[2-(3-Methoxyphenyl)chroman-6-yloxy]pyridin-3-ylamine ORM-10684

$^1$H NMR (400 MHz, d$_6$-DMSO) δ: 7.51 (d, 1H, J 3.0 Hz), 7.31 (t, 1H, J 15.8, 7.9 Hz), 7.04 (dd, 1H, J 8.7, 3.0 Hz), 6.99-7.02 (m, 1H), 6.99 (d, 1H, J 2.6 Hz), 6.90 (dd, 1H, J 8.9, 2.6 Hz), 6.79-6.81 (m, 1H), 6.72-6.74 (m, 2H), 6.69 (d, 1H, J 8.9 Hz), 5.06 (dd, 1H, J 9.9, 2.2 Hz), 4.50 (s, 2H), 3.77 (s, 3H), 2.88-2.95 (m, 1H), 2.66-2.71 (m, 1H), 2.12-2.17 (m, 1H), 1.94-2.00 (m, 1H).

6-(5-Aminopyridin2-yloxy)-2-phenylchroman-4-one $^1$H NMR (400 MHz, CD$_3$OD) δ: 7.62 (d, 1H, J 3.0 Hz), 7.51-7.49 (m, 2H), 7.42-7.33 (m, 3H), 7.25-7.18 (m, 3H), 7.06 (d, 1H, J 8.8 Hz), 6.76 (d, 1H, J 8.6 Hz), 5.50 (dd, 1H, J 13.0, 2.9 Hz), 3.08 (dd, 1H, −17.0, 13.0 Hz), 2.82 (dd, 1H, J −17.0, 2.9 Hz).

6-(2-Phenyl-2,3-dihydrobenzo[1,4]oxathiin-6-yloxy)pyridin-3-ylamine hydrochloride $^1$H NMR (400 MHz, CDCl$_3$) δ: 8.20 (d, 1H, J 2.1 Hz), 7.87 (dd, 1H, J 8.9, 2.1 Hz), 7.41-7.44 (m, 4H), 7.37-7.40 (m, 1H), 6.98 (d, 1H, J 8.9 Hz), 6.97 (d, 1H, J 8.8 Hz), 6.93 (d, 1H, J 2.7 Hz), 6.80 (dd, 1H, J 8.8, 2.7 Hz), 5.20 (dd, 1H, J 9.6, 1.9 Hz), 3.30 (dd, 1H, 13.2, 9.6 Hz), 3.12 (dd, 1H, 13.2, 1.9 Hz).

6-(5-Aminopyridin-2-yloxy)-2-phenylchromen-4-one $^1$H-NMR (300 MHz; d$_6$-DMSO) δ: 8.14-8.10 (m, 2H), 7.63-7.51 (m, 5H), 7.42 (d, 1H, J 2.9 Hz) 7.14 (dd, 1H, J 8.6, 2.9 Hz), 7.03 (s, 1H), 6.89 (d, 1H, J 8.6 Hz), 5.19 (s, 2H).

6-{2-[3-(Pyridin-2-yloxy)phenyl]chroman-6-yloxy}pyridin-3-ylamine $^1$H NMR (400 MHz, d$_6$-DMSO) δ: 8.16 (dd, 1H, J 4.7, 1.3 Hz), 7.86 (ddd, 1H, H 8.7, 6.9, 2.0 Hz), 7.51 (d, 1H, J 2.8 Hz), 7.44 (t, 1H, J 7.8 Hz), 7.29 (d, 1H, J 7.8 Hz), 7.19 (s, 1H), 7.13 (dd, 1H, J 6.9, 5.2 Hz), 7.09-7.03 (m, 3H), 6.81-6.71 (m, 3H), 6.69 (d, 1H, J 8.7 Hz), 5.11 (d, 1H, J 9.8 Hz), 4.99 (s, 2H), 2.89 (m, 1H), 2.68 (m, 1H), 2.17 (m, 1H), 1.97 (m, 1H).

Using the same procedure described for 5-amino-2-(2-phenylchroman-6-yloxy)pyridine but replacing 5-nitro-2-(2-phenylchroman-6-yloxy)-pyridine by:

2-[2-(3,4-difluorophenyl)chroman-6-yloxy]-5-nitropyridine,
5-nitro-2-[2-(2-trifluoromethylphenyl)chroman-6-yloxy]pyridine,
2-[2-(3-chloro-4-fluorophenyl)chroman-6-yloxy]-5-nitropyridine,
2-[2-(3-chlorophenyl)chroman-6-yloxy]-5-nitropyridine,
2-[2-(2,4-dichlorophenyl)chroman-6-yloxy]-5-nitropyridine,
2-[2-(3-bromophenyl)chroman-6-yloxy]-5-nitropyridine,
2-[2-(4-ethylphenyl)chroman-6-yloxy]-5-nitropyridine,
2-(3-methyl-2-phenylchroman-6-yloxy)-5-nitropyridine,
5-nitro-2-(2-phenylchroman-7-yloxy)-pyridine,
7-(5-nitropyridin-2-yloxy)-2-phenylchroman-4-one,
3-methyl-6-(5-nitropyridin-2-yloxy)-2-phenylchroman-4-one,
2-(2,3-dihydro-2-phenyl-benzo[1,4]dioxin-6-yloxy)-5-nitropyridine,
5-nitro-2-(6-phenyl-5,6,7,8-tetrahydronaphthalen-2-yloxy)pyridine,
6-(5-nitropyridin-2-yloxy)-2-phenyl-3,4-dihydro-2H-naphthalen-1one,
2-[3-(3-fluorophenyl)chroman-7-yloxy]-5-nitropyridine,
2-(3-phenylchroman-7-yloxy)-5-nitropyridine,
5-nitro-2-(2-phenylindan-5-yloxy) pyridine,
5-Nitro-2-(2-phenylindan-5-yloxy) pyridine there can be obtained:

6-[2-(3,4-Difluorophenyl)chroman-6-yloxy]pyridin-3-ylamine,
6-[2-(2-Trifluoromethylphenyl)chroman-6-yloxy]pyridin-3-ylamine,
6-[2-(3-Chloro-4-fluorophenyl)chroman-6-yloxy]pyridin-3-ylamine,
6-[2-(3-Chlorophenyl)chroman-6-yloxy]pyridin-3-ylamine,
6-[2-(2,4-Dichlorophenyl)chroman-6-yloxy]pyridin-3-ylamine,
6-[2-(3-Bromophenyl)chroman-6-yloxy]pyridin-3-ylamine,
6-[2-(4-Ethylphenyl)chroman-6-yloxy]pyridin-3-ylamine,
6-(3-Methyl-2-phenylchroman-6-yloxy)pyridin-3-ylamine,
5-Amino-2-(2-phenylchroman-7-yloxy)pyridine,
7-(5-Aminopyridin2-yloxy)-2-phenylchroman-4-one,
6-(5-Aminopyridin-2-yloxy)-3-methyl-2-phenylchroman-4-one,
6-(2-Phenyl-2,3-dihydrobenzo[1,4]dioxin-6-yloxy)pyridin-3-ylamine,
6-(6-Phenyl-5,6,7,8-tetrahydronaphthalen-2-yloxy)pyridin-3-ylamine,
6-(5-Aminopyridin-2-yloxy)-2-phenyl-3,4-dihydro-2H-naphthalen-1-one,
6-[3-(3-Fluorophenyl)chroman-7-yloxy]pyridin-3-ylamine,
6-(3-Phenylchroman-7-yloxy)-pyridin-3-ylamine,
6-(2-Phenylindan-5-yloxy)-pyridin-3-ylamine, respectively.

Example 11

Intermediates

3-Pyridinyloxybenzaldehyde Intermediates

3-(5-Chloropyridin-2-yloxy)benzaldehyde

3-Hydroxybenzaldehyde (3.0 g) was dissolved in dry DMF (30 ml) under nitrogen. Potassium tert-butoxide (3.0 g) was added in to a solution and the resulting mixture was stirred for 30 minutes. 2,5-Dichloropyridine (3,6 g) was added and the mixture was stirred at 120° C. for 1.5 hours. The reaction mixture was allowed to cool to room temperature and 1 M HCl-solution was added and it was extracted with ethyl acetate. The combined organic phases were washed with water and saturated NaCl-solution and dried. The product was purified by column chromatography using heptane-ethyl acetate (3:1) as an eluant. $^1$H NMR (400 MHz, d$_6$-DMSO) δ: 10.01 (s, 1H), 8.22 (d, 1H, J 2.6 Hz), 8.01 (dd, 1H, J 8.7, 2.6 Hz), 7.79 (d, 1H, J 7.6 Hz), 7.69-7.65 (m, 2H), 7.52 (m, 1H), 7.20 (d, 1H, J 8.7 Hz).

Similarly starting from 2-chloropyridin there was obtained:

3-(pyridin-2-yloxy)benzaldehyde $^1$H NMR (400 MHz, d$_6$-DMSO) δ: 10.01 (s, 1H), 8.17 (dd, 1H, J 5.0, 1.7 Hz), 7.90 (ddd, 1H, J 8.5, 6.8, 1.9 Hz), 7.77 (d, 1H, J 7.8 Hz), 7.66, (t, 1H, J 7.8 Hz), 7.63 (m, 1H), 7.50 (m, 1H), 7.18 (dd, 1H, J 6.9, 5.0 Hz), 7.13 (d, 1H, 8.3 Hz).

Example 12

6-(5-Nitropyridin-2-yloxy)-2-phenylchromen-4-one 6-(5-Nitropyridin-2-yloxy)-2-phenylchromen-4-one was prepared as described for 5-nitro-2-(2-phenylchroman-6-yloxy)pyridine in Example 1(b) starting from 500 mg of 6-hydroxyflavone. The product was recrystallised from a mixture of 2-propanol and acetone. $^1$H NMR (300 MHz, d$_6$-DMSO) δ: 9.04 (d, 1H, J 2.9 Hz), 8.67 (dd, 1H, J 9.0, 2.9 Hz), 8.16-8.13 (m, 2H), 7.95 (d, 1H, J 9.0 Hz), 7.82 (d, 1H, J 2.9 Hz), 7.63 (dd, 1H, J 9.1, 2.9 Hz), 7.64-7.61 (m, 3H), 7.38 (d, 1H, J 9.1 Hz), 7.09 (s, 1H).

Example 13

2-[2-(3-(5-Nitropyridin-2-yloxy)phenyl)chroman-6-yloxy]-5-nitropyridine and its a) 6-Hydroxy-2-(3-hydroxyphenyl)chroman-4-one (Intermediate)

6-Hydroxy-2-(3-hydroxyphenyl)chroman-4-one was prepared as described for 6-hydroxy-2-(4-fluorophenyl)chroman-4-one in Example 2(a) but starting from 3-hydroxybenzaldehyde. The product was recrystallised from ethanol. $^1$H NMR (400 MHz, d$_6$-DMSO) δ: 9.50 (bs, 1H), 9.41 (bs, 1H), 7.22-7.17 (m, 1H), 7.11 (d, 1H, J 3.0 Hz), 7.03 (dd, 1H J 3.0, 8.9 Hz), 6.64 (d, 1H, J 8.9 Hz), 6.92-6.90 (m, 2H), 6.76-6.73 (m, 1H), 5.46 (dd, 1H J 2.9, 12.7 Hz), 3.09 (dd, 1H, J 12.7, 16.9 Hz), 2.75 (dd, 1H, J 2.9, 16.9 Hz).

Similarly there were obtained:

6-Hydroxy-2-(4-hydroxyphenyl)chroman-4-one $^1$H NMR (400 MHz, d$_6$-DMSO) δ: 9.54 (bs, 1H), 9.38 (bs, 1H), 7.34-7.31 (m, 2H), 7.10 (d, 1H, J 3.0 Hz), 7.02 (dd, 1H J 3.0, 8.8 Hz), 6.91 (d, 1H, J 8.8 Hz), 6.80-6.77 (m, 2H), 5.40 (dd, 1H J 2.7, 13.1 Hz), 3.17 (dd, 1H, J 13.2, 16.9 Hz), 2.68 (dd, 1H, J 2.7, 16.9 Hz).

6-Hydroxy-2-(3-benzyloxyphenyl)chroman-4-one $^1$H NMR (400 MHz, $d_6$-DMSO) δ: 9.41 (bs, 1H), 7.50-7.30 (m, 6H), 7.20 (s, 1H), 7.12-7.08 (m, 2H), 7.05-7.00 (m, 2H), 6.95 (d, 1H, J 8.9 Hz), 5.52 (dd, 1H J 2.9, 12.9 Hz), 5.12 (s, 2H), 3.16 (dd, 1H, J 12.9, 16.9 Hz), 2.78(dd, 1H, J 2.9, 16.9 Hz).

2-[3-(5-Chloropyridin-2-yloxy)phenyl]-6-hydroxy-chroman-4-one $^1$H NMR (400 MHz, $d_6$-DMSO) δ: 9.52 (bs, 1H), 8.22 (d, 1H, J 2.6 Hz), 7.97 (dd, 1H, J 8.8, 2.6 Hz), 7.47 (t, 1H, J 7.7 Hz), 7.39 (d, 1H, J 7.7 Hz), 7.32 (s, 1H), 7.16-7.10 (m, 3H), 7.04 (dd, 1H, J 8.8, 3.0 Hz), 6.96 (d, 1H, J 8.8 Hz), 5.57 (dd, 1H, J 13.0, 2.7 Hz), 3.17 (dd, 1H, J −16.8, 13.0 Hz), 2.80 (dd, 1H, J −16.8, 2.7 Hz).

6-Hydroxy-2-[3-(pyridin-2-yloxy)phenyl]chroman-4-one $^1$H NMR (300 MHz, $d_6$-DMSO) δ: 8.16 (ddd, 1H, J 5.0, 2.0, 1.8 Hz), 7.86 (m, 1H), 7.46 (t, 1H, J 7.8 Hz), 7.37 (d, 1H, J 7.8 Hz), 7.30 (d, 1H J 2.0 Hz), 7.16-7.10 (m, 3H), 7.06-7.02 (m, 2H), 6.94 (d, 1H, J 8.8 Hz), 5.57 (dd, 1H, J 12.9, 2.9 Hz), 3.17 (dd, 1H, J −16.8, 12.9 Hz), 2.80 (dd, 1H, J −16.8, 2.9 Hz).

b) 2-(3-Hydroxyphenyl)chroman-4,6-diol (Intermediate)

2-(3-Hydroxyphenyl)chroman-4,6-diol was prepared as described for 2-(4-fluorophenyl)chroman-4,6-diol in Example 2(b) but starting from 6-hydroxy-2-(3-hydroxyphenyl)chroman-4-one. $^1$H NMR (400 MHz, $d_6$-DMSO) δ: 9.43 (bs, 1H), 8.88 (bs, 1H), 7.19-7.15 (m, 1H), 6.87 (d, 1H, J 2.7 Hz), 6.84-6.82 (m, 2H), 6.72-6.69 (m, 1H), 6.58 (d, 1H, J 8.7 Hz), 6.53 (dd, 1H, J 2.7, 8.7), 5.01 (d, 1H, J 11.3 Hz), 4.86 (dd, 1H, J 6.2, 10.8 Hz), 2.25-2.19 (m, 1H), 1.88-1.75 (m, 1H).
Similarly there were obtained:

2-(4-Hydroxyphenyl)chroman-4,6-diol $^1$H NMR (400 MHz, $d_6$-DMSO) δ: 9.41 (bs, 1H), 8.79 (bs, 1H), 7.23-7.21 (m, 2H), 6.87 (s, 1H), 6.77-6.74 (m, 2H), 6.53 (m, 2H), 5.37 (d, 1H, J 7.0 Hz), 4.97 (d, 1H, J 11.6 Hz), 4.85-4.82 (m, 1H), 2.20-2.15 (m, 1H), 1.95-1.85 (m, 1H).

2-(3-Benzyloxyphenyl)chroman-4,6-diol $^1$H NMR (400 MHz, $d_6$-DMSO) δ: 8.81 (bs, 1H), 7.47-7.28 (m, 6H), 7.09 (s, 1H), 7.02 (d, 1H, J 7.9 Hz), 6.97 (dd, 1H, J 2.4, 7.9 Hz), 6.88 (d, 1H, J 2.8 Hz), 6.59 (d, 1H, J 8.7 Hz), 6.54 (dd, 1H, J 2.8, 8.7), 5.40 (d, 1H, J 6.2 Hz), 5.12 (s, 2H), 5.08 (d, 1H, J 10.9 Hz), 4.88-4.85 (m, 1H), 2.28-2.23 (m, 1H), 1.92-1.77 (m, 1H).

2-[3-(5-Chloropyridin-2-yloxy)phenyl]chroman-4,6-diol $^1$H NMR (400 MHz, $d_6$-DMSO) δ: 8.82 (s, 1H), 8.22 (d, 1H, J 2.6 Hz), 7.97 (dd, 1H, J 8.6, 2.6 Hz), 7.45 (t, 1H, J 7.9 Hz), 7.31 (d, 1H, J 7.9 Hz), 7.20 (d, 1H, J 1.7 Hz), 7.12 (d, 1H, J 8.6 Hz), 7.11 (dd, 1H, J 7.9, 1.7 Hz), 6.87 (d, 1H, J 2.6 Hz), 6.59 (d, 1H, J 8.6 Hz), 6.53 (dd, 1H, J 8.6, 2.6 Hz), 5.41 (bs, 1H), 5.14 (d, 1H, J 12.9 Hz), 4.86 (m, 1H) 2.29 (m, 1H), 1.87 (m, 1H).

2-[3-(Pyridin-2-yloxy)phenyl]chroman-4,6-diol $^1$H NMR (400 MHz, $d_6$-DMSO) δ: 8.82 (s, 1H), 8.17 (m, 1H), 7.86 (m, 1H), 7.43 (t, 1H, J 7.8 Hz), 7.29 (d, 1H, J 7.8 Hz), 7.18 (s, 1H), 7.15-7.04 (m, 3H), 6.87 (d, 1H, J 2.7 Hz), 6.59 (d, 1H, J 8.7 Hz), 6.53 (dd, 1H, J 8.7, 2.7 Hz), 5.40 (d, 1H, J 7.0 Hz), 5.14 (d, 1H, J 11.6 Hz), 4.86 (m, 1H) 2.29 (m, 1H), 1.88 (m, 1H).

c) 2-(3-Hydroxyphenyl)chroman-6-ol (Intermediate)

2-(3-Hydroxyphenyl)chroman-6-ol was prepared as described for 2-(4-fluorophenyl)chroman-6-ol in Example 2(c) but starting from 2-(3-hydroxyphenyl)chroman-4,6-diol.
$^1$H NMR (400 MHz, $d_6$-DMSO) δ: 9.38 (s, 1H), 8.77 (s, 1H), 7.17-7.13 (m, 1H), 6.82-6.79 (m, 2H), 6.70-6.67 (m, 1H), 6.62 (d, 1H, J 8.6 Hz), 6.52-6.47 (m, 2H), 4.89 (dd, 1H, J 2.1, 9.9 Hz), 2.86-2.82 (m, 1H), 2.65-2.59 (m, 1H), 2.09-2.04 (m, 1H), 1.91-1.85 (m, 1H).
Similarly there were obtained:

2-(3-Benzyloxyphenyl)chroman-6-ol $^1$H NMR (400 MHz, $d_6$-DMSO) δ: 8.77 (s, 1H), 7.46-7.26 (m, 6H), 7.06 (s, 1H), 7.00-6.93 (m, 2H), 6.63 (d, 1H, J 8.5 Hz), 6.52-6.47 (m, 2H), 5.10 (s, 2H), 4.96 (dd, 1H, J 1.8, 9.8 Hz), 2.91-2.82 (m, 1H), 2.67-2.59 (m, 1H), 2.12-2.07 (m, 1H), 1.99-1.87 (m, 1H).

2-[3-(5-Chloropyridin-2-yloxy)phenyl]chroman-6-ol $^1$H NMR (300 MHz, $d_6$-DMSO) δ: 8.75 (s, 1H), 8.21 (d, 1H, J 2.6 Hz), 7.95 (dd, 1H, J 8.7, 2.6 Hz), 7.43 (t, 1H, J 7.8 Hz), 7.28 (d, 1H, J 7.8 Hz), 7.18 (d, 1H, J 1.9 Hz), 7.11-7.07 (m, 2H), 6.61-6.48 (m, 3H), 5.01 (dd, 1H, J 9.8, 2.0 Hz), 2.87 (m, 1H) 2.62 (m, 1H), 2.13 (m, 1H), 1.93 (m, 1H).

2-[3-(Pyridin-2-yloxy)phenyl]chroman-6-ol $^1$H NMR (400 MHz, $d_6$-DMSO) δ: 8.81 (bs, 1H), 8.17 (m, 1H), 7.85 (m, 1H), 7.42 (t, 1H, J 7.9 Hz), 7.26 (d, 1H, J 7.9 Hz), 7.16-7.12 (m, 2H), 7.07-7.02 (m, 2H), 6.63 (d, 1H, J 8.2 Hz), 6.57-6.48 (m, 2H), 5.01 (d, 1H, J 8.5 Hz), 2.88 (m, 1H) 2.63 (m, 1H), 2.13 (m, 1H), 1.93 (m, 1H).

d) 2-[2-(3-(5-Nitropyridin-2-yloxy)phenyl)chroman-6-yloxy]-5-nitropyridine

2-[2-(3-(5-Nitropyridin-2-yloxy)phenyl)chroman-6-yloxy]-5-nitropyridine was prepared as described for 5-nitro-2-(2-phenylchroman-6-yloxy)pyridine in Example 1 (b) but starting from 2-(3-hydroxyphenyl)chroman-6-ol and using 210 mol-% of 2-chloro-5-nitropyridine. $^1$H NMR (400 MHz, $d_6$-DMSO) δ: 9.05 (d, 1H, J 2.9 Hz), 9.03 (d, 1H, J 2.9 Hz), 8.64 (dd, 1H, J 2.9, 9.1 Hz), 8.60 (dd, 1H, J 2.9, 9.1 Hz), 7.52 (t, 1H, J 7.8 Hz), 7.41 (d, 1H, J 7.8 Hz), 7.33-7.31 (m, 1H), 7.28 (d, 1H, J 7.8 Hz), 7.23-7.18 (m, 2H) 7.01-6.90 (m, 3H), 5.20 (dd, 1H, J 2.1, 10.1 Hz), 3.07-2.92 (m, 1H), 2.80-2.70 (m, 1H), 2.30-2.18 (m, 1H), 2.10-1.98 (m, 1H).
Using only 100 mol-% of 2-chloro-5-nitropyridine there were obtained:

5-Nitro-2-[2-(3-benzyloxyphenyl)chroman-6-yloxy]pyridine $^1$H NMR (300 MHz, $d_6$-DMSO) δ: 9.03 (d, 1H, J 2.9 Hz), 8.59 (dd, 1H, J 2.9, 9.1 Hz), 7.47-7.29 (m, 6H), 7.19 (d, 1H, J 9.1 Hz), 7.10 (s, 1H), 7.05-6.92 (m, 5H), 5.14-5.10 (m, 3H), 3.00-2.88 (m, 1H), 2.75-2.69 (m, 1H), 2.20-2.14 (m, 1H), 2.07-1.95 (m, 1H).

5-Nitro-2-{2-[3-(5-chloropyridin-2-yloxy)phenyl]
chroman-6-yloxy}pyridine $^1$H NMR (300 MHz, d$_6$-DMSO) δ: 9.02 (d, 1H, J 2.9 Hz), 8.59 (dd, 1H, J 9.1, 2.9 Hz), 8.22 (d, 1H, J 2.8 Hz), 7.97 (dd, 1H, J 8.7, 2.8 Hz), 7.46 (t, 1H, J 7.8 Hz), 7.33 (d, 1H, J 7.8 Hz), 7.23, (s, 1H), 7.19 (d, 1H, J 9.1 Hz), 7.13-7.10 (m, 2H), 6.99-6.89 (m, 3H), 5.18 (d, 1H, J 8.0 Hz), 2.97 (m, 1H), 2.75 (m, 1H), 2.21 (m, 1H), 2.01 (m, 1H).

5-Nitro-2-{2-[3-(pyridin-2-yloxy)phenyl]chroman-6-
yloxy}pyridine $^1$H NMR (400 MHz, d$_6$-DMSO) δ: 9.04 (d, 1H, J 2.7 Hz), 8.59 (dd, 1H, J 9.1, 2.7 Hz), 8.17 (m, 1H), 7.86 (m, 1H), 7.45 (t, 1H, J 7.8 Hz), 7.31 (d, 1H, J 7.8 Hz), 7.21, (s, 1H), 7.20 (d, 1H, J 9.1 Hz), 7.13 (m, 1H), 7.09 (m, 1H), 7.06 (8.6 Hz), 7.04 (2.5 Hz), 6.96 (dd, 1H, J 8.6, 2.5 Hz), 5.18 (d, 1H, J 8.8 Hz), 2.98 (m, 1H), 2.72 (m, 1H), 2.21 (m, 1H), 2.02 (m, 1H).

Example 14

6-(5-Nitropyridin-2-yloxy)-2-[3-(5-nitropyridin-2-
yloxy)phenyl]chroman-4-ol and its a) 6-(5-Nitropyridin-2-yloxy)-2-[3-(5-nitropyridin-2-
yloxy)phenyl]chroman-4-ol 6-(5-Nitropyridin-2-yloxy)-2-[3-(5-nitropyridin-2-yloxy)phenyl]chroman-4-ol was prepared as described for 5-nitro-2-(2-phenylchroman-6-yloxy)pyridine in Example 1 (b) but starting from 2-(3-hydroxyphenyl)chroman-4,6-diol and using 210 mol-% of 2-chloro-5-nitropyridine. $^1$H NMR (400 MHz, d$_6$-DMSO) δ: 9.06 (d, 1H, J 2.8 Hz), 9.03 (d, 1H, J 2.8 Hz), 8.64 (dd, 1H, J 2.8, 9.1 Hz), 8.61 (dd, 1H, J 2.8, 9.1 Hz), 7.54 (t, 1H, J 7.9 Hz), 7.43 (d, 1H, J 7.9 Hz), 7.36 (s, 1H), 7.30 (d, 1H, J 9.1 Hz), 7.25-7.21 (m, 3H) 7.01 (dd, 1H, J 2.9, 8.7 Hz), 6.89 (d, 1H, J 8.7 Hz), 5.67 (d, 1H, J 6.4 Hz), 5.36 (d, 1H, J 10.8 Hz), 5.01-4.95 (m, 1H), 2.41-2.36 (m, 1H), 2.02-1.92 (m, 1H).

Similarly there was obtained:

b) 6-(5-Nitropyridin-2-yloxy)-2-[4-(5-nitropyridin-2-
yloxy)phenyl]chroman-4-ol $^1$H NMR (400 MHz, d$_6$-DMSO) δ: 9.05-9.04 (m, 2H, major & minor), 8.66-8.60 (m, 2H, major & minor), 7.61-7.58 (m, 2H, major & minor), 7.31-7.21 (m, 5H, major & minor), 7.10 (dd, 1H, J 2.9, 8.8 Hz, minor), 7.03 (dd, 1H, J 3, 8.8 Hz, major), 6.97 (d, 1H, J 8.8 Hz, minor) 6.89 (d, 1H, J 8.8 Hz, major), 5.68 (d, 1H, J 6.4 Hz, major), 5.63 (d, 1H, J 4.7 Hz, minor), 5.37-5.30 (m, 1H, major & minor), 5.04-4.97 (m, 1H, major), 4.69-4.65 (m, 1H, minor), 2.41-2.36 (m, 1H, major), 2.21-2.15 (m, 2H, major & minor), 2.07-1.98 (m, 1H, major).

Example 15

2-{2-[4-(5-Nitropyridin-2-yloxy)phenyl]chroman-6-
yloxy}-5-nitropyridine

2-{2-[4-(5-Nitropyridin-2-yloxy)-phenyl]-chroman-6-yloxy}-5-nitropyridine was prepared as described for 2-(4-fluorophenyl)chroman-6-ol in Example 2(c) but starting from 6-(5-nitropyridin-2-yloxy)-2-[4-(5-nitropyridin-2-yloxy)phenyl]-chroman-4-ol. $^1$H NMR (400 MHz, d$_6$-DMSO) δ: 9.05 (d, 2H, J 2.9 Hz), 8.65-8.58 (m, 2H), 7.58-7.55 (m, 2H), 7.30-7.26 (m, 3H), 7.20 (d, 1H, J 9.1 Hz), 7.03-6.91 (m, 3H) 5.20 (dd, 1H, J 2.0, 10.1 Hz), 3.06-2.97 (m, 1H), 2.81-2.75 (m, 1H), 2.26-2.21 (m, 1H), 2.11-2.02 (m, 1H).

Example 16

6-[2-(3-(5-Aminopyridin-2-yloxy)phenyl)chroman-
6-yloxy]-pyridin-3-ylamine and thereof 6-[2-(3-(5-Aminopyridin-2-yloxy)phenyl)chroman-6-yloxy]-pyridin-3-ylamine was prepared as described for 5-amino-2-(2-phenylchroman-6-yloxy)pyridine in Example 10 but starting from 2-[2-(3-(5-nitropyridin-2-yloxy)phenyl)chroman-6-yloxy]-5-nitropyridine. Product was isolated as its dihydrochloride salt. $^1$H NMR (300 MHz, d$_6$-DMSO) δ: 8.12 (m, 2H), 7.78 (m, 1H), 7.45 (t, 1H, J 7.8 Hz), 7.31 (d, 1H, J 7.2 Hz), 7.21 (s, 1H), 7.13-7.04 (m, 3H), 6.91-6.87 (m, 3H), 5.15 (d, 1H, J 9.8 Hz), 3.02-2.91 (m, 1H), 2.76-2.70 (m, 1H), 2.23-2.17 (m, 1H), 2.05-1.93 (m, 1H).

Similarly there were obtained:

6-[2-(3-Benzyloxyphenyl)chroman-6-yloxy]pyridin-
3-ylamine hydrochloride $^1$H NMR (400 MHz, d$_6$-DMSO) δ: 7.85 (s, 1H), 7.47-7.29 (m, 6H), 7.09 (s, 1H), 7.02 (d, 1H, J 7.4 Hz), 6.98 (dd, 1H, J 2.3, 8.2 Hz), 6.91 (d, 1H, J 8.7 Hz), 6.85-6.81 (m, 4H), 5.12 (s, 2H), 5.09 (d, 1H, J 9.5 Hz), 2.96-2.89 (m, 1H), 2.72-2.67 (m, 1H) 2.20-2.14 (m, 1H), 2.03-1.97 (m, 1H).

6-(5-Aminopyridin-2-yloxy)-2-[3-(5-aminopyridin-
2-yloxy)phenyl]chroman-4-ol dihydrochloride $^1$H NMR (400 MHz, d$_6$-DMSO) δ: 8.15 (d, 2H, J 2.6 Hz), 7.82 (dd, 2H, J 2.6, 8.8 Hz), 7.47 (t, 1H, 7.9 Hz), 7.35 (d, 1H, J 7.9 Hz), 7.24 (s, 1H), 7.19-7.08 (m, 4H), 6.94 (dd, 1H, J 2.8, 8.8 Hz), 6.84 (d, 1H, 8.8 Hz), 5.30 (d, 1H, J 10.9 Hz), 4.96 (dd, 1H, J 6.1, 10.7 Hz), 2.38-2.32 (m, 1H), 1.98-1.88 (m, 1H).

Example 17

3-[6-(5-Aminopyridin-2-yloxy)chroman-2-yl]phenol 2.15 g of 5-nitro-2-[2-(3-benzyloxyphenyl)chroman-6-yloxy]pyridine was dissolved to 600 ml of ethanol and 430 mg g of 10% palladium on charcoal was added under inert atmosphere. Starting material was hydrogenated at room temperature to give quantitative yield of 3-[6-(5-aminopyridin-2-yloxy)chroman-2-yl]phenol $^1$H NMR (400 MHz, d$_6$-DMSO) δ: 9.50 (bs, 1H), 7.52 (d, 1H, J 3.0 Hz), 7.17 (t, 1H, J 8.1 Hz), 7.05 (dd, 1H, J 3.0, 8.6 Hz), 6.84-6.68 (m, 7H), 5.01-4.99 (m, 3H), 2.91-2.86 (m, 1H), 2.70-2.63 (m, 1H), 2.14-2.08 (m, 1H), 1.96-1.89 (m, 1H).

Example 18

2-Acetylamino-N-[6-(2-phenylchroman-6-yloxy)-
pyridin-3-yl]-acetamide

5-Amino-2-(2-phenylchroman-6-yloxy)-pyridine (500 mg) and N-acetyl-glycine (275 mg) was dissolved in 35 ml of methylene chloride. 1-(3-dimethylamino-propyl)-3-ethylcarbodiimide hydrochloride (450 mg) was added. The mixture was stirred at room temperature for 6 hours. Reaction was quenched with addition of water and formed precipitate was filtered. $^1$H-NMR (400 MHz; d$_6$-DMSO) δ: 10.1 (s, 1H), 8.30 (d, 1H, J 2.7 Hz), 8.21 (t, 1H, J 5.7 Hz), 8.00 (dd, 1H, J 2.7, 8.9

Hz), 7.47-7.30 (m, 5H), 6.95 (d, 1H, J 8.9 Hz), 6.87-6.84 (m, 3H), 5.12 (dd, 1H, J 1.90, 10.0 Hz), 3.86 (d, 2H, J 5.7 Hz), 3.00-2.92 (m, 1H), 2.75-2.70 (m, 1H), 2.19-2.14 (m, 1H), 2.03-1.97 (m, 1H).

Using the same procedure described for 2-acetylamino-N-[6-(2-phenylchroman-6-yloxy)-pyridin-3-yl]-acetamide above but replacing 5-amino-2-(2-phenylchroman-6-yloxy) pyridine by:

6-[2-(4-Fluorophenyl)chroman-6-yloxy]pyridin-3-ylamine,
6-[2-(3-fluorophenyl)chroman-6-yloxy]-pyridin-3-ylamine,
6-[2-(2-Fluorophenyl)chroman-6-yloxy]-pyridin-3-ylamine,
6-[2-(2,3-Difluorophenyl)chroman-6-yloxy]-pyridin-3-ylamine,
6-[2-(2,4-Difluorophenyl)chroman-6-yloxy]-pyridin-3-ylamine,
6-[2-(2,5-Difluorophenyl)chroman-6-yloxy]-pyridin-3-ylamine
6-[2-(2,6-Difluorophenyl)chroman-6-yloxy]-pyridin-3-ylamine,
6-[2-(3,4-Difluorophenyl)chroman-6-yloxy]pyridin-3-ylamine,
6-[2-(3,5-Difluorophenyl)chroman-6-yloxy]-pyridin-3-ylamine
6-[2-(2-Trifluoromethylphenyl)chroman-6-yloxy]pyridin-3-ylamine,
6-[2-(4-Trifluoromethylphenyl)chroman-6-yloxy]pyridin-3-ylamine,
6-[2-(3-Chloro-4-fluorophenyl)chroman-6-yloxy]pyridin-3-ylamine,
6-[2-(2-Chlorophenyl)chroman-6-yloxy]pyridin-3-ylamine,
6-[2-(3-Chlorophenyl)chroman-6-yloxy]pyridin-3-ylamine,
6-[2-(2,4-Dichlorophenyl)chroman-6-yloxy]pyridin-3-ylamine,
6-[2-(3-Bromophenyl)chroman-6-yloxy]pyridin-3-ylamine,
6-[2-(4-Ethylphenyl)chroman-6-yloxy]pyridin-3-ylamine,
6-[2-(3-Methoxyphenyl)chroman-6-yloxy]pyridin-3-ylamine
6-(3-Methyl-2-phenylchroman-6-yloxy)pyridin-3-ylamine,
5-Amino-2-(2-phenylchroman-7-yloxy)pyridine,
6-(5-Aminopyridin2-yloxy)-2-phenylchroman-4-one,
7-(5-Aminopyridin2-yloxy)-2-phenylchroman-4-one,
6-(5-Aminopyridin-2-yloxy)-3-methyl-2-phenylchroman-4-one,
6-(2-Phenyl-2,3-dihydrobenzo[1,4]dioxin-6-yloxy)pyridin-3-ylamine
6-(6-Phenyl-5,6,7,8-tetrahydronaphthalen-2-yloxy)pyridin-3-ylamine,
6-(5-Aminopyridin-2-yloxy)-2-phenyl-3,4-dihydro-2H-naphthalen-1-one,
6-(2-Phenyl-2,3-dihydrobenzo[1,4]oxathiin-6-yloxy)pyridin-3-ylamine
6-[3-(3-Fluorophenyl)chroman-7-yloxy]pyridin-3-ylamine,
6-(3-Phenylchroman-7-yloxy)-pyridin-3-ylamine,
6-(5-Aminopyridin-2-yloxy)-2-phenylchromen-4-one,
6-(2-Phenylindan-5-yloxy)-pyridin-3-ylamine,
there is obtained:
2-Acetylamino-N-{6-[2-(4-fluorophenyl)chroman-6-yloxy]pyridin-3-yl}acetamide,
2-Acetylamino-N-{6-[2-(3-fluorophenyl)chroman-6-yloxy]pyridin-3-yl}acetamide,
2-Acetylamino-N-{6-[2-(2-fluorophenyl)chroman-6-yloxy]pyridin-3-yl}acetamide,
2-Acetylamino-N-{6-[2-(2,3-difluorophenyl)chroman-6-yloxy]pyridin-3-yl}acetamide,
2-Acetylamino-N-{6-[2-(2,4-difluorophenyl)chroman-6-yloxy]pyridin-3-yl}acetamide,
2-Acetylamino-N-{6-[2-(2,5-difluorophenyl)chroman-6-yloxy]pyridin-3-yl}acetamide,
2-Acetylamino-N-{6-[2-(2,6-difluorophenyl)chroman-6-yloxy]pyridin-3-yl}acetamide,
2-Acetylamino-N-{6-[2-(3,4-difluorophenyl)chroman-6-yloxy]pyridin-3-yl}acetamide
2-Acetylamino-N-{6-[2-(3,5-difluorophenyl)chroman-6-yloxy]pyridin-3-yl}acetamide
2-Acetylamino-N-{6-[2-(2-trifluoromethylphenyl)chroman-6-yloxy]pyridin-3-yl}acetamide,
2-Acetylamino-N-{6-[2-(4-trifluoromethylphenyl)chroman-6-yloxy]pyridin-3-yl}acetamide,
2-Acetylamino-N-{6-[2-(3-chloro-4-fluorophenyl)chroman-6-yloxy]pyridin-3-yl}acetamide,
2-Acetylamino-N-{6-[2-(2-chlorophenyl)chroman-6-yloxy]pyridin-3-yl}acetamide,
2-Acetylamino-N-{6-[2-(3-chlorophenyl)chroman-6-yloxy]pyridin-3-yl}acetamide,
2-Acetylamino-N {6-[2-(2,4-dichlorophenyl)chroman-6-yloxy]pyridin-3-yl}acetamide,
2-Acetylamino-N-{6-[2-(3-bromophenyl)chroman-6-yloxy]pyridin-3-yl}acetamide,
2-Acetylamino-N-{6-[2-(4-ethylphenyl)chroman-6-yloxy]pyridin-3-yl}acetamide,
2-Acetylamino-N-{6-[2-(3-methoxyphenyl)chroman-6-yloxy]pyridin-3-yl}acetamide,
2-Acetylamino-N-{6-(3-methyl-2-phenylchroman-6-yloxy)pyridin-3-yl}acetamide,
2-Acetylamino-N-[6-(2-phenylchroman-7-yloxy)-pyridin-3-yl]-acetamide,
2-Acetylamino-N-[6-(4-oxo-2-phenylchroman-6-yloxy)pyridin-3-yl]acetamide,
2-Acetylamino-N-[6-(4-oxo-2-phenylchroman-7-yloxy)pyridin-3-yl]acetamide,
2-Acetylamino-N-[6-(3-methyl-4-oxo-2-phenylchroman-6-yloxy)pyridin-3-yl]acetamide,
2-Acetylamino-N-[6-(2-phenyl-2,3-dihydrobenzo[1,4]dioxin-6-yloxy)pyridin-3-yl]acetamide,
2-Acetylamino-N-[6-(6-phenyl-5,6,7,8-tetrahydronaphthalen-2-yloxy)-pyridin-3-yl]acetamide,
2-Acetylamino-N-[6-(5-oxo-6-phenyl-5,6,7,8-tetrahydronaphthalen-2-yloxy)pyridin-3-yl]acetamide,
2-Acetylamino-N-[6-(2-phenyl-2,3-dihydrobenzo[1,4]oxathiin-6-yloxy)pyridin-3-yl]acetamide,
2-Acetylamino-N {6-[3-(3-fluorophenyl)chroman-7-yloxy]pyridin-3-yl}acetamide,
2-Acetylamino-N-[6-(3-phenylchroman-7-yloxy)pyridin-3-yl]acetamide,
2-Acetylamino-N-[6-(4-oxo-2-phenyl-4H-chromen-6-yloxy)pyridin-3-yl]acetamide,
2-Acetylamino-N-[6-(2-phenylindan-5-yloxy)pyridin-3-yl]acetamide,
respectively.

Example 19

Piperidine-4-carboxylic acid [6-(2-phenylchroman-6-yloxy)pyridin-3-yl]amide a) 4-[6-(2-Phenylchroman-6yloxy)pyridin-3-ylcarbamoyl]piperidine-1-carboxylic acid tert-butyl ester 5-Amino-2-(2-phenylchroman-6-yloxy)-pyridine (500 mg) and N-(tert-butoxycarbonyl)isonipecotic acid (541 mg) was dissolved in 40 ml of THF. 1-(3-dimethylaminopropyl)-3-ethylcarbodiimide hydrochloride (451 mg) was added. The mixture was refluxed for few hours. Reaction was quenched with addition of water and extracted with ethyl acetate. Combined organic layers were washed with water, saturated sodium carbonate solution, dried with $Na_2SO_4$ and evaporated. $^1$H-NMR (300 MHz; $d_6$-DMSO) δ: 10.0 (s, 1H), 8.31 (d, 1H, J 2.7 Hz), 8.03 (dd, 1H, J 2.7, 8.8 Hz), 7.47-7.33 (m, 5H), 6.92 (d, 1H, J 8.8 Hz), 6.87-6.84 (m, 3H), 5.13 (dd, 1H, J 2.2, 10.1 Hz), 4.04-3.96 (m, 2H), 2.99-2.91 (m, 1H), 2.81-2.69 (m, 3H), 2.20-2.12 (m, 2H), 2.08-1.98 (m, 1H), 1.79-1.74 (m, 3H), 1.50-1.35 (m, 11H).

b) Piperidine-4-carboxylic acid [6-(2-phenylchroman-6-yloxy)pyridin-3-yl]amide

Mixture of 4-[6-(2-Phenyl-chroman-6-yloxy)-pyridin-3-ylcarbamoyl]-piperidine-1-carboxylic acid tert-butyl ester (860 mg) and of 1 M HCl in diethyl ether (13 ml) was stirred at room temperature for 24 hours. Precipitate was filtered and washed with ether. $^1$H-NMR (300 MHz; $d_6$-DMSO) δ: 10.3 (s, 1H), 8.97 (bs, 1H), 8.65 (bs, 1H), 8.34 (d, 1H, J 2.7 Hz), 8.04 (dd, 1H, J 2.7, 8.8 Hz), 7.47-7.33 (m, 5H), 6.94 (d, 1H, J 8.8 Hz), 6.86-6.84 (m, 3H), 5.11 (dd, 1H, J 2.3, 10.0 Hz), 3.35-3.29 (m, 2H), 2.97-2.89 (m, 3H), 2.74-2.66 (m, 2H), 2.19-2.13 (m, 1H), 2.00-1.74 (m, 5H), 1.50-1.35 (m, 11H).

Example 20

2-Amino-N-[6-(2-phenylchroman-6-yloxy)-pyridin-3-yl]propionamide and thereof

2-Amino-N-[6-(2-phenylchroman-6-yloxy)-pyridin-3-yl] propionamide and its derivatives were prepared as described for piperidine-4-carboxylic acid [6-(2-phenyl-chroman-6-yloxy)pyridine-3-yl]amine in Example 19 a) and b) but replacing N-(tert-butoxycarbonyl)isonipecotic acid with (S), (R) or (S,R)-2-tert-butoxycarbonylamino-propionic acid.

a) {1-[6-(2-Phenylchroman-6-yloxy)pyridin-3-ylcarbamoyl]ethyl}carbamic acid tert-butyl ester and its {(S)-1-[6-(2-Phenylchroman-6-yloxy)pyridin-3-ylcarbamoyl]ethyl}carbamic acid tert-butyl ester $^1$H-NMR (300 MHz; $d_6$-DMSO) δ: 10.0 (s, 1H), 8.31 (d, 1H, J 2.7 Hz), 8.03 (dd, 1H, J 2.7, 8.9 Hz), 7.47-7.33 (m, 5H), 6.94 (d, 1H, J 8.9 Hz), 6.87-6.84 (m, 3H), 5.11 (dd, 1H, J 2.0, 10.0 Hz), 4.08 (t, 1H, J 7.1 Hz), 3.00-2.91 (m, 1H), 2.75-2.69 (m, 1H), 2.19-2.04 (m, 1H), 2.02-1.97 (m, 1H), 1.38 (s, 9H), 1.26 (d, 3H, J 7.1 Hz).

{(R)-1-[6-(2-Phenylchroman-6-yloxy)pyridin-3-ylcarbamoyl]ethyl}carbamic acid tert-butyl ester $^1$H NMR (400 MHz, d6-DMSO) d: 10.05 (br s, 1H), 8.31 (d, 1H, J 2.4 Hz), 8.04 (dd, 1H, J 2.4, 8.9 Hz), 7.39-7.46 (m, 3H), 7.32-7.35 (m, 1H), 7.08 (m, 1H), 6.94 (d, 1H, J 8.9 Hz), 6.81-6.86 (m, 3H), 5.12 (d, 1H, J 10.1 Hz), 4.11 (m, 1H), 2.98 (m, 1H), 2.70 (m, 1H), 2.17 (m, 1H), 2.00 (m, 1H), 1.38 (s, 9H), 1.26 (d, 3H, J 7.1 Hz).

b) 2-Amino-N-[6-(2-phenylchroman-6-yloxy)pyridin-3-yl]propionamide and thereof (S)-2-Amino-N-[6-(2-phenylchroman-6-yloxy)pyridin-3-yl]propionamide hydrochloride $^1$H-NMR (400 MHz; $d_6$-DMSO) δ: 10.9 (s, 1H), 8.39 (d, 1H, J 2.5 Hz), 8.05 (dd, 1H, J 2.5, 8.8 Hz), 7.46-7.31 (m, 5H), 7.00 (d, 1H, J 8.8 Hz), 6.88-6.85 (m, 3H), 5.12 (d, 1H, J 8.6 Hz), 4.07 (m, 1H) 3.01-2.92 (m, 1H), 2.75-2.70 (m, 1H), 2.19-2.15 (m, 1H), 2.02-1.97 (m, 1H).

(R)-2-Amino-N-[6-(2-phenylchroman-6-yloxy)pyridin-3-yl]propionamide hydrochloride $^1$H NMR (400 MHz, d6-DMSO) δ: 10.78 (br s, 1H), 8.37 (d, 1H, J 2.8 Hz), 8.27 (br s, 2H), 8.03 (dd, 1H, J 2.8, 8.8 Hz), 7.39-7.46 (m, 4H), 7.34-7.35 (m, 1H), 7.00 (d, 1H, J 8.8 Hz), 6.86-6.88 (m, 3H), 5.12 (d, 1H, J 10.5 Hz), 4.04 (m, 1H), 2.96 (m, 1H), 2.72 (m, 1H), 2.17 (m, 1H), 2.01 (m, 1H), 1.47 (d, 3H, J 6.9 Hz).

Example 21

2-Amino-3-methyl-N-[6-(2-phenylchroman-6-yloxy) pyridin-3-yl]butyramide and its derivatives 2-Amino-3-methyl-N-[6-(2-phenylchroman-6-yloxy)pyridin-3-yl]butyramide and its derivatives were prepared as described for piperidine-4-carboxylic acid [6-(2-phenylchroman-6-yloxy)pyridine-3-yl]amine in Example 19 a) and b) but replacing N-(tert-butoxycarbonyl)isonipecotic acid with (S), (R) or (SR)-2-tert-butoxycarbonylamino-3-methylbutyric acid.

a) {2-Methyl-1-[6-(2-phenylchroman-6-yloxy)pyridin-3-ylcarbamoyl]propyl}carbamic acid tert-butyl ester and its derivatives {(S)-2-Methyl-1-[6-(2-phenylchroman-6-yloxy)pyridin-3-ylcarbamoyl]-propyl}carbamic acid tert-butyl ester $^1$H-NMR (300 MHz; $d_6$-DMSO) δ: 10.1 (s, 1H), 8.32 (d, 1H, J 2.7 Hz), 8.04 (dd, 1H, J 2.7, 8.8 Hz), 7.47-7.33 (m, 5H), 6.94 (d, 1H, J 8.8 Hz), 6.89-6.84 (m, 3H), 5.11 (dd, 1H, J 2.2, 10.0 Hz), 3.91 (t, 1H, J 6.7 Hz), 3.04-2.91 (m, 1H), 2.78-2.69 (m, 1H), 2.21-2.12 (m, 1H), 2.07-1.92 (m, 2H), 1.39 (s, 9H), 0.9 (d, 6H, J 6.7 Hz).

{(R)-2-Methyl-1-[6-(2-phenylchroman-6-yloxy) pyridin-3-ylcarbamoyl]-propyl}carbamic acid tert-butyl ester $^1$H NMR (400 MHz, $d_6$-DMSO) δ: 10.11 (br s, 1H), 8.32 (d, 1H, J 2.3 Hz), 8.04 (dd, 1H, J 2.6, 8.8 Hz), 7.39-7.46 (m, 4H), 7.32-7.35 (m, 1H), 6.95 (d, 1H, J 8.8 Hz), 6.85-6.87(m, 4H), 5.11 (d, 1H, J 8.1 Hz), 3.91 (m, 1H), 2.94 (m, 1H), 2.72 (m, 1H), 2.16 (m, 1H), 1.96-2.03 (m, 2H), 1.39 (s, 9H), 0.90 (d, 6H, J 6.6 Hz).

b) 2-Amino-3-methyl-N-[6-(2-phenylchroman-6-yloxy)pyridin-3-yl]butyramide and its derivatives (S)-2-Amino-3-methyl-N-[6-(2-phenylchroman-6-yloxy)-pyridin-3-yl]butyramide $^1$H-NMR (300 MHz; $d_6$-DMSO) δ: 10.8 (s, 1H), 8.38 (d, 1H, J 2.7 Hz), 8.31 (bs, 3H), 8.05 (dd, 1H, J 2.7, 8.9 Hz), 7.47-7.33 (m, 5H), 7.00 (d, 1H, J 8.9 Hz), 6.98-6.86 (m, 3H), 5.12 (dd, 1H, J 2.2, 10.0 Hz), 3.82-3.78 (m, 1H), 3.08-2.90 (m, 1H), 2.78-2.68 (m, 1H), 2.30-2.10 (m, 2H), 2.07-1.92 (m, 1H), 1.02-0.98 (m, 6H).

(R)-2-Amino-3-methyl-N-[6-(2-phenylchroman-6-yloxy)pyridin-3-yl]butyramide hydrochloride $^1$H NMR (400 MHz, d$_6$-DMSO) δ: 10.97 (br s, 1H), 8.43 (s, 1H), 8.35 (br s, 2H), 8.07 (dd, 1H, J 2.4, 8.7 Hz), 7.39-7.46 (m, 4H), 7.32-7.36 (m, 1H), 7.00 (d, 1H, J 8.7 Hz), 6.86-6.89 (m, 3H), 5.12 (d, 1H, J 10.2 Hz), 3.83 (m, 1H), 2.97 (m, 1H), 2.73 (m, 1H), 2.17-2.23 (m, 2H), 1.99 (m, 1H), 1.00 (d, 6H, J 6.5 Hz).

Example 22

(S)-2-Amino-3-methyl-N-(6-{2-[3-(5-nitropyridin-2-yloxyphenylchroman-6-yloxy}pyridin-3-yl)butyramide hydrochloride a) ((S)-1-{6-[2-(3-Hydroxyphenyl)chroman-6-yloxy]pyridin-3-ylcarbamoyl}-2-methyl-propyl)carbamic acid tert-butyl ester ((S)-1-{6-[2-(3-Hydroxyphenyl)chroman-6-yloxy]pyridin-3-ylcarbamoyl}-2-methyl-propyl)carbamic acid tert-butyl ester was obtained using the same procedure as described in example 21 a) for {(S)-2-Methyl-1-[6-(2-phenylchroman-6-yloxy)-pyridin-3-ylcarbamoyl]propyl}carbamic acid tert-butyl ester, but replacing 5-amino-2-(2-phenylchroman-6-yloxy)pyridine by 3-[6-(5-aminopyridin-2-yloxy)chroman-2-yl]phenol (described in Example 17). $^1$H NMR (400 MHz, d$_6$-DMSO) δ: 10.11 (br s, 1H), 9.42 (br s, 1H), 8.32 (s, 1H); 8.04 (dd, 1H, J 2.2, 8.9 Hz), 7.18 (t, 1H, J 8.2 Hz), 6.95 (d, 1H, J 8.9 Hz), 6.90 (d, 1H, J 8.5 Hz), 6.84-6.86 (m, 6H), 6.71 (d, 1H, J 8.2 Hz), 5.03 (d, 1H, J 9.7 Hz), 3.91 (m, 1H), 2.94 (m, 1H), 2.70 (m, 1H), 2.14 (m, 1H), 1.95 (m, 1H), 1.39 (s, 9H), 0.90 (d, 6H, J 6.6 Hz).

b) [(S)-2-Methyl-1-(6-{2-[3-(5-nitropyridin-2-yloxy)phenyl]chroman-6-yloxy}pyridin-3-ylcarbamoyl)propyl]carbamic acid tert-butyl ester

[(S)-2-Methyl-1-(6-{2-[3-(5-nitropyridin-2-yloxy)phenyl]chroman-6-yloxy}pyridin-3-ylcarbamoyl)propyl]carbamic acid tert-butyl ester was prepared as described for 5-nitro-2-(2-phenylchroman-6-yloxy)pyridine in Example 1 b). $^1$H NMR (400 MHz, d$_6$-DMSO) δ: 10.14 (br s, 1H), 9.05 (d, 1H, J 2.8 Hz), 8.63 (dd, 1H, 2.8, 9.0 Hz), 8.32 (s, 1H), 8.04 (dd, 1H, J 2.6, 8.7 Hz), 7.52 (t, 1H, J 8.0 Hz), 7.40 (d, 1H, J 7.6 Hz), 7.27-7.31 (m, 2H), 7.21 (dd, 1H, J 0.9, 8.0 Hz), 6.94 (d, 1H, J 8.7 Hz), 6.85-6.91 (m, 4H), 5.17 (d, 1H, J 9.8 Hz), 3.91 (m, 1H), 2.94 (m, 1H), 2.73 (m, 1H), 2.21 (m, 1H), 2.02 (m, 1H), 1.39 (s, 9H), 0.89 (d, 6H, J 6.6 Hz).

c) (S)-2-Amino-3-methyl-N-(6-{2-[3-(5-nitropyridin-2-yloxy)phenyl]-chroman-6-yloxy}pyridin-3-yl)butyramide hydrochloride (S)-2-Amino-3-methyl-N-(6-{2-[3-(5-nitropyridin-2-yloxy)phenylchroman-6-yloxy}pyridin-3-yl)butyramide hydrochloride was obtained in the same manner as described for (S)-2-Amino-3-methyl-N-[6-(2-phenylchroman-6-yloxy)-pyridin-3-yl]butyramide in Example 21 b). $^1$H NMR (400 MHz, d$_6$-DMSO) δ: 10.91 (br s, 1H), 9.05 (d, 1H, J 2.7 Hz), 8.64 (dd, 1H, 3.0, 9.1 Hz), 8.38 (d, 1H, J 2.5 Hz), 8.32 (br s, 2H), 8.06 (dd, 1H, J 2.5, 8.8 Hz), 7.52 (t, 1H, J 7.9 Hz), 7.40 (d, 1H, J 7.6 Hz), 7.27-7.32 (m, 2H), 7.22 (d, 1H, J 8.1 Hz), 7.00 (d, 1H, J 8.8 Hz), 6.86-6.89 (m, 4H), 5.17 (d, 1H, J 8.8 Hz), 3.81 (m, 1H), 2.96 (m, 1H), 2.73 (m, 1H), 2.20 (m, 1H), 2.00 (m, 1H), 0.99-1.01 (m, 6H).

Example 23

Pyrrolidine-2-carboxylic acid [6-(2-phenylchroman-6-yloxy)pyridin-3-yl]amide and its derivatives Pyrrolidine-2-carboxylic acid [6-(2-phenylchroman-6-yloxy)pyridin-3-yl]amide and its derivatives were prepared as described for piperidine-4-carboxylic acid [6-(2-phenylchroman-6-yloxy)pyridine-3-yl]amine in Example 19 a) and b) but replacing N-(tert-butoxycarbonyl)isonipecotic acid with (S),(R) or (R,S)-pyrrolidine-1,2-dicarboxylic acid 1-tert-butyl ester and 5-amino-2-(2-phenylchroman-6-yloxy)-pyridine by an appropriate 5-aminopyridine derivatives.

a) 2-[6-(2-Phenylchroman-6-yloxy)pyridin-3-ylcarbamoyl]pyrrolidine-1-carboxylic acid tert-butyl ester and its derivatives 2-[6-(2-Phenylchroman-6-yloxy)pyridin-3-ylcarbamoyl]-(S)-pyrrolidine-1-carboxylic acid tert-butyl ester $^1$H NMR (300 MHz, d$_6$-DMSO) δ: 10.1 (s, 1H), 8.31 (d, 1H, J 2.4 Hz), 8.03 (dd, 1H, J 2.4, 8.8 Hz), 7.47-7.33 (m, 5H), 6.95 (d, 1H, J 8.8 Hz), 6.87-6.85 (m, 3H), 5.12 (dd, 1H, J 2.1, 9.9 Hz), 4.25 (m, 1H), 3.5-3.3 (m, 2H), 2.97 (m, 1H), 2.74 (m, 1H), 2.29-2.11 (m, 2H), 2.09-1.73 (m, 4H), 1.40 (s, 3H) 1.29 (m, 6H).

2-[6-(2-Phenylchroman-6-yloxy)pyridin-3-ylcarbamoyl]-(R)-pyrrolidine-1-carboxylic acid tert-butyl ester $^1$H NMR (400 MHz, d$_6$-DMSO) δ: 10.09 (s, 1H), 8.31 (s, 1H), 8.03 (d, 1H, J 8.8 Hz), 7.46-7.33 (m, 5H), 6.95 (d, 1H, J 8.8 Hz), 6.88-6.85 (m, 3H), 5.12 (d, 1H, J 10.0 Hz), 4.18 (m, 1H), 3.42-3.31 (m, 2H), 2.97 (m, 1H), 2.75 (m, 1H), 2.22-2.17 (m, 2H), 2.01-1.80 (m, 4H), 1.40 (s, 3H) 1.29 (m, 6H).

2-[6-(2-(4-Fluorophenyl)chroman-6-yloxy)pyridin-3-ylcarbamoyl]-(S)-pyrrolidine-1-carboxylic acid tert-butyl ester $^1$H NMR (400 MHz, d$_6$-DMSO) δ: 10.09 (s, 1H), 8.31 (d, 1H, 2.5 Hz), 8.03 (dd, 1H, J 8.8, 2.5 Hz), 7.50 (m, 2H), 7.23 (m, 2H), 6.95 (d, 1H, J 8.8 Hz), 6.88-6.85 (m, 3H), 5.12 (d, 1H, J 8.6 Hz), 4.26 (m, 1H), 3.41-3.34 (m, 2H), 2.96 (m, 1H), 2.73 (m, 1H), 2.22-2.13 (m, 2H), 1.90-1.80 (m, 4H), 1.40 (s, 3H) 1.29 (m, 6H).

2-[6-(2-(3-Fluorophenyl)chroman-6-yloxy)pyridin-3-ylcarbamoyl]-(S)-pyrrolidine-1-carboxylic acid tert-butyl ester $^1$H NMR (400 MHz, d$_6$-DMSO) δ: 10.09 (s, 1H), 8.31 (s, 1H), 8.03 (d, 1H, J 8.7 Hz), 7.46 (m, 1H), 7.31-7.27 (m, 2H), 7.17 (m, 1H), 6.95 (d, 1H, J 8.7 Hz), 6.87-6.85 (m, 3H), 5.16 (d, 1H, J 8.6 Hz), 4.17 (m, 1H), 3.41-3.34 (m, 2H), 2.95 (m, 1H), 2.72 (m, 1H), 2.22-2.18 (m, 2H), 1.95-1.79 (m, 4H), 1.40 (s, 3H) 1.29 (m, 6H).

2-[6-(2-(2-Fluorophenyl)chroman-6-yloxy)pyridin-3-ylcarbamoyl]-(S)-pyrrolidine-1-carboxylic acid tert-butyl ester $^1$H NMR (400 MHz, d$_6$-DMSO) δ: 10.09 (s, 1H), 8.31 (s, 1H), 8.03 (d, 1H, J 8.7 Hz), 7.55 (m, 1H), 7.41 (m, 1H), 7.29-7.23 (m, 2H), 6.96 (d, 1H, J 8.7 Hz), 6.90-6.85 (m, 3H), 5.34 (d, 1H, J 9.6 Hz), 4.17 (m, 1H), 3.44-3.35 (m, 2H), 3.00

(m, 1H), 2.75 (m, 1H), 2.17 (m, 1H) 2.05 (m, 1H), 1.90-1.77 (m, 4H), 1.40 (s, 3H) 1.29 (m, 6H).

b) Pyrrolidine-2-carboxylic acid [6-(2-phenylchroman-6-yloxy)pyridin-3-yl]amide and its derivatives (S)-Pyrrolidine-2-carboxylic acid [6-(2-phenylchroman-6-yloxy)pyridin-3-yl]amide hydrochloride $^1$H NMR (300 MHz, d$_6$-DMSO) δ: 10.9 (s, 1H), 8.38 (d, 1H, J 2.7 Hz), 8.03 (dd, 1H, J 2.7, 8.8 Hz), 7.47-7.33 (m, 5H), 7.00 (d, 1H, J 8.8 Hz), 6.99-6.85 (m, 3H), 5.12 (dd, 1H, 2.2, 10.1 Hz), 3.32-3.20 (m, 2H), 2.97 (m, 1H), 2.74 (m, 1H), 2.42 (m, 1H), 2.15 (m, 1H), 2.08-1.90 (m, 4H).

(R)-Pyrrolidine-2-carboxylic acid [6-(2-phenylchroman-6-yloxy)pyridin-3-yl]amide hydrochloride $^1$H NMR (400 MHz, d$_6$-DMSO) δ: 11.11 (s, 1H), 10.03 (bs, 1H), 8.71 (bs, 1H), 8.40 (s, 1H), 8.06 (d, 1H, J 8.8 Hz), 7.46-7.32 (m, 5H), 7.00 (d, 1H, J 8.8 Hz), 6.88-6.86 (m, 3H), 5.12 (d, 1H, 9.9 Hz), 4.39 (m, 1H), 3.27-3.20 (m, 2H), 2.98 (m, 1H), 2.73 (m, 1H), 2.44 (m, 1H), 2.17 (m, 1H), 2.04-1.93 (m, 4H).

(S)-Pyrrolidine-2-carboxylic acid [6-(2-(4-fluoropheny)1chroman-6-yloxy)pyridin-3-yl]amide hydrochloride $^1$H NMR (400 MHz, d$_6$-DMSO) δ: 10.92 (s, 1H), 9.72 (bs, 1H), 8.70 (bs, 1H), 8.38 (d, 1H, J 2.5 Hz), 8.03 (dd, 1H, J 8.9, 2.5 Hz), 7.50 (m, 2H), 7.23 (m, 2H), 7.00 (d, 1H, J 8.9 Hz), 6.89-6.86 (m, 3H), 5.12 (d, 1H, 10.1 Hz), 4.35 (m, 1H), 3.29-3.24 (m, 2H), 2.97 (m, 1H), 2.73 (m, 1H), 2.42 (m, 1H), 2.16 (m, 1H), 2.03-1.91 (m, 4H).

(S)-Pyrrolidine-2-carboxylic acid [6-(2-(3-fluoro)phenylchroman-6-yloxy)pyridin-3-yl]amide hydrochloride $^1$H NMR (400 MHz, d$_6$-DMSO) δ: 10.97 (s, 1H), 9.79 (bs, 1H), 8.70 (bs, 1H), 8.38 (d, 1H, J 2.6 Hz), 8.04 (dd, 1H, J 8.9, 2.6 Hz), 7.46 (m, 1H), 7.31-7.27 (m, 2H), 7.17 (m, 1H), 7.01 (d, 1H, J 8.9 Hz), 6.90-6.85 (m, 3H), 5.16 (d, 1H, 8.4 Hz), 4.37 (m, 1H), 3.29-3.24 (m, 2H), 2.96 (m, 1H), 2.72 (m, 1H), 2.42 (m, 1H), 2.20 (m, 1H), 2.03-1.91 (m, 4H).

(S)-Pyrrolidine-2-carboxylic acid [6-(2-(2-fluoropheny)1chroman-6-yloxy)pyridin-3-yl]amide hydrochloride $^1$H NMR (400 MHz, d$_6$-DMSO) δ: 10.90 (s, 1H), 9.70 (bs, 1H), 8.71 (bs, 1H), 8.38 (d, 1H, J 2.7 Hz), 8.03 (dd, 1H, J 8.9, 2.5 Hz), 7.55 (m, 1H), 7.42 (m, 1H), 7.29-7.23 (m, 2H), 7.01 (d, 1H, J 8.9 Hz), 6.90-6.86 (m, 3H), 5.34 (d, 1H, 8.6 Hz), 4.37 (m, 1H), 3.29-3.24 (m, 2H), 2.99 (m, 1H), 2.76 (m, 1H), 2.40 (m, 1H), 2.17 (m, 1H), 2.07-1.91 (m, 4H).

Example 24

(S)-Pyrrolidine-2-carboxylic acid (6-{2-[3-(5-nitropyridin-2-yloxy)phenyl]-chroman-6-yloxy}pyridin-3-yl)amide (S)-Pyrrolidine-2-carboxylic acid (6-{2-[3-(5-nitropyridin-2-yloxy)phenyl]-chroman-6-yloxy}pyridin-3-yl)amide was prepared as described for (S)-2-amino-3-methyl-N-(6-{2-[3-(5-nitropyridin-2-yloxy-phenyl-chroman-6-yloxy}pyridin-3-yl)-butyramide in Example 22 steps a)-c) starting with (S)-pyrrolidine-1,2-dicarboxylic acid 1-tert-butyl ester.

a) 2-{6-[2-(3-Hydroxyphenyl)chroman-6-yloxy] pyridin-3-ylcarbamoyl}-(S)-pyrrolidine-1-carboxylic acid tert-butyl ester $^1$H NMR (400 MHz, d$_6$-DMSO) δ: 10.09 (s, 1H), 9.43 (s, 1H), 8.31 (s, 1H), 8.03 (d, 1H, J 8.9 Hz), 7.18 (t, 1H, J 8.0 Hz), 6.95 (d, 1H, J 8.9 Hz), 6.87-6.84 (m, 5H), 6.71, (d, 1H, J 7.2 Hz), 5.03 (d, 1H, J 8.2 Hz), 4.19 (m, 1H), 3.42-3.35 (m, 2H), 2.93 (m, 1H), 2.69 (m, 1H), 2.21-2.12 (m, 2H), 1.95-1.79 (m, 4H), 1.40 (s, 3H) 1.28 (m, 6H).

b) 2-(6-{2-[3-(5-Nitropyridin-2-yloxy)phenyl]chroman-6-yloxy}pyridin-3-ylcarbamoyl)-(S)-pyrrolidine-1-carboxylic acid tert-butyl ester $^1$H NMR (400 MHz, d$_6$-DMSO) δ: 10.09 (s, 1H), 9.05 (d, 1H, J 2.9 Hz), 8.63 (dd, 1H, J 8.9, 2.9 Hz), 8.31 (s, 1H), 8.03 (d, 1H, J 8.8 Hz), 7.52 (t, 1H, J 7.8 Hz), 7.40 (d, 1H, J 7.8 Hz), 7.31-7.27 (m, 2H) 7.21 (dd, 1H, J 7.8, 1.7 Hz), 6.95 (d, 1H, J 8.9 Hz), 6.87-6.85 (m, 3H), 5.17 (d, 1H, J 9.3 Hz), 4.18 (m, 1H), 3.42-3.34 (m, 2H), 2.95 (m, 1H), 2.73 (m, 1H), 2.20 (m, 1H), 1.97 (m, 1H), 1.89-1.79 (m, 4H), 1.40 (s, 3H) 1.28 (m, 6H).

c) (S)-Pyrrolidine-2-carboxylic acid (6-{2-[3-(5-nitropyridin-2-yloxy)-phenyl]chroman-6-yloxy}pyridin-3-yl)amide hydrochloride $^1$H NMR (400 MHz, d$_6$-DMSO) δ: 10.89 (s, 1H), 9.69 (bs, 1H), 9.05 (d, 1H, J 2.8 Hz), 8.71 (bs, 1H), 8.64 (dd, 1H, J 9.0, 2.8 Hz), 8.37 (d, 1H, J 2.7 Hz), 8.04 (dd, 1H, J 8.8, 2.7 Hz), 7.52 (t, 1H, J 7.9 Hz), 7.40 (d, 1H, J 7.9 Hz), 7.31-7.27 (m, 2H), 7.21 (d, 1H, J 8.8 Hz), 7.00 (d, 1H, J 9.0 Hz), 6.88-6.83 (m, 3H), 5.17 (d, 1H, 8.4 Hz), 4.35 (m, 1H), 3.29-3.24 (m, 2H), 2.95 (m, 1H), 2.73 (m, 1H), 2.40 (m, 1H), 2.22 (m, 1H), 2.04-1.91 (m, 4H).

Example 25

(S)-2-Amino-3-hydroxy-N-[6-(2-phenylchroman-6-yloxy)pyridin-3-yl]propionamide hydrochloride (S)-2-Amino-3-hydroxy-N-[6-(2-phenylchroman-6-yloxy)pyridin-3-yl]-propionamide hydrochloride was prepared as described for piperidine-4-carboxylic acid [6-(2-phenylchroman-6-yloxy)pyridin-3-yl]amine in Example 19 a) and b) but replacing N-(tert-butoxycarbonyl)isonipecotic acid with (S)-2-tert-butoxycarbonyl-amino-3-hydroxypropionic acid.

a) {(S)-2-Hydroxy-1-[6-(2-phenylchroman-6-yloxy) pyridin-3-ylcarbamoyl]-ethyl}carbamic acid tert-butyl ester $^1$H NMR (400 MHz, d$_6$-DMSO) δ: 10.07 (br s, 1H), 8.33 (d, 1H, J 2.4 Hz), 8.05 (dd, 1H, J 2.4, 9.0 Hz), 7.39-7.47 (m, 5H), 7.32-7.36 (m, 1H), 6.94 (d, 1H, J 9.0 Hz), 6.85-6.86 (m, 2H), 6.77 (br d, 1H, J 7.3 Hz), 5.12 (d, 1H, J 10.0 Hz), 4.95 (br s, 1H), 4.14 (m, 1H), 3.63 (br s, 2H), 2.95 (m, 1H), 2.70 (m, 1H), 2.18 (m, 1H), 2.01 (m, 1H), 1.39 (s, 9H).

b) (S)-2-Amino-3-hydroxy-N-[6-(2-phenylchroman-6-yloxy)pyridin-3-yl]propionamide hydrochloride $^1$H NMR (400 MHz, CD$_3$OD) δ: 8.63 (d, 1H, J 2.4 Hz), 8.22 (dd, 1H, J 2.4, 9.1 Hz), 7.36-7.45 (m, 4H), 7.29-7.33 (m, 1H), 7.05 (d, 1H, J 9.1 Hz), 6.94-6.97 (m, 3H), 5.11 (d, 1H, J 10.0 Hz), 4.15 (m, 1H), 3.97-4.06 (m, 2H), 3.03 (m, 1H), 2.79 (m, 1H), 2.24 (m, 1H), 2.07 (m, 1H).

Example 26

(S)-2-Amino-4-[6-(2-phenylchroman-6-yloxy)pyridin-3-ylcarbamoyl]butyric acid (S)-2-Amino-4-[6-(2-phenylchroman-6-yloxy)pyridin-3-ylcarbamoyl]butyric acid was prepared as described for piperidine-4-carboxylic acid [6-(2-phenyl-chroman-6-yloxy)pyridine-3-yl]amine in Example 19 a) and b) but replacing N-(tert-butoxycarbonyl)isonipecotic acid with (S)-2-carboxyaminopentanedioic acid 1-tert-butyl ester.

a) (S)-2-tert-Butoxycarbonylamino-4-[6-(2-phenyl-chroman-6-yloxy)-pyridine-3-ylcarbamoyl]butyric acid tert-butyl ester $^1$H NMR (400 MHz, d$_6$-DMSO) δ: 10.01 (br s, 1H), 8.28 (d, 1H, J 2.4 Hz), 8.01 (dd, 1H, J 2.4, 8.8 Hz), 7.39-7.46 (m, 4H), 7.32-7.35 (m, 1H), 7.14 (br d, 1H, J 7.7 Hz), 6.93 (d, 1H, J 8.8 Hz), 6.84-6.86 (m, 3H), 5.12 (d, 1H, J 10.0 Hz), 3.84 (m, 1H), 2.97 (m, 1H), 2.71 (m, 1H), 2.38-2.42 (m, 2H), 2.16 (m, 1H), 1.96-2.04 (m, 2H), 1.81 (m, 1H), 1.40 (s, 9H), 1.38 (s, 9H).

b) (S)-2-Amino-4-[6-(2-phenylchroman-6-yloxy)pyridin-3-ylcarbamoyl]-butyric acid hydrochloride $^1$H NMR (400 MHz, d$_6$-DMSO) δ: 10.28 (br s, 1H), 8.41 (br s, 2H), 8.33 (d, 1H, J 2.4 Hz), 8.03 (dd, 1H, J 2.4, 8.8 Hz), 7.39-7.46 (m, 4H), 7.32-7.36 (m, 1H), 6.94 (d, 1H, J 8.8 Hz), 6.85-6.86 (m, 3H), 5.12 (d, 1H, J 10.1 Hz), 3.96 (m, 1H), 2.97 (m, 1H), 2.72 (m, 1H), 2.50-2.65 (m, 2H), 2.12-2.19 (m, 3H), 2.00 (m, 1H).

Example 27

(S)-4-Amino-4-[6-(2-phenylchroman-6-yloxy)pyridin-3-ylcarbamoyl]butyric acid (S)-4-Amino-4-[6-(2-phenylchroman-6-yloxy)pyridin-3-ylcarbamoyl]butyric acid was prepared as described for piperidine-4-carboxylic acid [6-(2-phenyl-chroman-6-yloxy)pyridine-3-yl]amine in Example 19 a) and b) but replacing N-(tert-butoxycarbonyl)isonipecotic acid with (S)-2-carboxyaminopentanedioic acid 5-tert-butyl ester.

a) (S)-4-tert-Butoxycarbonylamino-4-[6-(2-phenyl-chroman-6-yloxy)pyridin-3-ylcarbamoyl]butyric acid tert-butyl ester $^1$H NMR (400 MHz, d$_6$-DMSO) δ: 10.09 (br s, 1H), 8.32 (d, 1H, J 2.4 Hz), 8.04 (dd, 1H, J 2.4, 8.8 Hz), 7.39-7.47 (m, 4H), 7.32-7.35 (m, 1H), 7.06 (br d, 1H, J 7.7 Hz), 6.94 (d, 1H, J 8.8 Hz), 6.85-6.86 (m, 3H), 5.12 (d, 1H, J 10.0 Hz), 4.07 (m, 1H), 2.95 (m, 1H), 2.72 (m, 1H), 2.26-2.27 (m, 2H), 2.17 (m, 1H), 1.92-2.04 (m, 2H), 1.75 (m, 1H), 1.38 (br s, 18H).

b) (S)-4-Amino-4-[6-(2-phenylchroman-6-yloxy)pyridin-3-ylcarbamoyl]-butyric acid hydrochloride $^1$H NMR (400 MHz, MeOD) δ: 8.54 (d, 1H, J 2.8 Hz), 8.15 (dd, 1H, J 2.8, 9.0 Hz), 7.43-7.45 (m, 2H), 7.36-7.40 (m, 2H), 7.29-7.33 (m, 1H), 7.01 (d, 1H, J 9.0 Hz), 6.93-6.94 (m, 3H), 5.11 (d, 1H, J 10.0 Hz), 4.11 (m, 1H), 3.01 (m, 1H), 2.79 (m, 1H), 2.56 (m, 2H), 2.22-2.30 (m, 3H), 2.03-2.09 (m, 1H).

Example 28

(S)-3-Amino-N-[6-(2-phenylchroman-6-yloxy)pyridin-3-yl]succinamic acid

S)-3-Amino-N-[6-(2-phenylchroman-6-yloxy)pyridin-3-yl]succinamic acid was prepared as described for piperidine-4-carboxylic acid [6-(2-phenylchroman-6-yloxy)pyridine-3-yl]amine in Example 19 a) and b) but replacing N-(tert-butoxycarbonyl)isonipecotic acid with (S)-2-tert-butoxycarbonylamino-succinic acid 4-tert-butyl ester.

a) (S)-3-tert-Butoxycarbonylamino-N-[6-(2-phenyl-chroman-6-yloxy)pyridin-3-yl]succinamic acid tert-butyl ester $^1$H-NMR (400 MHz; d$_6$-DMSO) δ: 10.12 (s, 1H), 8.31 (d, 1H, J 2.4 Hz), 8.02 (dd, 1H, J 8.9, 2.4 Hz), 7.46-7.39 (m, 5H), 7.34 (d, 1H, J 7.1 Hz), 6.94 (d, 1H, J 8.9 Hz), 6.87-6.84 (m, 3H), 5.12 (d, 1H, J 10.0 Hz), 4.44 (m, 1H), 2.97 (m, 1H), 2.74-2.65 (m, 2H), 2.50 (m, 1H), 2.16 (m, 1H), 2.00 (m, 1H), 1.38 (s, 18H).

b) (S)-3-Amino-N-[6-(2-phenylchroman-6-yloxy)pyridin-3-yl]succinamic acid Hydrochloride $^1$H-NMR (400 MHz; d$_6$-DMSO) δ: 10.83 (s, 1H), 8.41 (bs, 3H), 8.36 (d, 1H, J 2.4 Hz), 8.03 (dd, 1H, J 8.9, 2.4 Hz), 7.47-7.32 (m, 5H), 7.00 (d, 1H, J 8.9 Hz), 6.88-6.85 (m, 3H), 5.12 (d, 1H, J 10.1 Hz), 4.25 (m, 1H), 3.03-2.87 (m, 3H), 2.73 (m, 1H), 2.17 (m, 1H), 2.00 (m, 1H).

Example 29

(S)-2-Amino-N-[6-(2-phenylchroman-6-yloxy)pyridin-3-yl]succinamic acid (S)-2-Amino-N-[6-(2-phenylchroman-6-yloxy)pyridin-3-yl]succinamic acid Hydrochloride was prepared as described for piperidine-4-carboxylic acid [6-(2-phenylchroman-6-yloxy)pyridine-3-yl]amine in Example 19 a) and b) but replacing N-(tert-butoxycarbonyl)isonipecotic acid with (S)-2-tert butoxycarbonylamino-succinic acid 1-tert-butyl ester.

a) (S)-2-tert-Butoxycarbonylamino-N-[6-(2-phenyl-chroman-6-yloxy)pyridin-3-yl]succinamic acid tert-butyl ester $^1$H-NMR (400 MHz; d$_6$-DMSO) δ: 10.10 (s, 1H), 8.29 (s, 1H), 8.15 (d, 1H, J 8.9 Hz), 7.47-7.39 (m, 5H), 7.34 (d, 1H, J 8.4 Hz), 6.94 (d, 1H, J 8.9 Hz), 6.86-6.84 (m, 3H), 5.12 (d, 1H, J 10.0 Hz), 4.29 (m, 1H), 2.97 (m, 1H), 2.82-2.76 (m, 2H), 2.61 (m, 1H), 2.17 (m, 1H), 2.01 (m, 1H), 1.38 (s, 12H), 1.36 (s, 6H).

b) (S)-2-Amino-N-[6-(2-phenylchroman-6-yloxy)pyridin-3-yl]succinamic acid Hydrochloride $^1$H-NMR (400 MHz; d$_6$-DMSO) δ: 13.7 (bs, 1H), 10.52 (s, 1H), 8.36-8.32 (m, 4H), 8.01 (d, 1H, J 8.7 Hz), 7.46-7.32 (m, 5H), 6.96 (d, 1H, J 8.7 Hz), 6.87-6.85 (m, 3H), 5.12 (d, 1H, J 10.0 Hz), 4.27 (m, 1H), 3.07-2.93 (m, 3H), 2.72 (m, 1H), 2.18 (m, 1H), 2.00 (m, 1H).

Example 30

N-{6-[2-(4-fluorophenyl)chroman-6-yloxy]pyridin-3-yl}-4-(4-methylpiperazin-1-ylmethyl)benzamide a) 4-Chloromethylbenzoic acid methyl ester

4-Chloromethylbenzoic acid (2.0 g) was dissolved in 300 ml of methanol and 0.5 ml concentrated sulphuric acid was added. The mixture was stirred at room temperature for eight days. Methanol was evaporated and the residue was dissolved in ethyl acetate. The organic layer was washed with saturated $NaHCO_3$-solution, dried with $Na_2SO_4$ and evaporated to yield 4-chloromethylbenzoic acid methyl ester.
$^1$H NMR (300 MHz, $d_6$-DMSO) δ: 3.86 (s, 3H), 4.84 (s, 2H), 7.59 (d, 2H, J 8.2 Hz), 7.97 (d, 2H, J 8.2 Hz).

b) 4-(4-Methylpiperazin-1-ylmethyl)benzoic acid methyl ester

4-Chloromethylbenzoic acid methyl ester (1.66 g), 1-methylpiperazine (1.8 g) and sodium iodide (0.67 g) were added into acetone (50 ml). The reaction mixture was stirred at 60° C. for 9 hours. More 1-methylpiperazine (0.9 g) and sodium iodide (0.34 g) were added and after stirring additional 1½ hours at 60° C. the reaction mixture was allowed to cool into room temperature. The mixture was filtered and acetone was evaporated. The residue was dissolved in ethyl acetate and washed with water. The solvent was dried with $NaSO_4$ and evaporated to yield 4-(4-methyl-piperazin-1-ylmethyl)benzoic acid methyl ester. $^1$H NMR (300 MHz, $d_6$-DMSO) δ: 2.18 (s, 3H), 2.37 (bs, 8H), 3.53 (s, 2H), 3.84 (s, 3H), 7.44 (d, 2H, J 8.1 Hz), 7.91 (d, 2H, J 8.2 Hz).

HCl-salt of 4-(4-Methylpiperazin-1-ylmethyl)benzoic acid methyl ester 4-(4-Methylpiperazin-1-ylmethyl)benzoic acid methyl ester was dissolved in ethyl acetate and 1 M HCl-diethyl ether solution was added. The mixture was stirred for 1 hour and precipitated HCl-salt was filtered and washed with diethyl ether. $^1$H NMR (300 MHz, $d_6$-DMSO) δ: 2.78 (s, 3H), 3.10-3.75 (m, 8H), 3.87 (s, 3H), 4.35 (bs, 2H), 7.77 (d, 2H, J 7.5 Hz), 8.00 (d, 2H, J 8.1 Hz).

c) 4-(4-Methylpiperazin-1-ylmethyl)benzoic acid

HCl-salt of 4-(4-methylpiperazin-1-ylmethyl)benzoic acid methyl ester (1.25 g) was dissolved in potassium hydroxide-methanol solution (0.93 g KOH in 15 ml methanol). Water (0.75 ml) was added and the mixture was refluxed for 1 hour. The reaction mixture was allowed to cool into room temperature and the pH was tuned to 6 with 2 M HCl. The solvent was evaporated and the residue was dried under vacuum. The residue contained 4-(4-methylpiperazin-1-ylmethyl)benzoic acid and inorganic salts. It was used further without purification and the yield of title compound was assumed to be 100%. $^1$H NMR (400 MHz, $d_6$-DMSO) δ: 2.27 (s, 3H), 2.44 (bs, 2H), 3.18-3.95 (m, 8H), 7.41 (d, 2H, J 8.0 Hz), 7.89 (d, 2H, J 8.1 Hz).

d) N-{6-[2-(4-fluorophenyl)chroman-6-yloxy]pyridin-3-yl}-4-(4-methyl-piperazin-1-ylmethyl)benzamide 4-(4-Methylpiperazin-1-ylmethyl)benzoic acid (ca 0.19 g), 6-[2-(4-fluoro-phenyl)-chroman-6-yloxy]pyridin-3-ylamine (0.18 g) and 1-(3-dimethylamino-propyl)-3-ethylcarbodiimide hydrochloride (0.12 g) were added into dichloromethane (12 ml). The mixture was stirred at room temperature and after 4 hours more 4-(4-methylpiperazin-1-ylmethyl)-benzoic acid (ca 0.11 g) and 1-(3-dimethyl-aminopropyl)-3-ethylcarbodiimide hydrochloride (0.0.46 g) were added. Stirring was continued for additional 3 hours. Water and dichloromethane were added and organic and water phases were separated. Water phase was extracted with dichloromethane. The product was purified by column chromatography using dichloromethane-methanol (9:1) as an eluent to give N-{6-[2-(4-fluorophenyl)chroman-6-yloxy]-pyridin-3-yl}-4-(4-methylpiperazin-1-ylmethyl)benzamide. $^1$H NMR (300 MHz, $d_6$-DMSO) δ: 1.90-2.08 (m, 1H), 2.11-2.21 (m, 1H), 2.18 (s, 3H), 2.38 (bs, 8H), 2.68-2.79 (m, 1H), 2.91-3.05 (m, 1H), 3.54 (s, 2H), 5.13 (dd, 1H, J 2.0, 10.1 Hz), 6.86 (d, 2H, J 1.2 Hz), 6.90 (s, 1H), 6.98 (d, 1H, J 8.8 Hz), 7.19-7.27 (m, 2H), 7.43-7.54 (m, 4H), 7.92 (d, 2H, J 8.2 Hz), 8.18 (dd, 1H, J 2.7, 8.9 Hz), 8.48 (d, 1H, J 2.7 Hz), 10.31 (s, 1H).

Example 31

N-[6-(2-Phenylchroman-6-yloxy)pyridin-3-yl]succinamic acid 6-(2-Phenylchroman-6-yloxy)pyridin-3-ylamine (example 35) (270 mg) and succinic acid (151 mg) were dissolved in dichloromethane (16 ml). 1-(3-Dimethyl-aminopropyl)-3-ethylcarbodiimide hydrochloride (245 mg) was added into a reaction mixture and it was stirred at room temperature for 3 hours. Water was added and the mixture was filtered. The precipitate was collected and treated with methanol and filtered again. The methanol-filtrate was evaborated to dryness to yield N-[6-(2-phenylchroman-6-yloxy)pyridin-3-yl]succinamic acid. $^1$H NMR (400 MHz, $d_6$-DMSO) δ: 12.0 (bs, 1H), 10.08 (s, 1H), 8.29 (d, 1H, J 2.4 Hz), 8.01 (dd, 1H, J 8.8, 2.4 Hz), 7.46-7.32 (m, 5H), 6.93 (d, 1H, J 8.8 Hz), 6.86-6.84 (m, 3H), 5.11 (d, 1H, J 8.6 Hz), 2.96 (m, 1H), 2.70 (m, 1H), 2.56-2.52 (m, 4H), 2.16 (m, 1H), 2.00 (m, 1H).

Example 32

2-Chloro-N-[6-(2-phenylchroman-6-yloxy)pyridin-3-yl]acetamide

To a cooled solution of 5-amino-2-(2-phenylchroman-6-yloxy)-pyridine (500 mg) in 7.5 ml of methylene chloride was added triethyl amine (437 μl) and chloracetyl chloride (163 μl). The reaction mixture was stirred at room temperature for 3 hours and quenched with addition of water. Water layer was acidified and extracted with methylene chloride. The combined organic layers were dried with $Na_2SO_4$ and evaporated. The 2-chloro-N-[6-(2-phenyl-chroman-6-yloxy)-pyridin-3-yl]-acetamide was purified by column chromatography using 10% methanol in methylene chloride as an eluant. $^1$H-NMR (400 MHz; $d_6$-DMSO) δ: 10.4 (s, 1H), 8.30 (d, 1H, J 2.7 Hz), 8.03 (dd, 1H, J 2.7, 8.8 Hz), 7.47-7.32 (m, 5H), 6.97 (d, 1H, J 8.8 Hz), 6.88-6.85 (m, 3H), 5.12 (dd, 1H, J 2.10, 10.1 Hz), 4.27 (s, 2H), 2.97-2.92 (m, 1H), 2.76-2.70 (m, 1H), 2.19-2.14 (m, 1H), 2.02-1.97 (m, 1H).

2-Chloro-N-{6-[2-(4-fluorophenyl)chroman-6-yloxy]pyridin-3-yl}acetamide was obtained using the same procedure as described above for 2-chloro-N-[6-(2-phenylchroman-6-yloxy)pyridin-3-yl]acetamide but replacing 5-amino-2-(2-phenylchroman-6-yloxy)pyridine by 5-amino-2-(2-(4-fluorophenylchroman-6-yloxy)pyridine. $^1$H-NMR (400 MHz; $d_6$-DMSO) δ: 10.4 (s, 1H), 8.29 (d, 1H, J 2.7 Hz), 8.02 (dd, 1H, J 2.7, 8.8 Hz), 7.52-7.48 (m, 2H), 7.25-7.20 (m, 2H), 6.97 (d, 1H, J 8.8 Hz), 6.88-6.84 (m, 3H), 5.12 (dd, 1H, J 1.90, 10.2

Hz), 4.27 (s, 2H), 2.98-2.92 (m, 1H), 2.76-2.69 (m, 1H), 2.18-2.13 (m, 1H), 2.01-1.96 (m, 1H),

Similarly using the same procedure as described above for 2-chloro-N-[6-(2-phenylchroman-6-yloxy)pyridin-3-yl]acetamide but replacing 5-amino-2-(2-phenylchroman-6-yloxy)pyridine by an appropriate pyridin-3-ylamine-derivative listed in Example 18, there can be obtained:

2-chloro-N-{6-[2-(3-fluorophenyl)chroman-6-yloxy]-pyridin-3-yl}acetamide,
2-chloro-N-{6-[2-(2-fluorophenyl)chroman-6-yloxy]-pyridin-3-yl}acetamide,
2-chloro-N-{6-[2-(2,3-difluorophenyl)chroman-6-yloxy]-pyridin-3-yl}acetamide,
2-chloro-N-{6-[2-(2,4-difluorophenyl)chroman-6-yloxy]-pyridin-3-yl}acetamide,
2-chloro-N-{6-[2-(2,5-difluorophenyl)chroman-6-yloxy]-pyridin-3-yl}acetamide,
2-chloro-N-{6-[2-(2,6-difluorophenyl)chroman-6-yloxy]-pyridin-3-yl}acetamide,
2-chloro-N-{6-[2-(3,4-difluorophenyl)chroman-6-yloxy]-pyridin-3-yl}acetamide,
2-chloro-N-{6-[2-(3,5-difluorophenyl)chroman-6-yloxy]-pyridin-3-yl}acetamide,
2-chloro-N-{6-[2-(2-trifluoromethylphenyl)chroman-6-yloxy]-pyridin-3-yl}acetamide,
2-chloro-N-{6-[2-(4-trifluoromethylphenyl)chroman-6-yloxy]-pyridin-3-yl}acetamide,
2-chloro-N-{6-[2-(3-chloro-4-fluorophenyl)chroman-6-yloxy]-pyridin-3-yl}acetamide,
2-chloro-N-{6-[2-(2-chlorophenyl)chroman-6-yloxy]-pyridin-3-yl}acetamide,
2-chloro-N-{6-[2-(3-chlorophenyl)chroman-6-yloxy]-pyridin-3-yl}acetamide,
2-chloro-N-{6-[2-(2,4-dichlorophenyl)chroman-6-yloxy]-pyridin-3-yl}acetamide,
2-chloro-N-{6-[2-(3-bromophenyl)chroman-6-yloxy]-pyridin-3-yl}acetamide,
2-chloro-N-{6-[2-(4-ethylphenyl)chroman-6-yloxy]-pyridin-3-yl}acetamide,
2-chloro-N-{6-[2-(3-methoxyphenyl)chroman-6-yloxy]-pyridin-3-yl}acetamide,
2-chloro-N-[6-(3-methyl-2-phenylchroman-6-yloxy)-pyridin-3-yl]acetamide,
2-chloro-N-[6-(2-phenylchroman-7-yloxy)-pyridin-3-yl]acetamide,
2-chloro-N-[6-(4-oxo-2-phenylchroman-6-yloxy)pyridin-3-yl]acetamide,
2-chloro-N-[6-(4-oxo-2-phenylchroman-7-yloxy)pyridin-3-yl]acetamide,
2-chloro-N-[6-(3-methyl-4-oxo-2-phenylchroman-6-yloxy)pyridin-3-yl]acetamide,
2-chloro-N-[6-(2-phenyl-2,3-dihydrobenzo[1,4]dioxin-6-yloxy)pyridin-3-yl]acetamide,
2-chloro-N-[6-(6-phenyl-5,6,7,8-tetrahydronaphthalen-2-yloxy)pyridin-3-yl]acetamide,
2-chloro-N-[6-(5-oxo-6-phenyl-5,6,7,8-tetrahydronaphthalen-2-yloxy)pyridin-3-yl]acetamide
2-chloro-N-[6-(2-phenyl-2,3-dihydrobenzo[1,4]oxathiin-6-yloxy)pyridin-3-yl]acetamide,
2-chloro-N-{6-[3-(3-fluorophenyl)chroman-7-yloxy]pyridin-3-yl}acetamide,
2-chloro-N-[6-(3-phenylchroman-7-yloxy)pyridin-3-yl]acetamide,
2-chloro-N-[6-(4-oxo-2-phenylchromen-6-yloxy)pyridin-3-yl]acetamide,
2-chloro-N-[6-(2-phenylindan-5-yloxy)pyridin-3-yl]acetamide, respectively.

Example 33

2-Amino-N-[6-(2-phenylchroman-6-yloxy)pyridin-3-yl]acetamide a) 2-Azido-N-[6-(2-phenylchroman-6-yloxy)pyridin-3-yl]acetamide 2-Chloro-N-[6-(2-phenylchroman-6-yloxy)pyridin-3-yl]acetamide (500 mg), sodium azide (445 mg) and acetonitrile were mixed. Reaction mixture was refluxed for 3 hours. After cooling into room temperature, the reaction mixture was filtered and the filtrate was evaporated to the dryness. $^1$H-NMR (400 MHz; $d_6$-DMSO) δ: 10.3 (s, 1H), 8.29 (d, 1H, J 2.7 Hz), 8.03 (dd, 1H, J 2.7, 8.8 Hz), 7.47-7.33 (m, 5H), 6.96 (d, 1H, J 8.8 Hz), 6.88-6.85 (m, 3H), 5.12 (dd, 1H, J 2.20, 10.1 Hz), 4.07 (s, 2H), 3.00-2.92 (m, 1H), 2.76-2.70 (m, 1H), 2.19-2.14 (m, 1H), 2.02-1.97 (m, 1H).

Similarly there was obtained:
2-azido-N-{6-[2-(4-fluorophenyl)chroman-6-yloxy]-pyridin-3-yl}-acetamide $^1$H-NMR (400 MHz; $d_6$-DMSO) δ: 10.3 (s, 1H), 8.30 (d, 1H, J 2.7 Hz), 8.03 (dd, 1H, J 2.7, 8.8 Hz), 7.53-7.47 (m, 2H), 7.26-7.19 (m, 2H), 6.96 (d, 1H, J 8.8 Hz), 6.88-6.84 (m, 3H), 5.12 (dd, 1H, J 2.1, 10.1 Hz), 4.07 (s, 2H), 3.00-2.92 (m, 1H), 2.76-2.70 (m, 1H), 2.19-2.14 (m, 1H), 2.02-1.97 (m, 1H).

b) 2-Amino-N-[6-(2-phenylchroman-6-yloxy)pyridin-3-yl]acetamide

2-Azido-N-[6-(2-phenylchroman-6-yloxy)pyridin-3-yl]acetamide (500 mg) was dissolved in methanol (100 ml) and 10% palladium on charcoal (125 mg) was added. Starting material was hydrogenated for 5 hours at room temperature to give 2-amino-N-[6-(2-phenylchroman-6-yloxy)pyridin-3-yl]acetamide. The product was isolated as its hydrochloride salt. $^1$H-NMR (400 MHz; $d_6$-DMSO) δ: 10.7 (s, 1H), 8.35 (d, 1H, J 2.6 Hz), 8.17 (bs, 3H), 8.01 (dd, 1H, J 2.6, 8.9 Hz), 7.47-7.32 (m, 51), 7.00 (d, 1H, J 8.9 Hz), 6.89-6.86 (m, 3H), 5.12 (dd, 1H, J 1.90, 10.1 Hz), 3.79 (q, 2H, J 5.6 Hz), 3.01-2.92 (m, 1H), 2.74-2.70 (m, 1H), 2.20-2.15 (m, 1H), 2.05-1.94 (m, 1H).

Similarly there was obtained:

2-Amino-N-{6-[2-(4-fluorophenyl)chroman-6-yloxy]-pyridin-3-yl}-acetamide $^1$H-NMR (400 MHz; $d_6$-DMSO) δ: 10.8 (s, 1H), 8.36 (d, 1H, J 2.7 Hz), 8.21 (bs, 3H), 8.02 (dd, 1H, J 2.7, 8.9 Hz), 7.52-7.47 (m, 2H), 7.26-7.19 (m, 2H), 6.99 (d, 1H, J 8.9 Hz), 6.88-6.85 (m, 3H), 5.14 (dd, 1H, J 1.90, 10.0 Hz), 3.79 (q, 2H, J 5.7 Hz), 2.97-2.91 (m, 1H), 2.74-2.69 (m, 1H), 2.19-2.12 (m, 1H), 2.01-1.91 (m, 1H).

Example 34

N-[6-(2-Phenylchroman-6-yloxy)pyridin-3-yl]-2-(4-phenylpiperazin-1-yl)acetamide

To a solution of 2-Chloro-N-[6-(2-phenylchroman-6-yloxy)-pyridin-3-yl]-acetamide (500 mg) in acetonitrile was added potassium carbonate (333 mg) and 1-phenylpiperazine (213 μl). The mixture was stirred at room temperature. Water was added to the reaction mixture. Solution was extracted with dichloromethane. Organic extract was dried and evaporated. Product was purified by column chromatography using 10% methanol in dichlomethane as an eluant. N-[6-(2-Phenylchroman-6-yloxy)-pyridin-3-yl]-2-(4-phenylpiperazin-1-yl)acetamide was isolated as its dihydrochloride salt $^1$H NMR (300 MHz, $d_4$-MeOH) δ: 8.70 (bs, 1H), 8.25 (dd, 1H, J 2.1, 9.1 Hz), 7.46-7.28 (m, 7H), 7.09-6.96 (m, 7H), 5.12 (dd, 1H, J 2.3, 9.8 Hz), 4.32 (s, 2H), 3.73-3.40 (m, 8H), 3.10-2.95 (m, 1H), 2.90-2.76 (m, 1H), 2.33-2.20 (m, 1H), 2.13-2.00 (m, 1H).

Example 35

2-(4-Methylpiperazin-1-yl)-N-[6-(2-phenylchroman-6-yloxy)pyridin-3-yl]-acetamide To a solution of 2-chloro-N-[6-(2-phenylchroman-6-yloxy)pyridin-3-yl]-acetamide (200 mg) in acetonitrile was added potassium carbonate (133 mg) and 1-methylpiperazine (62 µl). The mixture was stirred at room temperature. Water was added to the reaction mixture. Solution was extracted with dichloromethane. Organic extract was dried and evaporated. N-[6-(2-Phenylchroman-6-yloxy)pyridin-3-yl]-2-(4-methylpiperazin-1-yl)acetamide was isolated as its dihydrochloride salt. $^1$H-NMR (300 MHz; $d_6$-DMSO) δ: 10.7 (s, 1H), 8.38 (d, 1H, J 2.7 Hz), 8.04 (dd, 1H, J 2.7, 8.8 Hz), 7.47-7.31 (m, 5H), 6.99 (d, 1H, J 8.8 Hz), 6.88-6.85 (m, 3H), 5.12 (dd, 1H, J 2.0, 10.0 Hz), 3.95 (s, 2H), 3.68-3.42 (m, 4H), 3.42-3.18 (m, 4H), 2.97-2.91 (m, 1H), 2.81 (s, 3H), 2.80-2.73 (m, 1H), 2.25-2.10 (m, 1H), 2.10-1.96 (m, 1H).

Example 36

N-[6-(2-Phenylchroman-6-yloxy)pyridin-3-yl]-2-piperazin-1-yl acetamide

To a solution of 2-Chloro-N-[6-(2-phenylchroman-6-yloxy)pyridin-3-yl]acetamide (200 mg) in acetonitrile was added potassium carbonate (133 mg) and 1-methylpiperazine (262 µl). The mixture was stirred at room temperature. Water was added to the reaction mixture. Solution was extracted with dichloromethane. Organic extract was dried and evaporated. N-[6-(2-Phenylchroman-6-yloxy)pyridin-3-yl]-2-(4-piperazin-1-yl)acetamide was isolated as its dihydrochloride salt. $^1$H-NMR (400 MHz; $d_6$-DMSO) δ: 10.7 (s, 1H), 8.38 (d, 1H, J 2.7 Hz), 8.03 (dd, 1H, J 2.7, 8.9 Hz), 7.47-7.33 (m, 5H), 6.99 (d, 1H, J 8.9 Hz), 6.88-6.85 (m, 3H), 5.12 (dd, 1H, J 2.1, 10.1 Hz), 3.5-3.2 (m, 10H), 2.97-2.92 (m, 1H), 2.74-2.70 (m, 1H), 2.20-2.15 (m, 1H), 2.03-1.97 (m, 1H).

Example 37

2-Morpholin-4-yl-N-[6-(2-phenylchroman-6-yloxy)pyridin-3-yl]acetamide

To a solution of 2-chloro-N-[6-(2-phenylchroman-6-yloxy)-pyridin-3-yl]-acetamide (200 mg) in acetonitrile was added potassium carbonate (133 mg) and morpholine (53 mg). The mixture was stirred at room temperature. Water was added to the reaction mixture. Solution was extracted with ethyl acetate. Organic extract was dried and evaporated. 2-Morpholin-4-yl-N-[6-(2-phenylchroman-6-yloxy)-pyridin-3-yl]-acetamide was isolated as its hydrochloride salt. $^1$H-NMR (400 MHz; $d_6$-DMSO) δ: 11.1 (s, 1H), 8.38 (d, 1H, J 2.7 Hz), 8.03 (dd, 1H, J 2.7, 8.9 Hz), 7.47-7.32 (m, 5H), 7.01 (d, 1H, J 8.9 Hz), 6.89-6.85 (m, 3H), 5.12 (dd, 1H, J 1.9, 10.0 Hz), 4.23 (s, 2H), 4.02-3.76 (m, 4H), 3.55-3.20 (m, 4H), 3.00-2.92 (m, 1H), 2.75-2.69 (m, 1H), 2.19-2.15 (m, 1H), 2.03-1.98 (m, 1H).

Example 38

N-[6-(2-Phenylchroman-6-yloxy)pyridin-3-yl]-2-thiomorpholin-4-yl acetamide

To a solution of 2-Chloro-N-[6-(2-phenylchroman-6-yloxy)-pyridin-3-yl]-acetamide (200 mg) in acetonitrile was added potassium carbonate (133 mg) and thiomarpholine (63 mg). The mixture was stirred at room temperature. Water was added to the reaction mixture. Solution was extracted with ethyl acetate. Organic extract was dried and evaporated. N-[6-(2-Phenylchroman-6-yloxy)-pyridin-3-yl]-2-thiomorpholin-4-yl-acetamide was isolated as its hydrochloride salt. $^1$H-NMR (400 MHz; $d_6$-DMSO) δ: 11.0 (s, 1H), 8.37 (d, 1H, J 2.6 Hz), 8.02 (dd, 1H, J 2.6, 8.9 Hz), 7.46-7.32 (m, 5H), 7.01 (d, 1H, J 8.9 Hz), 6.89-6.86 (m, 3H), 5.12 (dd, 1H, J 1.9, 10.1 Hz), 4.20 (bs, 2H), 3.85-2.65 (m, 10H), 2.20-2.15 (m, 1H), 2.05-1.95 (m, 1H).

Example 39

N-[6-(2-Phenylchroman-6-yloxy)pyridin-3-yl]-2-pyrrolidin-1-yl acetamide

To a solution of 2-Chloro-N-[6-(2-phenylchroman-6-yloxy)-pyridin-3-yl]-acetamide (200 mg) in acetonitrile was added potassium carbonate (133 mg) and pyrrolidine (51 µl). The mixture was stirred at room temperature. Water was added to the reaction mixture. Solution was extracted with ethyl acetate. Organic extract was dried and evaporated. N-[6-(2-Phenyl-chroman-6-yloxy) pyridin-3-yl]-2-pyrrolidin-1-yl acetamide was isolated as its hydrochloride salt. $^1$H-NMR (400 MHz; $d_6$-DMSO) δ: 10.8 (s, 1H), 8.35 (d, 1H, J 2.7 Hz), 8.02 (dd, 1H, J 2.7, 8.9 Hz), 7.47-7.32 (m, 5H), 7.00 (d, 1H, J 8.9 Hz), 6.89-6.85 (m, 3H), 5.12 (dd, 1H, J 1.9, 10.0 Hz), 4.25 (d, 2H, 5.4 Hz), 3.67-3.55 (m, 2H), 3.20-3.06 (m, 2H), 3.06-2.90 (m, 1H), 2.80-2.65 (m, 1H), 2.23-2.12 (m, 1H), 2.10-1.85 (m, 5H).

Example 40

2-(2,5-Dimethylpyrrolidin-1-yl)-N-[6-(2-phenylchroman-6-yloxy)pyridin-3-yl]acetamide To a solution of 2-Chloro-N-[6-(2-phenylchroman-6-yloxy)-pyridin-3-yl]-acetamide (200 mg) in acetonitrile was added potassium carbonate (133 mg) and 2,5-dimethylpyrrolidine (81 µl). The mixture was stirred at room temperature. Water was added to the reaction mixture. Solution was extracted with ethyl acetate. Organic extract was dried and evaporated. The product was purified by column chromatography using gradient elution with methanol-dichloromethane (2%->5%). $^1$H-NMR (300 MHz; $d_6$-DMSO) δ: 9.66 (s, 1H), 8.35 (d, 1H, J 2.7 Hz), 8.06 (dd, 1H, J 2.7, 8.8 Hz), 7.47-7.32 (m, 5H), 6.93 (d, 1H, J 8.8 Hz), 6.88-6.84 (m, 3H), 5.12 (dd, 1H, J 2.1, 9.9 Hz), 3.22 (s, 2H), 3.05-2.88 (m, 1H), 2.78-2.66 (m, 3H), 2.22-2.12 (m, 1H), 2.08-1.92 (m, 1H), 1.90-1.79 (m, 2H), 1.43-1.34 (m, 2H), 1.06 (d, 6H, J 6.1 Hz).

Example 41

N-[6-(2-Phenylchroman-6-yloxy)pyridin-3-yl]-2-piperidin-1-yl acetamide

To a solution of 2-Chloro-N-[6-(2-phenylchroman-6-yloxy)-pyridin-3-yl]-acetamide (200 mg) in acetonitrile was added potassium carbonate (133 mg) piperidine (60 µl). The mixture was stirred at room temperature. Water was added to the reaction mixture. Solution was extracted with dichloromethane. Organic extract was dried and evaporated. N-[6-

(2-Phenylchroman-6-yloxy)-pyridin-3-yl]-2-(4-piperin-1-yl)acetamide was isolated as its hydrochloride salt. $^1$H-NMR (400 MHz; d$_6$-DMSO) δ: 11.0 (s, 1H), 8.38 (d, 1H, J 2.7 Hz), 8.03 (dd, 1H, J 2.7, 8.8 Hz), 7.46-7.32 (m, 5H), 7.00 (d, 1H, J 8.8 Hz), 6.89-6.85 (m, 3H), 5.12 (dd, 1H, J 1.9, 10.0 Hz), 4.13 (d, 2H, J 4.9 Hz), 3.52-3.41 (m, 2H), 3.15-2.90 (m, 3H), 2.79-2.67 (m, 1H), 2.24-2.12 (m, 1H), 2.07-1.92 (m, 1H), 1.85-1.33 (m, 6H).

Example 42

2-(4-Hydroxypiperidin-1-yl)-N-[6-(2-phenylchroman-6-yloxy)pyridin-3-yl]acetamide To a solution of 2-Chloro-N-[6-(2-phenylchroman-6-yloxy)-pyridin-3-yl]-acetamide (200 mg) in acetonitrile was added potassium carbonate (133 mg) and 4-hydroxypiperidine (62 mg). The mixture was stirred at room temperature. Water was added to the reaction mixture. Solution was extracted with ethyl acetate. Organic extract was dried and evaporated. Product was purified by column chromatography using 10% methanol in methylene chloride as eluant. 2-(4-Hydroxypiperidin-1-yl)-N-[6-(2-phenyl-chroman-6-yloxy)-pyridin-3-yl]-acetamide was isolated as its hydrochloride salt. $^1$H-NMR (400 MHz; d$_4$-MeOH) δ: 8.41 (s, 1H), 8.06 (dd, 1H, J 2.7, 9.0 Hz), 7.45-7.28 (m, 5H), 6.95-6.85 (m, 4H), 5.10 (dd, 1H, J 2.1, 10.0 Hz), 4.13 (s, 2H), 3.72-3.68 (m, 1H), 3.48-3.43 (m, 3H), 3.25-3.10 (m, 1H), 3.02-2.97 (m, 1H), 2.81-2.75 (m, 1H), 2.26-1.76 (m, 6H). (M)$^+$=459 (5.8%), 360 (7.4%), 114 (100%).

Example 43

2-(3-Hydroxypiperidin-1-yl)-N-[6-(2-phenylchroman-6-yloxy)-pyridin-3-yl]-acetamide hydrochloride 2-(3-Hydroxypiperidin-1-yl)-N-[6-(2-phenylchroman-6-yloxy)-pyridin-3-yl]-acetamide hydrochloride was synthesized using the same procedure as described for 2-(4-Hydroxypiperidin-1-yl)-N-[6-(2-phenyl-chroman-6-yloxy)-pyridin-3-yl]-acetamide in Example 41 but replacing 4-hydroxypiperidine with 3-hydroxypiperidine. $^1$H-NMR (400 MHz; MeOD) δ: 1.47 (m, 1H), 1.62 (m, 1H), 1.75 (m, 1H), 1.87 (m, 1H), 2.05 (m, 1H), 2.22 (m, 1H), 2.37-2.57 (m, 3H), 2.68-2.72 (m, 2H), 3.01 (m, 1H), 3.08-3.22 (m, 2H), 3.80-3.88 (m, 1H), 5.08 (dd, 1H, J 1.8, 10.0 Hz), 6.82-6.91 (m, 4H), 7.27-7.46 (m, 5H), 8.06 (m, 1H), 8.35 (d, 1H, J 2.1 Hz).

Example 44

2-(3-Hydroxypyrrolidin-1-yl)-N-[6-(2-phenylchroman-6-yloxy)-pyridin-3-yl]-acetamide hydrochloride 2-(3-Hydroxypyrrolidin-1-yl)-N-[6-(2-phenylchroman-6-yloxy)-pyridin-3-yl]-acetamide hydrochloride was synthesized using the same procedure as described for 2-(4-hydroxypiperidin-1-yl)-N-[6-(2-phenyl-chroman-6-yloxy)-pyridin-3-yl]-acetamide in Example 41 but replacing 4-hydroxypiperidine with pyrrolidin-3-ol. $^1$H-NMR (400 MHz; d$_6$-DMSO) δ: 1.81-2.31 (m, 4H), 2.68-2.77 (m, 1H), 2.91-3.02 (m, 1H), 3.05-3.57 (m, 2H), 3.63-3.78 (m, 2H), 4.17-4.50 (m, 3H), 5.12 (d, 1H, J 8.5 Hz), 6.84-6.90 (m, 3H), 7.00 (dd, 1H, J 2.5, 8.8 Hz), 7.32-7.49 (m, 5H), 8.03 (dd, 1 H, J 2.7, 8.8 Hz), 8.36 (s, 1H), 10.40 (bd, 1H, J 30.3 Hz), 10.93 (d, 1H, J 3.2 Hz).

Example 45

1-{[6-(2-Phenylchroman-6-yloxy)pyridin-3-ylcarbamoyl]methyl}piperidine-4-carboxylic acid ethyl ester To a solution of 2-chloro-N-[6-(2-phenylchroman-6-yloxy)-pyridin-3-yl]acetamide (200 mg) in acetonitrile was added potassium carbonate (133 mg) piperidine-4-carboxylic acid ethyl ester (94 μl). The mixture was stirred at room temperature. Water was added to the reaction mixture. Solution was extracted with ethyl acetate. Organic extract was dried and evaporated. Product was purified by column chromatography using 10% methanol in methylenechloride as eluent. 1-{[6-(2-Phenylchroman-6-yloxy)pyridin-3-ylcarbamoyl]methyl}piperidine-4-carboxylic acid ethyl ester was isolated as its hydrochloride salt. $^1$H-NMR (400 MHz; d$_4$-MeOH) δ: 8.48 (s, 1H), 8.10 (dd, 1H, J 2.2, 9.0 Hz), 7.45-7.29 (m, 5H), 6.99-6.88 (m, 4H), 5.10 (dd, 1H, J 2.0, 10.0 Hz), 4.23-4.15 (m, 4H), 3.76-3.72 (m, 2H), 3.22-3.15 (m, 2H), 3.05-2.98 (m, 1H), 2.82-2.75 (m, 2H), 2.27-1.97 (m, 6H), 1.27 (t, 3H, J 7.2 Hz). (M)$^+$=515 (2.9%), 470 (4.3%), 360 (8.5%), 170 (100%).

Example 46

2-Diethylamino-N-[6-(2-phenylchroman-6-yloxy)pyridin-3-yl]acetamide

To a solution of 2-chloro-N-[6-(2-phenylchroman-6-yloxy)pyridin-3-yl]acetamide (200 mg) in acetonitrile was added potassium carbonate (133 mg) and diethyl amine (63 μl). The mixture was stirred at room temperature. Water was added to the reaction mixture. Solution was extracted with ethyl acetate. Organic extract was dried and evaporated. Product was purified by column chromatography using 10% methanol in methylenechloride as eluent. 2-Diethylamino-N-[6-(2-phenyl-chroman-6-yloxy)pyridin-3-yl]acetamide was isolated as its hydrochloride salt. $^1$H-NMR (400 MHz; d$_6$-DMSO) δ: 11.1 (s, 1H), 8.38 (d, 1H, J 2.7 Hz), 8.04 (dd, 1H, J 2.7, 8.9 Hz), 7.47-7.32 (m, 5H), 7.01 (d, 1H, J 8.9 Hz), 6.89-6.85 (m, 3H), 5.12 (dd, 1H, J 2.0, 10.0 Hz), 4.14 (d, 2H, J 4.9 Hz), 3.24 (k, 4H, J 7.2 Hz), 3.01-2.92 (m, 1H), 2.76-2.70 (m, 1H), 2.19-2.15 (m, 1H), 2.04-1.94 (m, 1H), 1.24 (t, 6H, J 7.2 Hz).

Example 47

2-Dimethylamino-N-[6-(2-phenylchroman-6-yloxy)pyridin-3-yl]acetamide

To a solution of 2-chloro-N-[6-(2-phenylchroman-6-yloxy)-pyridin-3-yl]-acetamide (177 mg) in acetonitrile was added potassium carbonate (118 mg) and 33% dimethylamine in ethanol (480 μl). The mixture was stirred at room temperature. Water was added to the reaction mixture. Solution was extracted with ethyl acetate. Organic extract was dried and evaporated. 2-Dimethylamino-N-[6-(2-phenyl-chroman-6-yloxy)-pyridin-3-yl]acetamide was isolated as its hydrochloride salt. $^1$H-NMR (300 MHz; d$_6$-DMSO) δ: 11.3 (s, 1H), 8.41 (d, 1H, J 2.3 Hz), 8.07 (dd, 1H, J 2.3, 8.8 Hz), 7.47-7.33 (m, 5H), 7.00 (d, 1H, J 8.8 Hz), 6.88-6.85 (m, 3H), 5.12 (d, 1H, J 8.5 Hz), 4.20 (s, 2H), 3.01-2.69 (m, 8H), 2.20-1.91 (m, 2H).

Example 48

2-[Bis(−2-hydroxyethyl)amino]-N-[6-(2-phenylchroman-6-yloxy)pyridin-3-yl]acetamide To a solution of 2-chloro-N-[6-(2-phenylchroman-6-yloxy)-pyridin-3-yl]acetamide (177 mg) in acetonitrile was added potassium carbonate (118 mg) and diethanolamine (65 µl). The mixture was stirred at room temperature. Water was added to the reaction mixture. Solution was extracted with ethyl acetate. Organic extract was dried and evaporated. 2-[Bis(2-hydroxyethyl)amino]-N-[6-(2-phenyl-chroman-6-yloxy)pyridin-3-yl]acetamide was purified by column chromatography using 10% methanol in methylenechloride as eluant. $^1$H-NMR (400 MHz; $d_6$-DMSO) δ: 10.1 (s, 1H), 8.31 (d, 1H, J 2.7 Hz), 8.07 (dd, 1H, J 2.7, 8.8 Hz), 7.46-7.31 (m, 5H), 6.95 (d, 1H, J 8.8 Hz), 6.86-6.84 (m, 3H), 5.11 (dd, 1H, J 2.1, 10.0 Hz), 4.71 (t, 2H, J 5.4 Hz), 3.50 (q, 4H, J 5.4 Hz), 2.97-2.92 (m, 1H), 2.74-2.70 (m, 1H), 2.67 (t, 4H, J 5.4 Hz), 2.18-2.14 (m, 1H), 2.02-1.97 (m, 1H).

Example 49

[6-(2-Phenylchroman-6-yloxy)pyridin-3-yl](2-pyrrolidin-1-ylethyl)amine

[6-(2-Phenylchroman-6-yloxy)pyridin-3-yl]-2-pyrrolidin-1-yl acetamide 0.20 g was dissolved in dry THF (2 ml) and solution of borane-THF complex (3.3 ml, 1.0 M in THF) was added dropwise under nitrogen. The reaction mixture was refluxed for 2 hours. Solvent was evaporated and the precipitate was diluted into methanol. The solution was acidified with 6 N HCl and stirred at 70° C. for an hour. After cooling into room temperature 5% NaOH solution was added and the mixture was extracted with ethyl acetate. The solvent was dried over $Na_2SO_4$ and evaporated under reduced pressure. [6-(2-Phenylchroman-6-yloxy)pyridin-3-yl](2-pyrrolidin-1-ylethyl)amine was isolated as its hydrochloride salt. $^1$H NMR (400 MHz, $d_6$-DMSO) δ: 10.24 (br s, 1H), 7.60 (d, 1H, J 2.9 Hz), 7.38-7.45 (m, 4H), 7.34 (m, 1H), 7.19 (dd, 1H, J 2.9, 8.7 Hz), 6.75-6.82 (m, 4H), 5.09 (d, 1H, J 9.9 Hz), 3.57 (m, 2H), 3.38-3.43 (m, 2H), 3.29 (m, 2H), 3.03 (m, 2H); 2.94 (m, 1H), 2.69 (m, 1H), 2.16 (m, 1H), 1.99 (m, 1H), 1.89 (m, 2H).

The following examples 50-53 were prepared as described for [6-(2-phenylchroman-6-yloxy)pyridin-3-yl](2-pyrrolidin-1-ylethyl)amine in Example 49 replacing [6-(2-phenylchroman-6-yloxy)pyridin-3-yl]-2-pyrrolidin-1-yl acetamide with an appropriate acetamide derivative.

Example 50

N-Ethyl-N'-[6-(2-phenylchroman-6-yloxy)pyridin-3-yl]ethane-1,2-diamine dihydrochloride $^1$H NMR (400 MHz, $d_6$-DMSO) δ: 8.85 (br s, 2H), 7.60 (d, 1H, J 2.8 Hz), 7.38-7.45 (m, 4H), 7.34 (d, 1H, J 6.8 Hz), 7.21 (dd, 1H, J 3.0, 8.8 Hz), 6.76-6.83 (m, 4H), 5.10 (d, 1H, J 8.1 Hz), 3.36 (t, 2H, J 6.3 Hz), 3.06 (m, 2H), 2.92-2.97 (m, 3H), 2.69 (m, 1H), 2.16 (m, 1H), 2.01 (m, 1H), 1.21 (t, 3H, J 7.2 Hz).

Example 51

N*1*-[6-(2-Phenylchroman-6-yloxy)pyridin-3-yl]ethane-1,2-diamine dihydrochloride $^1$H NMR (400 MHz, $d_6$-DMSO) δ: 7.99 (br s, 2H), 7.58 (d, 1H, J 2.7 Hz), 7.38-7.45 (m, 4H), 7.34 (d, 1H, J 7.0 Hz), 7.17 (dd, 1H, J 3.0, 8.7 Hz), 6.75-6.82 (m, 4H), 5.10 (d, 1H, J 7.8 Hz), 3.27-3.30 (m, 2H), 2.93-2.97 (m, 3H), 2.69 (m, 1H), 2.16 (m, 1H), 1.99 (m, 1H).

Example 52

N,N-Diethyl-N'-[6-(2-phenylchroman-6-yloxy)pyridin-3-yl]ethane-1,2-diamine dihydrochloride $^1$H NMR (400 MHz, $d_6$-DMSO) δ: 7.61 (d, 1H, J 2.8 Hz), 7.38-7.45 (m, 4H), 7.34 (m, 1H), 7.19 (dd, 1H, J 2.8, 8.8 Hz), 6.75-6.83 (m, 4H), 5.10 (d, 1H, J 7.8 Hz), 3.42-3.44 (m, 2H), 3.18-3.22 (m, 6H), 2.92 (m, 1H), 2.69 (m, 1H), 2.14 (m, 1H), 1.99 (m, 1H), 1.21 (t, 6H, J 7.2 Hz).

Example 53

N,N-Dimethyl-N'-[6-(2-phenylchroman-6-yloxy)pyridin-3-yl]ethane-1,2-diamine dihydrochloride $^1$H NMR (400 MHz, $d_6$-DMSO) δ: 7.61 (d, 1H, J 2.8 Hz), 7.38-7.45 (m, 4H), 7.34 (m, 1H), 7.20 (dd, 1H, J 2.9, 8.8 Hz), 6.75-6.83 (m, 4H), 5.10 (d, 1H, J 8.0 Hz), 3.42 (t, 2H, J 6.2 Hz), 3.22 (t, 2H, J 6.2 Hz), 2.93 (m, 1H), 2.80 (s, 6H), 2.69 (m, 1H), 2.16 (m, 1H), 1.98 (m, 1H).

Example 54

Methanesulfonamide

N-{6-[2-(3-(N-methanesulfonyl(5-aminopyridin-6-yloxy-))phenyl)chroman-6-yloxy]-pyridin-3-yl}-methanesulfonamide Pyridine (620 µl) and methanesufonyl chloride (260 µl) were added into a cooled solution of 6-[2-(3-(5-aminopyridin-2-yloxy)phenyl)chroman-6-yloxy]-pyridin-3-ylamine (650 mg) in dry THF (11 ml). After stirring resulting mixture at room temperature for additional 2 hours 1 M hydrochloric acid was added. Solution was extracted with ethyl acetate. Combined organic layers were washed with water, dried with $Na_2SO_4$ and evaporated. N-{6-[2-(3-(N-methanesulfonyl(5-aminopyridin-6-yloxy-))phenyl)-chroman-6-yloxy]-pyridin-3-yl}methanesulfonamide was recrystallised from mixture of methanol and diethyl ether. $^1$H NMR (300 MHz, $d_6$-DMSO) δ: 9.74 (s, 1H), 9.67 (s, 1H), 8.02 (d, 1H, 2.7 Hz), 7.98 (d, 1H, J 2.7 Hz), 7.72 (dd, 1H, J 2.7, 8.8 Hz), 7.67 (dd, 1H, J 2.7, 8.8 Hz), 7.44 (t, 1H, J 7.8 Hz), 7.30 (d, 1H, 7.8 Hz), 7.20 (s, 1H), 7.09-7.05 (m, 2H), 6.97 (d, 1H, J 8.8 Hz), 6.89-6.85 (m, 3H), 5.14 (d, 1H J 8.5 Hz), 3.00 (s, 3H), 2.98 (m, 3H), 2.98-2.91 (m, 1H), 2.75-2.70 (m, 1H), 2.21-2.17 (m, 1H), 2.02-1.97 (m, 1H).

6-[(N-methanesulfonyl(5-aminopyridin-6-yloxy-)]-2-{3-[N-methanesulfonyl-(5-aminopyridin-6-yloxy-)]phenyl}chroman-4-ol $^1$H NMR (300 MHz, $d_6$-DMSO) δ: 9.73 (s, 1H), 9.66 (s, 1H), 8.03 (d, 1H, J 2.6 Hz), 7.99 (d, 1H, J 2.6 Hz), 7.71-7.66 (m, 2H), 7.45 (t, 1H, J 7.8 Hz), 7.32 (d, 1H, J 7.8 Hz), 7.22-6.80 (m, 7H), 5.29 (d, 1H J 11.5 Hz), 4.95 (dd, 1H, J 6.1, 10.5 Hz), 3.00 (s, 3H), 2.99 (s, 3H), 2.38-2.31 (m, 1H), 1.99-1.91 (m, 1H).

N-{6-[2-(3-Benzyloxyphenyl)chroman-6-yloxy]pyridin-3-yl}methanesulfonamide $^1$H NMR (300 MHz, $d_6$-DMSO) δ: 9.64 (s, 1H), 7.98 (d, 1H, J 2.8 Hz), 7.66 (dd, 1H, J 2.8, 8.9 Hz), 7.47-7.28 (m, 6H), 7.09 (s, 1H), 7.04-6.94 (m, 3H), 6.89-6.85 (m, 3H), 5.12 (s, 2H), 5.09 (dd, 1H, J 2.1, 12.0 Hz), 2.98 (s, 3H), 2.98-2.89 (m, 1H), 2.73-2.67 (m, 1H) 2.20-2.14 (m, 1H), 2.02-1.96 (m, 1H).

N-{6-[2-(3-Hydroxyphenyl)chroman-6-yloxy]pyridin-3-yl}methanesulfonamide $^1$H NMR (400 MHz, d$_6$-DMSO) δ: 9.42 (s, 1H), 7.98 (d, 1H, J 2.8 Hz), 7.66 (dd, 1H, J 2.8, 8.8 Hz), 7.18 (t, 1H, J 8.0 Hz), 6.97 (d, 1H, J 8.8 Hz), 6.88-6.83 (m, 5H), 6.73-6.69 (m, 1H), 5.03 (dd, 1H J 2.1, 9.9 Hz), 2.98 (s, 3H), 2.98-2.90 (m, 1H), 2.72-2.67 (m, 1H), 2.16-2.11 (m, 1H), 1.98-1.91 (m, 1H).

Example 55

N-(6-{2-[3-(5-Nitropyridin-2-yloxy)phenyl]chroman-6-yloxy}pyridin-3-yl)-methanesulfonamide Potassium fluoride (42 mg) was added into a solution of N-{6-[2-(3-hydroxy-phenyl)chroman-6-yloxy]pyridin-3-yl}methanesulfonamide (100 mg) in dry DMF (1 ml). After stirring the resulting mixture at 120° C. for 30 minutes 2-chloro-5-nitropyridine (40 mg) was added. The reaction mixture was stirred for a further 30 minutes at 120° C. After cooling into room temperature 1 M HCl-solution was added and formed precipitate was filtered. N-(6-{2-[3-(5-Nitropyridin-2-yloxy)phenyl]-chroman-6-yloxy}pyridin-3-yl)methanesulfonamide was purified by column chromatography using 1:1 mixture of ethyl acetate and heptane as eluant. $^1$H NMR (300 MHz, d$_6$-DMSO) δ: 9.64 (s, 1H), 9.04 (d, 1H, J 2.9 Hz), 8.63 (dd, 1H, J 2.9, 9.1 Hz), 7.98 (d, 1H, J 2.7 Hz), 7.66 (dd, 1H, J 2.7, 8.8 Hz), 7.52 (t, 1H, J 7.7 Hz), 7.39 (d, 1H, J 7.7 Hz), 7.31 (s, 1H), 7.27 (d, 1H, J 9.1 Hz), 7.22-7.19 (m, 1H), 6.96 (d, 1H, J 8.8 Hz), 6.89-6.85 (m, 3H), 5.17 (d, 1H, J 7.8 Hz), 2.97 (s, 3H), 2.98-2.92 (m, 1H), 2.76-2.69 (m, 1H) 2.28-2.19 (m, 1H), 2.02-1.97 (m, 1H).

Example 56

(5-Nitropyridin-2-yl)(6-{2-[3-(5-nitropyridin-2-yloxy)phenyl]chroman-6-yloxy}pyridin-3-yl)amine 5-Nitropyridin-2-yl)(6-{2-[3-(5-nitropyridin-2-yloxy)phenyl]chroman-6-yloxy}pyridin-3-yl)amine was prepared using the same procedure as described for 5-nitro-2-(2-phenylchroman-6-yloxy)pyridine in Example 1 (b) starting from N-{6-[2-(3-hydroxyphenyl)chroman-6-yloxy]pyridine-3-yl}methanesulfonamide. $^1$H NMR (300 MHz, d$_6$-DMSO) δ: 10.14 (s, 1H), 9.02 (m, 1H), 8.63 (dd, 1H, J 2.8, 8.8 Hz), 8.40 (d, 1H, J 2.8 Hz), 8.30 (dd, 1H, J 2.8, 9.2 Hz), 8.13 (dd, 1H, J 2.6, 8.6 Hz), 7.52 (t, 1H, J 7.9 Hz), 7.40 (d, 1H, J 7.8 Hz), 7.31 (s, 1H), 7.28 (d, 1H, J 9.2 Hz), 7.21 (dd, 1H, J 2.1, 7.9 Hz), 6.70 (d, 1H, J 8.8 Hz), 6.85-6.90 (m, 5H), 5.18 (d, 1H, J 8.1 Hz), 2.97 (m, 1H), 2.74 (m, 1H), 2.23 (m, 1H), 2.02 (m, 1H).

Example 57

N-{6-[2-(3-(N-Acyl(5-aminopyridin-6-yloxy-))phenyl)chroman-6-yloxy]pyridin-3-yl}-acetamide 6-[2-(3-(5-Aminopyridin-2-yloxy)phenyl)chroman-6-yloxy]pyridin-3-ylamine of Example 77 (289 mg) was dissolved in 3 ml of dry pyridine under nitrogen. DMAP (16 mg) was added. AcCl (240 μl) was added at room temperature into the reaction solution dropwise because of vigorous and exothermic reaction. The reaction was stirred for 4.5 hours at room temperature and quenched with slow addition of few drops of H$_2$O. 50 ml of toluene was added and evaporated to dryness. Toluene evaporation was repeated twice. Brownish product mixture was purified with column chromatography (10% methanol in dichloromethane) to give of crystalline slightly yellowish product. The product was further purified with recrystallization from methanol/diethyl ether $^1$H-NMR (400 MHz; CDCl$_3$) δ: 8.12-8.03 (m, 4H), 7.42-736 (m, 2H), 7.26-7.21 (m, 2H), 7.15 (s, 1H), 7.06 (dd, 1H, J 1.7, 8.0 Hz), 6.91-6.82 (m, 5H), 5.08 (dd, 1H, J 9.6, 2.3 Hz), 3.02-2.90 (m, 1H), 2.80-2.70 (m, 1H), 2.28-2.14 (m, 71), 2.14-2.01 (m, 1H).

Example 58

N-(6-{2-[3-(5-Nitropyridin-2-yloxy)phenyl]chroman-6-yloxy}pyridin-3-yl)acetamide a) N-{6-[2-(3-Hydroxyphenyl)chroman-6-yloxy]pyridin-3-yl}acetamide was prepared as described for N-(6-{2-[3-(5-acetylaminopyridin-2-yloxy)-phenyl]-chroman-6-yloxy}pyridin-3-yl)acetamide in Example 57 starting from 3-[6-(5-aminopyridin-2-yloxy)chroman-2-yl]phenol using 1.2 eq. AcCl. $^1$H NMR (400 MHz, d$_6$-DMSO) δ: 10.03 (s, 1H), 9.42 (s, 1H), 8.27 (d, 1H, J 2.6 Hz), 8.01 (dd, 1H, J 8.8, 2.6 Hz), 7.18 (t, 1H, J 8.0 Hz), 6.93 (d, 1H, J 8.8 Hz), 6.84-6.85 (m, 5H), 6.72 (d, 1H, J 8.9 Hz), 5.03 (d, 1H, J 8.2 Hz), 2.94 (m, 1H), 2.70 (m, 1H), 2.14 (m, 1H), 2.04 (s, 3H), 1.94 (m, 1H).

b) N-(6-{2-[3-(5-Nitropyridin-2-yloxy)phenyl]chroman-6-yloxy}pyridin-3-yl)acetamide was prepared as described for 5-nitro-2-(2-phenylchroman-6-yloxy)pyridine in Example 1(b) starting from N-{6-[2-(3-hydroxyphenyl)chroman-6-yloxy]pyridin-3-yl}acetamide. $^1$H NMR (400 MHz, d$_6$-DMSO) δ: 10.03 (s, 1H), 9.05 (d, 1H, J 2.1 Hz), 8.63 (d, 1H, J 8.9 Hz), 8.26 (s, 1H), 8.00 (m, 1H), 7.50 (m, 1H), 7.40 (m, 1H), 7.27-7.31 (m, 2H), 7.20 (m, 1H), 6.92 (d, 1H, J 8.9 Hz), 6.85-6.87 (m, 3H), 5.17 (d, 1H, J 10.4 Hz), 2.96 (m, 1H), 2.71 (m, 1H), 2.20 (m, 1H), 2.04 (s, 3H), 1.99 (m, 1H).

Example 59

N-Methyl-N'-[6-(2-phenylchroman-6-yloxy)pyridin-3-yl]guanidine a) 1-Methyl-3-[6-(2-phenylchroman-6-yloxy)pyridin-3-yl]thiourea Solution of 6-(2-phenylchroman-6-yloxy)pyridin-3-ylamine (150 mg) and methyl isothiocyanate (94 μl) in ethanol was refluxed for 10 hours. After cooling solvents were evaporated. Crude product of 1-methyl-3-[6-(2-phenylchroman-6-yloxy)pyridin-3-yl]thiourea was purified by column chromatography (5% methanol in dichloromethane). $^1$H NMR (400 MHz, d$_6$-DMSO) δ: 9.45 (bs, 1H), 8.02 (d, 1H, J 2.7 Hz), 7.81 (dd, 1H, J 2.7, 8.8 Hz), 7.70 (bs, 1H), 7.47-7.38 (m, 4H), 7.36-7.32 (m, 1H), 6.94-6.86 (m, 4H), 5.12 (dd, 1H J 2.3, 10.1 Hz), 2.98-2.93 (m, 1H), 2.90 (d, 3H, J 4.3 Hz), 2.76-2.71 (m, 1H), 2.19-2.15 (m, 1H), 2.15-1.99 (m, 1H).

b) N-Methyl-N'-[6-(2-phenylchroman-6-yloxy)pyridin-3-yl]guanidine

Solution of 1-methyl-3-[6-(2-phenylchroman-6-yloxy)pyridin-3-yl]thiourea (150 mg), methyliodide (36 μl) and acetone (15 ml) was refluxed for 90 minutes. Solvent was evaporated and residue was dissolved to 4 ml of methanol saturated with NH$_3$. Mixture was heated under preasure at 100° C. for 16 hours. Solvent was evaporated and residue was purified by column chromatography using 10% methanol in dichloromethane as eluant. $^1$H NMR (400 MHz, d$_6$-DMSO) δ: 9.35 (bs, 1H), 8.04 (d, 1H, J 2.7 Hz), 7.71 (dd, 1H, J 2.7, 8.8

Hz), 7.65 (bs, 1H), 7.47-7.34 (m, 5H), 7.05 (d, 1H, J 8.8 Hz), 6.90-6.88 (m, 3H), 5.13 (d, 1H J 7.9 Hz), 3.01-2.98 (m, 1H), 2.80 (d, 3H, J 4.4 Hz), 2.75-2.71 (m, 1H), 2.19-2.15 (m, 1H), 2.02-1.98 (m, 1H).

Example 60

Dimethyl-[6-(2-phenylchroman-6-yloxy)pyridin-3-yl]-amine and dimethyl-[2-(2-phenylchroman-6-yloxy)-pyridin-4-yl]-amine 5-Amino-2-(2-phenylchroman-6-yloxy)pyridine (ORM-10543) (0.20 g, 0.63 mmol) and 37% formaldehyde (0.73 ml, 0.80 mmol) were dissolved in acetonitrile (12 ml). Sodium-cyanoborohydride (0.16 g, 2.51 mmol) was added and the mixture was stirred for 30 minutes at the room temperature. The pH was adjusted to 6-7 with acetic acid and the reaction mixture was stirred additional 30 minutes. The solvent was evaporated. The residue was solvated to 10% potassiumhydroxide solution and extracted with methylene chloride. Organic phase was dried and evaporated. Recrystallization from diethylether yielded dimethyl-[6-(2-phenylchroman-6-yloxy)pyridin-3-yl]-amine in 92% purity. Recrystallization filtrate was evaporated. The residue was solvated in methylene chloride and 1M HCl-diethylether was added. Dimethyl-[2-(2-phenylchroman-6-yloxy)-pyridin-4-yl]-amine precipitated as a hydrochloride in 95.3% purity.

Dimethyl-[6-(2-phenylchroman-6-yloxy)pyridin-3-yl]-amine $^1$H-NMR (400 MHz; $d_6$-DMSO) δ: 2.01 (m, 1H), 2.18 (m, 1H), 2.76 (m, 1H), 2.95 (s, 6H), 2.95-3.04 (m, 1H), 5.14 (d, 1H, J 8.2 Hz), 6.91-6.99 (m, 4H), 7.35-7.48 (m, 5H), 7.63 (d, 1H, J 3.1 Hz), 7.72 (dd, 1H, 3.2, 9.4 Hz).

Dimethyl-[2-(2-phenylchroman-6-yloxy)-pyridin-4-yl]-amine $^1$H-NMR (400 MHz; $d_6$-DMSO) δ: 1.99 (m, 1H), 2.16 (m, 1H), 2.69 (m, 1H), 2.86 (s, 6H), 2.94 (m, 1H), 5,10 (d, 1H, J 9.2 Hz), 6.75-6.86 (m, 4H), 7.27-7.35 (m, 2H), 7.37-7.48 (m, 4H), 7.65 (d, 1H, 2.9 Hz).

Example 61

5-Chloropyridinyloxy

5-Chloro-2-(2-phenylchroman-6-yloxy)pyridine

2-Phenylchroman-6-ol (500 mg) was dissolved in dry DMF (5 ml) under nitrogen. Potassium tert-butoxide (270 mg) was added in to a sloution and the resulting mixture was stirred for 30 minutes. 2,5-Dichloropyridine was added and the mixture was stirred at 120° C. for 2.5 hours. The reaction mixture was allowed to cool to room temperature and 1 M HCl-solution was added and it was extracted with ethyl acetate. The combined organic phases were washed with water and saturated NaCl-solution and dried. The raw product was passed silica gel column using heptane-ethyl acetate (3:1) as an eluant and then recrystallised 2-propanol. $^1$H NMR (300 MHz, $d_6$-DMSO) δ: 8.19 (d, 1H, J 2.6 Hz), 7.92 (dd, 1H, 8.8, 2.6 Hz), 7.47-7.34 (m, 5H), 7.02 (d, 1H, J 8.8 Hz) 6.92-6.87 (m, 3H), 5.12 (dd, 1H, J 10.0, 2.1 Hz), 2.97 (m, 1H), 2.73 (m, 1H), 2.17 (m, 1H), 2.01 (m, 1H).

2-[2-(3-(5-Chloropyridin-2-yloxy)phenyl)chroman-6-yloxy]-5-chloropyridine was obtained in a same manner by using 200 mol-% of 2,5-dichloropyridine and starting from 2-(3-hydroxyphenyl)chroman-6-ol $^1$H NMR (400 MHz, $d_6$-DMSO) δ: 8.22 (d, 1H, J 2.6 Hz), 8.19 (d, 1H, J 2.9 Hz), 7.97 (dd, 1H, J 8.9, 2.6 Hz), 7.92 (dd, 1H, J 9.0, 2.9 Hz), 7.46 (t, 1H, J 7.9 Hz), 7.32 (d, 1H, J 7.8 Hz), 7.22, (s, 1H), 7.13-7.10 (m, 2H), 7.02 (d, 1H, J 9.2 Hz) 6.91-6.87 (m, 2H), 5.15 (dd, 1H, J 10.0, 2.1 Hz), 2.96 (m, 1H), 2.74 (m, 1H), 2.18 (m, 1H), 1.99 (m, 1H)

Using the same procedure as described above for 5-Chloro-2-(2-phenyl-chroman-6-yloxy)pyridine, but replacing 2-phenylchroman-6-ol by:
2-(4-Fluorophenyl)chroman-6-ol,
2-(3-fluorophenyl)chroman-6-ol,
2-(2-Fluorophenyl)chroman-6-ol,
2-(2,3-Difluorophenyl)chroman-6-ol,
2-(2,4-Difluorophenyl)chroman-6-ol,
2-(2,5-Difluorophenyl)chroman-6-ol,
2-(2,6-Difluorophenyl)chroman-6-ol,
2-(3,4-Difluorophenyl)chroman-6-ol,
2-(3,5-Difluorophenyl)chroman-6-ol,
2-(2-Trifluoromethylphenyl)chroman-6-ol,
2-(4-Trifluoromethylphenyl)chroman-6-ol,
2-(3-Chloro-4-fluorophenyl)chroman-6-ol,
2-(2-Chlorophenyl)chroman-6-ol,
2-(3-Chlorophenyl)chroman-6-ol,
2-(2,4-Dichlorophenyl)chroman-6-ol,
2-(3-Bromophenyl)chroman-6-ol,
2-(4-Ethylphenyl)chroman-6-ol,
2-(3-Methoxyphenyl)chroman-6-ol,
3-Methyl-2-phenylchroman-6-ol,
2-phenylchroman-7-ol,
6-hydroxyflavanone,
7-hydroxyflavanone,
6-Hydroxy-3-methyl-2-phenylchroman-4-one,
2-Phenyl-2,3-dihydrobenzo[1,4]dioxin-6-ol,
6-Phenyl-5,6,7,8-tetrahydronaphthalen-2-ol,
6-Hydroxy-2-phenyl-3,4-dihydro-2H-naphthalen-1-one,
2-Phenyl-2,3-dihydrobenzo[1,4]oxathiin-6-ol,
3-(3-Fluorophenyl)chroman-7-ol,
3-Phenylchroman-7-ol,
6-Hydroxyflavone,
2-Phenylindan-5-ol,
there can be obtained:
5-Chloro-2-[2-(4-fluorophenyl)chroman-6-yloxy]pyridine,
5-Chloro-2-[2-(3-fluorophenyl)chroman-6-yloxy]pyridine,
5-Chloro-2-[2-(2-fluorophenyl)chroman-6-yloxy]pyridine,
5-Chloro-2-[2-(2,3-difluorophenyl)chroman-6-yloxy]pyridine,
5-Chloro-2-[2-(2,4-difluorophenyl)chroman-6-yloxy]pyridine,
5-Chloro-2-[2-(2,5-difluorophenyl)chroman-6-yloxy]pyridine,
5-Chloro-2-[2-(2,6-difluorophenyl)chroman-6-yloxy]pyridine,
5-Chloro-2-[2-(3,4-difluorophenyl)chroman-6-yloxy]pyridine,
5-Chloro-2-[2-(3,5-difluorophenyl)chroman-6-yloxy]pyridine,
5-Chloro-2-[2-(2-trifluoromethylphenyl)chroman-6-yloxy]pyridine,
5-Chloro-2-[2-(4-trifluoromethylphenyl)chroman-6-yloxy]pyridine,
5-Chloro-2-[2-(3-chloro-4-fluorophenyl)chroman-6-yloxy]pyridine,
5-Chloro-2-[2-(2-chlorophenyl)chroman-6-yloxy]pyridine,
5-Chloro-2-[2-(3-chlorophenyl)chroman-6-yloxy]pyridine, 5-Chloro-2-[2-(2,4-dichlorophenyl)chroman-6-yloxy]pyridine, 5-Chloro-2-[2-(3-bromophenyl)chroman-6-yloxy]pyridine, 5-Chloro-2-[2-(4-ethylphenyl)chroman-6-yloxy]pyridine, 5-Chloro-2-[2-(3-methoxyphenyl)chroman-6-yloxy]pyridine, 5-Chloro-2-(3-methyl-2-phenylchroman-6-yloxy pyridine, 5-Chloro-2-(2-phenylchroman-7-yloxy)pyridine, 6-(5-Chloropyridin-2-yloxy)-2-phenylchroman-4-one, 7-(5-Chloropyridin-2-yloxy)-2-phenylchroman-4-one, 6-(5-Chloropyridin-2-yloxy)-3-methyl-2-phenylchroman-4-one, 5-Chloro-2-(2-phenyl-2,3-dihydrobenzo[1,4]dioxin-6-yloxy)pyridine, 5-Chloro-2-(6-phenyl-5,6,7,8-tetrahydronaphthalen-2-yloxy)pyridine, 6-(5-Chloropyridin-2-yloxy)-2-phenyl-3,4-dihydro-2H-naphthalen-1-one, 5-Chloro-2-(2-phenyl-2,3-dihydrobenzo[1,4]oxathiin-6-yloxy)pyridine, 5-Chloro-2-[3-(3-fluorophenyl)chroman-7-yloxy]pyridine, 5-Chloro-2-(3-phenylchroman-7-yloxy)pyridine, 6-(5-Chloropyridin-2-yloxy)-2-phenylchromen-4-one, 5-Chloro-2-(2-phenylindan-5-yloxy)pyridine, respectively.

Example 62

2-Pyridine 2-(2-Phenylchroman-6-yloxy)pyridine 2-(2-Phenylchroman-6-yloxy)pyridine was obtained in a same manner than 5-Chloro-2-(2-phenylchroman-6-yloxy)pyridine in Example 61, but replacing 2,5-dichloropyridine with 2-chloropyridine. $^1$H NMR (400 MHz, d$_6$-DMSO) δ: 8.13 (dd, 1H, J 5.1, 1.9 Hz), 7.81 (ddd, 1H, 8.6, 6.9, 1.9 Hz), 7.47-7.32 (m, 5H), 7.08 (dd, 1H, J 6.9, 5.1 Hz), 6.95 (d, 1H, J 8.6 Hz), 6.90-6.86 (m, 3H), 5.11 (dd, 1H, J 10.2, 2.2 Hz), 2.97 (m, 1H), 2.73 (m, 1H), 2.17 (m, 1H), 2.01 (m, 1H).

2-[2-(3-(pyridin-2-yloxy)phenyl)chroman-6-yloxy]pyridine was obtained in a same manner by using 200 mol-% of 2-chloropyridine and starting from 2-(3-hydroxyphenyl)chroman-6-ol. $^1$H NMR (400 MHz, d$_6$-DMSO) δ: 8.17 (dd, 1H, J 4.1, 1.7 Hz), 8.13 (dd, 1H, J 4.1, 1.0 Hz), 7.86 (ddd, 1H, J 8.6, 7.5, 1.7 Hz), 7.81 (ddd, 1H, 8.5, 7.5, 1.0 Hz), 7.45 (t, 1H, J 7.9 Hz) 7.30 (d, 1H, J 7.5 Hz), 7.20 (s, 1H), 7.15-7.06 (m, 3H), 7.04 (d, 1H, J 8.6 Hz), 6.95 (d, 1H, J 8.5 Hz), 6.89-6.86 (m, 3H), 5.15 (d, 1H, J 8.7 Hz), 2.95 (m, 1H), 2.73 (m, 1H), 2.21 (m, 1H), 2.00 (m, 1H).

Example 63

4-(2-Phenyl-chroman-6-yloxy)-pyridine 4-(2-Phenyl-chroman-6-yloxy)-pyridine was obtained in a same manner than 5-Chloro-2-(2-phenylchroman-6-yloxy)pyridine in Example 61, but replacing 2,5-dichloropyridine with 4-chloropyridine. $^1$H NMR (400 MHz, d$_6$-DMSO) δ: 8.43 (dd, 2H, J 4.8, 1.5 Hz), 7.47-7.33 (m, 5H), 6.98-6.93 (m, 3H), 6.88 (dd, 2H, J 4.8, 1.5 Hz), 5.14 (dd, 1H, J 10.2, 2.2 Hz), 2.99 (m, 1H), 2.75 (m, 1H), 2.18 (m, 1H), 2.01 (m, 1H).

Example 64

6-Nicotinamide 6-(2-Phenylchroman-6-yloxy) nicotinamide 6-(2-Phenylchroman-6-yloxy) nicotinamide was obtained in a same manner than 5-Chloro-2-(2-phenylchroman-6-yloxy)pyridine in Example 61, but replacing 2,5-dichloropyridine with 6-chloronicotinamide. $^1$H NMR (400 MHz, d$_6$-DMSO) δ: 8.61 (d, 1H, J 2.4 Hz), 8.23 (dd, 1H, J 8.7, 2.4 Hz), 8.00 (bs, 1H), 7.47-7.32 (m, 6H), 7.01 (d, 1H, J 8.7 Hz), 6.93-6.86 (m, 3H), 5.13 (dd, 1H, J 8.2, 1.9 Hz), 3.00 (m, 1H), 2.73 (m, 1H), 2.17 (m, 1H), 2.02 (m, 1H).

6-(2-[3-(5-Carbamoylpyridin-2-yloxy)phenyl]phenylchroman-6-yloxy) nicotinamide was obtained in a same manner by using 200 mol-% of 6-chloronicotin-amide and starting from 2-(3-hydroxyphenyl)chroman-6-ol.

$^1$H NMR (400 MHz, d$_6$-DMSO) δ: 8.63 (d, 1H, J 2.4 Hz), 8.61 (d, 1H, J 2.4 Hz), 8.27 (dd, 1H, J 8.6, 2.4 Hz), 8.23 (dd, 1H, J 8.7, 2.4 Hz), 8.03 (bs, 1H), 8.00 (bs, 1H), 7.48 (t, 1H, J 7.9 Hz), 7.46 (bs, 1H), 7.44 (bs, 1H), 7.35 (d, 1H, J 7.7 Hz), 7.25, (s, 1H), 7.14 (dd, 1H, 7.9, 7.7 Hz), 7.11 (d, 1H, J 8.7 Hz), 7.01 (d, 1H, 8.6 Hz), 6.93-6.89 (m, 3H), 5.17 (d, 1H, J 8.7 Hz), 2.97 (m, 1H), 2.76 (m, 1H), 2.20 (m, 1H), 1.99 (m, 1H).

Example 65

C-[6-(2-Phenylchroman-6-yloxy)pyridin-3-yl]methylamine hydrochloride

Into a solution of 6-(2-Phenylchroman-6-yloxy) nicotinamide (100 mg) in dry THF (2.0 ml) was added dropwise a solution of borane-THF complex (0.6 ml, 1.0 M in THF). The resulting mixture was refluxed for 4 hours. After cooling to the room temperature 3 M HCl solution was added and THF was evaporated in vacuum. The mixture was made alkaline with 50% NaOH-solution and extracted with ethyl acetate and dried. The hydrochloride of C-[6-(2-phenylchroman-6-yloxy)pyridin-3-yl]methylamine was obtained via treatment with HCL-ether solution. $^1$H NMR (400 MHz, d$_6$-DMSO) δ: 8.29 (bs, 3H), 8.21 (s, 1H), 7.95 (d, 1H, J 8.5 Hz), 7.47-7.34 (m, 5H), 7.03 (d, 1H, J 8.5 Hz), 6.89-6.86 (m, 3H), 5.13 (d, 1H, J 8.4 Hz), 4.00 (m, 2H), 2.94 (m, 1H), 2.70 (m, 1H), 2.19 (m, 1H), 2.00 (m, 1H).

Example 66

Dimethyl-[6-(2-phenylchroman-6-yloxy)pyridin-3-ylmethyl]amine a) (6-Chloropyridin-3-ylmethyl)dimethylamine 2-Chloro-5-(chloromethyl)pyridine (500 mg) was dissolved in ethanol (7.0 ml). dimethylamine (0.83 ml, 33% in ethanol) and potassium carbonate (641 mg) were added and the resulting mixture was refluxed for 1.5 hours. After evaboration of ethanol, water was added and the aqueous mixture was extracted with ethyl acetate. $^1$H NMR (400 MHz, d$_6$-DMSO) δ: 8.31 (d, 1H, J 2.3 Hz), 7.77 (dd, 1H, J 8.2, 2.3 Hz), 7.47 (d, 1H, J 8.2 Hz), 3.41 (s, 2H), 2.14 (s, 6H).

b) Dimethyl-[6-(2-phenylchroman-6-yloxy)pyridin-3-ylmethyl]amine

Dimethyl-[6-(2-phenylchroman-6-yloxy)pyridin-3-ylmethyl]amine was prepared as described for 5-Chloro-2-(2-phenylchroman-6-yloxy)pyridine in Example 61, but replacing 2,5-dichloropyridine with (6-chloropyridin-3-ylmethyl)dimethylamine. $^1$H NMR (400 MHz, CDCl$_3$) δ: 8.03 (d, 1H, J 2.3 Hz), 7.65 (dd, 1H, J 8.4, 2.3 Hz), 7.44-7.32 (m, 5H), 6.92-6.88 (m, 3H), 6.84 (d, 1H, J 8.4 Hz), 5.05 (dd, 1H, J 10.2, 2.3 Hz), 3.36 (s, 2H), 3.02 (m, 1H), 2.80 (m, 1H), 2.23 (s, 1H), 2.19 (m, 1H), 2.10 (m, 1H).

Example 67

6-(2-Phenylchroman-6-yloxy)nicotinic acid methyl ester a) 6-Chloronicotinic acid methyl ester

6-Chloronicotinic acid (2.0 g) was dissolved in methanol and concentrated hydrochloric acid (3.0 ml) was added. The reaction mixture was refluxed for 5 hours and methanol was removed in vacuum. Ethyl acetate was added and the resulting solution was washed with saturated sodium bicarbonate solution, water and brine. $^1$H NMR (400 MHz,) δ: 8.92 (d, 1H, J 2.1 Hz), 8.32 (dd, 1H, J 8.4, 2.1 Hz), 7.70 (d, 1H, J 8.4 Hz), 3.90 (s, 3H).

b) 6-(2-Phenylchroman-6-yloxy) nicotinic acid methyl ester 6-(2-Phenylchroman-6-yloxy) nicotinic acid methyl ester was prepared as described for 5-Chloro-2-(2-phenylchroman-6-yloxy)pyridine in Example 61, but replacing 2,5-dichloropyridine with 6-chloronicotinic acid methyl ester. $^1$H NMR (400 MHz, CDCl$_3$) δ: 8.70 (d, 1H, J 2.4 Hz), 8.29 (dd, 1H, J 8.6, 2.4 Hz), 7.47-7.32 (m, 5H), 7.07 (d, 1H, J 8.6 Hz), 6.96-6.88 (m, 3H), 5.14 (d, 1H, J 10.0 Hz), 3.85 (s, 3H), 2.97 (m, 1H), 2.74 (m, 1H), 2.18 (m, 1H), 2.01 (m, 1H).

Example 68

6-(2-Phenylchroman-6-yloxy) nicotinic acid 6-(2-Phenylchroman-6-yloxy) nicotinic acid (200 mg), water (10 ml), ethanol (2 ml) and potassium hydroxide were placed in a flask. The resulting mixture was refluxed for 2.5 hours. After cooling to room temperature the pH was adjusted to pH 1 with concentrated hydrochloric acid and the white precipitate was filtered. $^1$H NMR (300 MHz, d$_6$-DMSO) δ: 13.12 (s, 1H), 8.67 (d, 1H, J 2.4 Hz), 8.25 (dd, 1H, J 8.6, 2.4 Hz), 7.48-7.34 (m, 5H), 7.04 (d, 1H, J 8.6 Hz), 6.95-6.86 (m, 3H), 5.14 (dd, 1H, J 10.0, 2.2 Hz), 2.99 (m, 1H), 2.74 (m, 1H), 2.17 (m, 1H), 2.01 (m, 1H).

Example 69

6-Nicotinonitrile

6-(2-Phenylchroman-6-yloxy)nicotinonitrile 6-(2-Phenylchroman-6-yloxy)nicotinonitrile was prepared as described for 5-nitro-2-(2-phenylchroman-6-yloxy)pyridine in example 1 (b) using 500 mg of 2-phenylchroman-6-ol and replacing 2-chloro-5-nitropyridine by 337 mg of 6-chloro-nicotinonitrile. The product was purified by column chromatography using heptane-ethyl acetate as an eluant and then crystallised from 2-propanol. $^1$H NMR (400 MHz, d$_6$-DMSO) δ: 8.65 (d, 1H, J 2.4 Hz), 8.28 (dd, 1H, 8.8, 2.4 Hz), 7.47-7.34 (m, 5H), 7.17 (d, 1H, J 8.8 Hz) 6.96-6.87 (m, 3H), 5.14 (dd, 1H, J 10.1, 2.2 Hz), 2.99 (m, 1H), 2.73 (m, 1H), 2.18 (m, 1H), 2.00 (m, 1H).

6-{2-[3-(5-Cyanopyridin-2-yloxy)-phenyl]chroman-6-yloxy}nicotinonitrile was obtained in a same manner by using 200 mol-% of 6-Chloronicotinonitrile and starting from 2-(3-hydroxyphenyl)chroman-6-ol. $^1$H NMR (400 MHz, d$_6$-DMSO) δ: 8.66 (d, 1H, J 2.2 Hz), 8.64 (d, 1H, J 2.3 Hz), 8.33 (dd, 1H, J 8.6, 2.3 Hz), 8.28 (dd, 1H, J 8.7, 2.2 Hz), 7.50 (t, 1H, J 7.8 Hz), 7.38 (d, 1H, J 7.8 Hz), 7.28, (s, 1H), 7.26 (d, 1H, 8.6 Hz), 7.19-7.16 (m, 2H), 6.97-6.88 (m, 2H), 5.18 (d, 1H, J 8.3 Hz), 2.97 (m, 1H), 2.74 (m, 1H), 2.22 (m, 1H), 2.01 (m, 1H).

Example 70

3-(2-Phenylchroman-6-yloxy)pyridine

2-Phenylchroman-6-ol (598 mg), 3-bromopyridine (500 mg), potassium hydroxide (322 mg) and potassium iodide were placed in a flask with dry DMSO (10 ml). The reaction mixture was stirred at 120° C. for 3.5 hours. After cooling to room temperature 1M HCl-solution was added and the mixture was extracted wit dichloromethane. The combined organig extracts were washed with 1 M HCl-solution, then with water and brine and dried. 3-(2-Phenylchroman-6-yloxy)pyridine was purified by column chromatography using heptane-ethyl acetate as an eluant. $^1$H NMR (400 MHz, d$_6$-CDCl$_3$+MeOH) δ: 8.31 (s, 1H), 8.24 (dd, 1H, J 3.8, 1.9 Hz), 7.45-7.25 (m, 7H), 6.87 (d, 1H, J 8.6 Hz), 6.83 (dd, 1H, J 8.6, 2.6 Hz), 6.81 (d, 1H, J 2.6 Hz), 5.07 (dd, 1H, J 10.1, 2.3 Hz), 2.98 (m, 1H), 2.78 (m, 1H), 2.23 (m, 1H), 2.12 (m, 1H).

The invention claimed is:
1. A compound of formula (I) or (II):

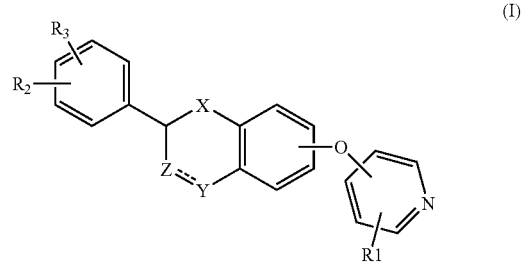

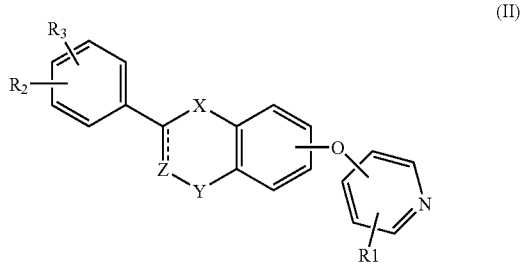

wherein
X is —O—, —CH$_2$— or —C(O)—;
Z is —CHR$_{12}$— or valence bond;
Y is —CH$_2$—, —C(O)—, CH(OR$_{13}$)—, —O—, —S—;
provided that in case Z is a valence bond, Y is not C(O);

the dashed line represents an optional double bond in which case Z is —CR$_{12}$— and Y is —CH$_2$—, —C(O)— or CH(OR$_{10}$)— (in formula II) or —CH— (in formula I);

R$_2$ and R$_3$ are independently H, lower alkyl, lower alkoxy, —NO$_2$, halogen, —CF$_3$, —OH, benzyloxy or a group of formula (IIIa)

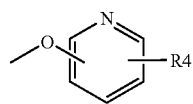
(IIIa)

R$_1$ is H, CN, halogen, —CONH$_2$,—COOR$_{15}$, —CH$_2$NR$_{15}$R$_{18}$, NHC(O)R$_5$, NHCH$_2$R$_5$, NHR$_{20}$, NR$_{21}$R$_{22}$, NHC(NH)NHCH$_3$ or, in case the compound is of formula (II) wherein the optional double bond exists or in case R$_2$ or R$_3$ is benzyloxy or a group of formula (IIIa), R$_1$ can also be —NO$_2$ or NR$_{16}$R$_{17}$;

R$_4$ is H, —NO$_2$,CN, halogen, —CONH$_2$,—COOR$_{15}$, —CH$_2$NR$_{15}$R$_{18}$, —NR$_{16}$R$_{17}$, —NHC(O)R$_5$ or —NHC(NH)NHCH$_3$;

R$_5$ is alkyl substituted with 1-3 substituents selected from the group consisting of halogen, amino and hydroxy, or carboxyalkyl, in which the alkyl portion is optionally substituted with 1-3 substituents selected from the group consisting of halogen, amino and hydroxyl, —CHR$_6$NR$_7$R$_8$ or one of the following groups:

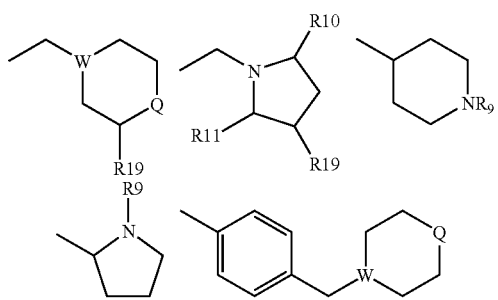

W is N or CH;
Q is CHR$_{14}$, NR$_9$, S or O;
R$_6$ is H or lower alkyl;
R$_7$ and R$_8$ are independently H, acyl, lower alkyl or lower hydroxyalkyl;
R$_9$ is H, lower alkyl or phenyl;
R$_{10}$ and R$_{11}$ are independently H or lower alkyl;
R$_{12}$ is H or lower alkyl;
R$_{13}$ is H, alkylsulfonyl or acyl;
R$_{14}$ is H, —OH, —COOR$_{15}$;
R$_{15}$ is H or lower alkyl;
R$_{16}$ and R$_{17}$ are independently H, acyl, alkylsulfonyl, —C(S)NHR$_{18}$ or —C(O)NHR$_{18}$;
R$_{18}$ is H or lower alkyl;
R$_{19}$ is H or —OH;
R$_{20}$ is a pyridinyl group optionally substituted with a —NO$_2$ group;
R$_{21}$ and R$_{22}$ are lower alkyl;
or a pharmaceutically acceptable salt or ester thereof.

2. A compound according to claim 1 wherein R$_1$ is —NHC(O)R$_5$, X is O, Y is CH$_2$ and Z is CHR$_{12}$.

3. A compound according to claim 2 wherein Z is CH$_2$ and R$_5$ is alkyl substituted with 1-3 substituents selected from the group consisting of halogen, amino and hydroxy, or carboxyalkyl, in which the alkyl portion is optionally substituted with 1-3 substituents selected from the group consisting of halogen, amino and hydroxyl, —CHR$_6$NR$_7$R$_8$ or one of the following groups:

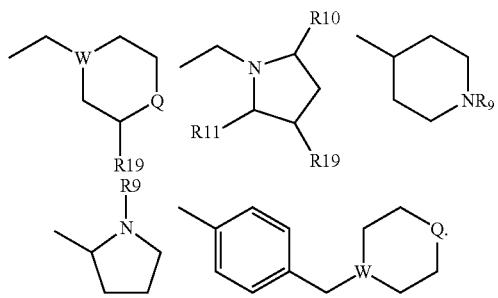

4. A compound according to claim 1 wherein R$_2$ or R$_3$ is a benzyloxy or a group of formula (IIIa)

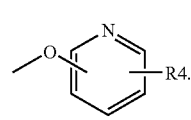
(IIIa)

5. A compound according to claim 4 wherein R$_4$ is NO$_2$.
6. A compound according to claim 4 wherein R$_1$ is NO$_2$.
7. A compound according to claim 5 wherein R$_1$ is NO$_2$.

* * * * *